United States Patent
Hurley et al.

(10) Patent No.: US 12,250,998 B2
(45) Date of Patent: Mar. 18, 2025

(54) LEVER-OPERATED ADJUSTMENT DEVICES, FIT SYSTEMS, AND LINE TENSIONING SYSTEMS

(71) Applicant: Garrett Ray Hurley, San Francisco, CA (US)

(72) Inventors: Garrett Ray Hurley, San Francisco, CA (US); Loren Maxwell Brock, Berkeley, CA (US)

(73) Assignee: Garrett Ray Hurley, San Francisco, CA (US)

( * ) Notice: Subject to any disclaimer, the term of this patent is extended or adjusted under 35 U.S.C. 154(b) by 613 days.

(21) Appl. No.: 17/615,772

(22) PCT Filed: Jun. 5, 2020

(86) PCT No.: PCT/US2020/036324
§ 371 (c)(1),
(2) Date: Dec. 1, 2021

(87) PCT Pub. No.: WO2020/247749
PCT Pub. Date: Dec. 10, 2020

(65) Prior Publication Data
US 2022/0304425 A1    Sep. 29, 2022

Related U.S. Application Data

(60) Provisional application No. 62/937,808, filed on Nov. 20, 2019, provisional application No. 62/857,320, filed on Jun. 5, 2019.

(51) Int. Cl.
*A43C 11/16*    (2006.01)
*A41F 9/02*    (2006.01)
(Continued)

(52) U.S. Cl.
CPC .............. *A44B 11/125* (2013.01); *A41F 9/02* (2013.01); *A43C 11/165* (2013.01); *A44B 11/02* (2013.01);
(Continued)

(58) Field of Classification Search
CPC ..... A44B 11/125; A44B 11/02; A43C 11/165; B65H 75/4471; B65H 75/4492;
(Continued)

(56) References Cited

U.S. PATENT DOCUMENTS 843,979 A    2/1907    Wantz
956,328 A    4/1910    Forshee
(Continued)

FOREIGN PATENT DOCUMENTS

WO    2018145802    8/2018

OTHER PUBLICATIONS

U.S. Pat. No. 0048121; Issued Jun. 6, 1865; Warner.
(Continued)

*Primary Examiner* — Robert Sandy
*Assistant Examiner* — Rowland Do
(74) *Attorney, Agent, or Firm* — Gordon & Jacobson, P.C.

(57) ABSTRACT

An adjustment device includes a housing supporting a rotatable spool that is operably coupled to a tension line. The spool is configured to rotate about a first axis in a first direction to wind the tension line around the spool and is configured to rotate about the first axis in a second direction opposite the first rotational direction to unwind the at least one tension line from the spool. The device includes a lever pivotally coupled to the housing and configured to rotate about a second axis. The lever is selectively coupled to the spool to drive rotation of the spool in the first direction. The device also includes a release mechanism that is configured (Continued)

to selectively release the spool such that the spool is free to rotate in either the first or second direction in response to manual forces applied to the release mechanism.

18 Claims, 38 Drawing Sheets

(51) Int. Cl.
- *A44B 11/02* (2006.01)
- *A44B 11/12* (2006.01)
- *B65H 75/40* (2006.01)
- *B65H 75/44* (2006.01)

(52) U.S. Cl.
CPC ....... *B65H 75/406* (2013.01); *B65H 75/4431* (2013.01); *B65H 75/4471* (2013.01); *B65H 75/4492* (2013.01); *B65H 2403/47* (2013.01); *B65H 2515/31* (2013.01)

(58) Field of Classification Search
CPC .............. B65H 2515/31; B65H 75/406; B65H 75/4431; B65H 2403/47; B60P 7/083; Y10T 24/2175; A41F 9/02
See application file for complete search history.

(56) References Cited

U.S. PATENT DOCUMENTS

| | | | |
|---|---|---|---|
| 1,107,934 A | 8/1914 | Hagan |
| 2,191,228 A | 2/1940 | Dowd |
| 2,604,098 A | 7/1952 | Kranc |
| 2,699,918 A | 1/1955 | Bush |
| 2,754,825 A | 7/1956 | Richmond |
| 2,889,136 A | 6/1959 | Prete, Jr. |
| 2,969,221 A | 1/1961 | Harmes |
| 3,175,806 A | 3/1965 | Prete, Jr. |
| 3,180,623 A | 4/1965 | John |
| 3,279,760 A | 10/1966 | Bathum, Jr. |
| 3,315,913 A | 4/1967 | Grieten |
| 3,667,698 A | 6/1972 | Fisher |
| 3,749,366 A | 7/1973 | Brucker |
| 3,825,979 A | 7/1974 | Jakob |
| 4,044,400 A | 8/1977 | Lewicki |
| 4,154,427 A | 5/1979 | Hofmann |
| 4,155,537 A | 5/1979 | Bronson |
| 4,199,182 A | 4/1980 | Sunesson |
| 4,278,002 A | 7/1981 | Siminoff |
| 4,345,726 A | 8/1982 | Noda |
| 4,414,713 A | 11/1983 | Prete, Jr. |
| 4,436,254 A | 3/1984 | Normann |
| 4,507,829 A | 4/1985 | Looker |
| 4,542,883 A | 9/1985 | Rutzki |
| 4,612,686 A | 9/1986 | Bowers |
| 4,613,273 A | 9/1986 | Wagner |
| 4,703,917 A | 11/1987 | Tomlinson |
| 4,738,410 A | 4/1988 | Yamaguchi |
| 4,823,443 A | 4/1989 | Waters |
| 5,203,541 A | 4/1993 | Nix |
| 5,271,606 A | 12/1993 | Hans-Werner |
| 5,295,664 A | 3/1994 | Hans-Werner |
| 5,325,613 A | 7/1994 | Sussmann |
| 5,426,827 A | 6/1995 | Tracy |
| 5,495,683 A | 3/1996 | Miotto |
| 5,542,798 A | 8/1996 | Rawdon |
| 5,606,779 A | 3/1997 | Lu |
| 5,720,084 A | 2/1998 | Chen |
| 5,800,105 A | 9/1998 | Stump |
| 5,904,341 A | 5/1999 | Norrby |
| 5,909,850 A | 6/1999 | Cavasin |
| 6,003,578 A | 12/1999 | Chang |
| 6,007,053 A | 12/1999 | Huang |
| 6,095,450 A | 8/2000 | Jang |
| 6,547,218 B2 | 4/2003 | Richard |
| 6,654,987 B1 | 12/2003 | Wu |
| 6,772,485 B2 | 8/2004 | Alpert |
| 6,824,121 B2 | 11/2004 | Boice |
| 6,880,810 B1 | 4/2005 | Hu |
| 7,207,089 B2 | 4/2007 | Hanson |
| 7,503,546 B1 | 3/2009 | Seager |
| 7,503,736 B1 | 3/2009 | Chen |
| 7,510,168 B1 | 3/2009 | Lin |
| 7,644,906 B2 | 1/2010 | Rodrigue |
| 7,877,845 B2 | 2/2011 | Signori |
| 8,099,836 B2 | 1/2012 | Breeden |
| 8,109,015 B2 | 2/2012 | Signori |
| 8,277,401 B2 | 10/2012 | Hammerslag |
| 8,308,410 B2 | 11/2012 | Foryan |
| 8,434,200 B2 | 5/2013 | Chen |
| 8,434,979 B1 | 5/2013 | Genge |
| 8,516,662 B2 | 8/2013 | Goodman |
| 8,680,997 B2 | 3/2014 | Gallagher |
| 8,794,378 B2 | 8/2014 | Wolner |
| 8,904,672 B1 | 12/2014 | Johnson |
| 8,919,293 B2 | 12/2014 | Cromwell |
| 8,967,332 B2 | 3/2015 | Wolner |
| 9,061,622 B2 * | 6/2015 | Knox ...................... B60P 7/083 |
| 9,138,030 B2 | 9/2015 | Soderberg |
| 9,179,729 B2 | 11/2015 | Cotterman |
| 9,185,942 B2 | 11/2015 | Rowland |
| 9,277,776 B2 | 3/2016 | Laatz |
| 9,285,776 B1 | 3/2016 | Custer |
| 9,296,534 B2 | 3/2016 | Gerhardt |
| 9,351,539 B2 | 5/2016 | Briggs |
| 9,572,405 B2 | 2/2017 | Saris |
| 9,597,786 B2 | 3/2017 | Romo |
| 9,635,906 B2 | 5/2017 | Midorikawa |
| 9,656,591 B1 | 5/2017 | Dumenigo |
| 9,657,485 B2 | 5/2017 | Meyers |
| 9,706,814 B2 | 7/2017 | Converse |
| 9,725,029 B2 | 8/2017 | Chou |
| 9,770,069 B2 | 9/2017 | Munns |
| 9,770,070 B2 | 9/2017 | Cotterman |
| 9,788,613 B2 | 10/2017 | Steffenhagen |
| 9,855,055 B2 | 1/2018 | Kosiorek |
| 9,867,430 B2 | 1/2018 | Hammerslag |
| 9,918,865 B2 | 3/2018 | Nickel |
| 9,956,094 B2 | 5/2018 | Mahon |
| 9,968,473 B2 | 5/2018 | Mason |
| 9,993,048 B2 | 6/2018 | Casebolt |
| 10,016,203 B2 | 7/2018 | Esposito |
| 10,070,695 B2 | 9/2018 | Burns |
| 10,076,160 B2 | 9/2018 | Burns |
| 10,077,570 B2 | 9/2018 | Underwood |
| 10,085,502 B1 | 10/2018 | Trepanier |
| 10,088,016 B2 | 10/2018 | Bujold |
| 10,160,419 B2 | 12/2018 | Wedeking |
| 10,227,030 B2 | 3/2019 | Kingery |
| 10,251,451 B2 | 4/2019 | Converse |
| 10,264,852 B2 | 4/2019 | Kim |
| 10,266,364 B2 | 4/2019 | Hitsman |
| 10,308,163 B2 | 6/2019 | Helline |
| 10,363,046 B2 | 7/2019 | Hopman |
| 10,413,019 B2 | 9/2019 | Soderberg |
| 10,414,323 B2 | 9/2019 | Willodson |
| 10,492,568 B2 | 12/2019 | Burns |
| 10,543,630 B2 | 1/2020 | Hipwood |
| 10,558,052 B2 | 2/2020 | Chang |
| 10,575,591 B2 | 3/2020 | Schum |
| 10,575,592 B1 | 3/2020 | Jones |
| 10,576,015 B2 | 3/2020 | Wang |
| 10,772,389 B2 | 9/2020 | Rossi |
| 10,935,104 B2 * | 3/2021 | D'Antonio ............... F16G 11/12 |
| 11,470,921 B2 | 10/2022 | Hurley |
| 11,751,641 B2 | 9/2023 | Hurley |
| 11,820,277 B2 * | 11/2023 | Chou ..................... B60P 7/083 |
| 2003/0097736 A1 | 5/2003 | Blankenship |
| 2003/0145434 A1 | 8/2003 | Lin |
| 2004/0155230 A1 | 8/2004 | Fortin |
| 2005/0087115 A1 | 4/2005 | Martin |
| 2005/0177984 A1 | 8/2005 | Huang |
| 2005/0267518 A1 | 12/2005 | Wright |
| 2006/0156517 A1 | 7/2006 | Hammerslag |
| 2007/0101615 A1 | 5/2007 | Munns |

(56) References Cited

U.S. PATENT DOCUMENTS

| | | |
|---|---|---|
| 2008/0104811 A1 | 5/2008 | Burrows |
| 2008/0184451 A1 | 8/2008 | Lemke |
| 2008/0216213 A1 | 9/2008 | Lin |
| 2008/0216291 A1 | 9/2008 | Lin |
| 2008/0232922 A1 | 9/2008 | Chang |
| 2009/0271976 A1 | 11/2009 | Huang |
| 2009/0283729 A1 | 11/2009 | Carlson |
| 2009/0300889 A1 | 12/2009 | Shiu |
| 2010/0071174 A1 | 3/2010 | Adcock |
| 2010/0137900 A1 | 6/2010 | Chao |
| 2010/0244543 A1 | 9/2010 | Fine |
| 2010/0293765 A1 | 11/2010 | Huang |
| 2012/0138883 A1 | 6/2012 | Gallagher |
| 2012/0205601 A1 | 8/2012 | Joubert |
| 2012/0227223 A1 | 9/2012 | Knox |
| 2013/0025100 A1 | 1/2013 | Ha |
| 2013/0092780 A1 | 4/2013 | Soderberg |
| 2013/0161365 A1 | 6/2013 | Shih |
| 2013/0269628 A1 | 10/2013 | Holt, Jr. |
| 2013/0318827 A1 | 12/2013 | Ringholz |
| 2013/0326847 A1 | 12/2013 | Zheng |
| 2013/0340292 A1 | 12/2013 | Cook |
| 2014/0061556 A1 | 3/2014 | Knox |
| 2014/0221889 A1 | 8/2014 | Burns |
| 2014/0338161 A1 | 11/2014 | Armour |
| 2015/0038889 A1 | 2/2015 | Mason |
| 2015/0040359 A1 | 2/2015 | Brown |
| 2015/0051638 A1 | 2/2015 | Dickinson |
| 2015/0053806 A1 | 2/2015 | Geisel |
| 2015/0121669 A1 | 5/2015 | Jungkind |
| 2015/0158615 A1 | 6/2015 | Downs |
| 2015/0191326 A1 | 7/2015 | Hall |
| 2015/0230560 A1 | 8/2015 | Chen |
| 2015/0257767 A1 | 9/2015 | Henderson |
| 2015/0289609 A1 | 10/2015 | Gittens |
| 2015/0359542 A1 | 12/2015 | Steinbaugh |
| 2016/0199206 A1 | 7/2016 | Lim |
| 2016/0206937 A1 | 7/2016 | Hanson |
| 2016/0207440 A1 | 7/2016 | Kingery |
| 2017/0100131 A1 | 4/2017 | Olbu |
| 2017/0295888 A1 | 10/2017 | Chen |
| 2017/0355298 A1 | 12/2017 | Cahall |
| 2018/0154862 A1 | 6/2018 | Wedeking |
| 2018/0334075 A1 | 11/2018 | Frank |
| 2019/0150569 A1 | 5/2019 | Chen |
| 2019/0216176 A1 | 7/2019 | Converse |

OTHER PUBLICATIONS

PCT Search Report and Written Opinion dated Aug. 18, 2020 of Application No. PCT/US 2020/036128.
PCT Search Report and Written Opinion dated Aug. 18, 2020 of Application No. PCT/US 2020/036140.
PCT Search Report and Written Opinion dated Sep. 9, 2020 of Application No. PCT/US 20/36324.
U.S. Appl. No. 62/857,320, filed Jun. 5, 2019.
U.S. Appl. No. 62/937,808, filed Nov. 20, 2019.

* cited by examiner

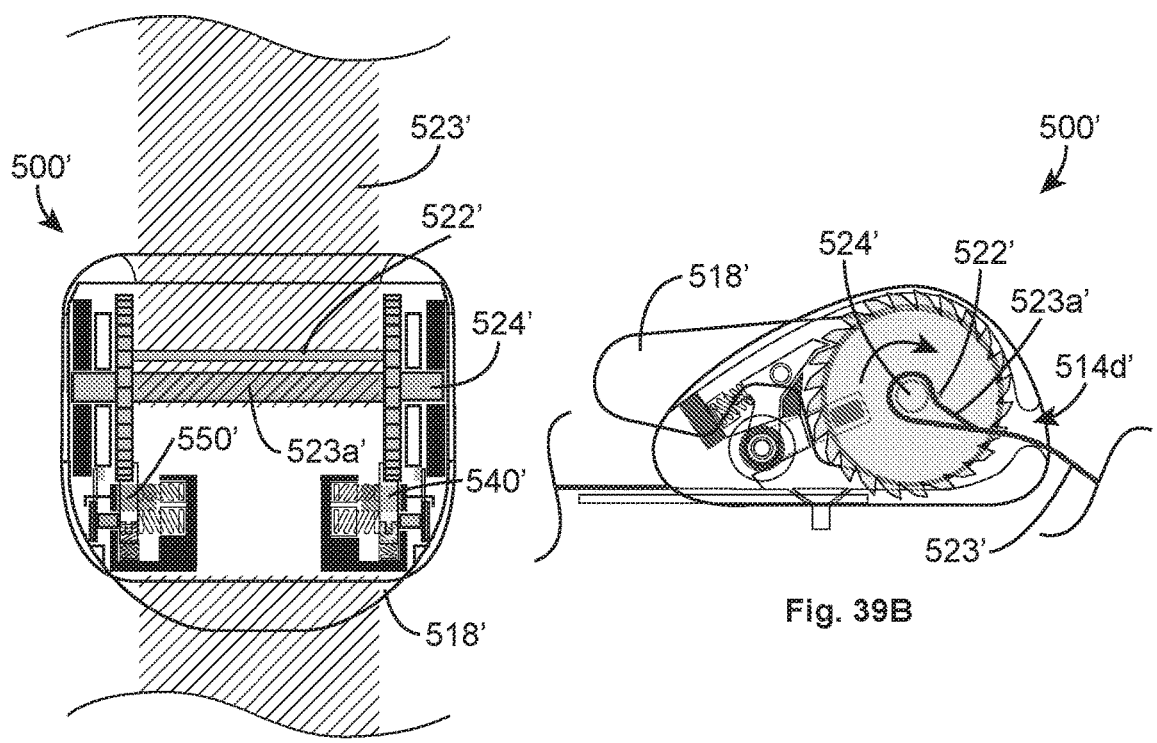
Fig. 39A
Fig. 39B
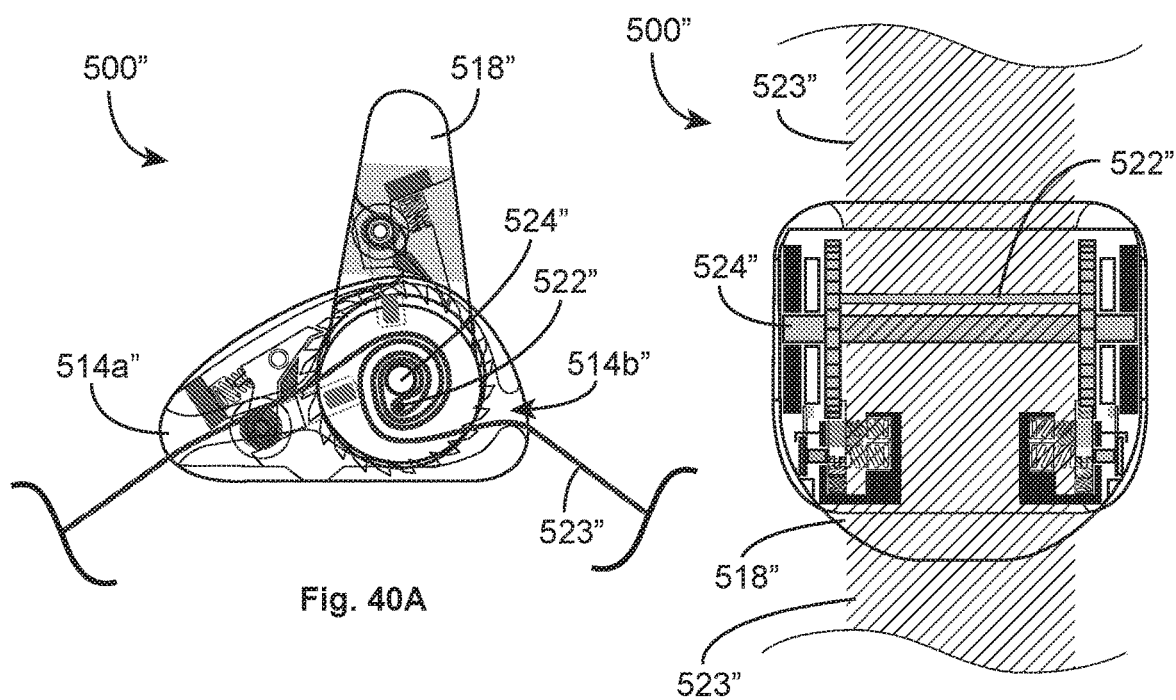
Fig. 40A
Fig. 40B

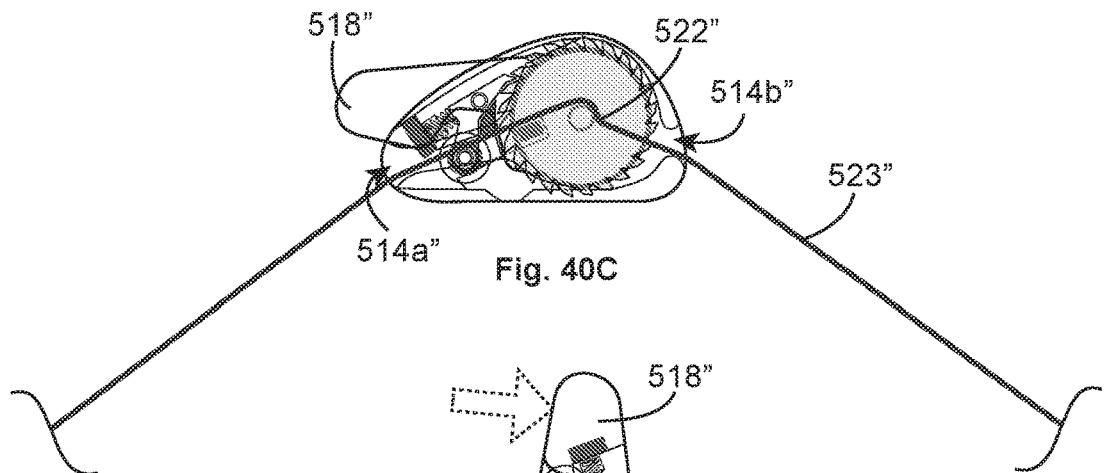
Fig. 40C
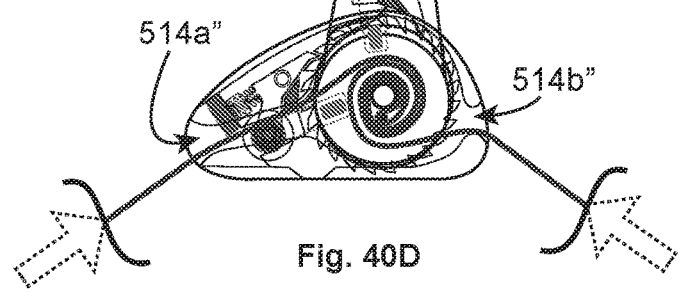
Fig. 40D
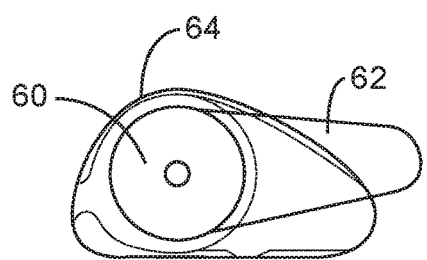
Fig. 41A
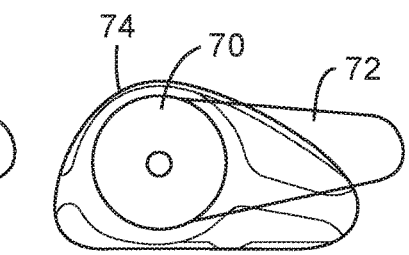
Fig. 42A
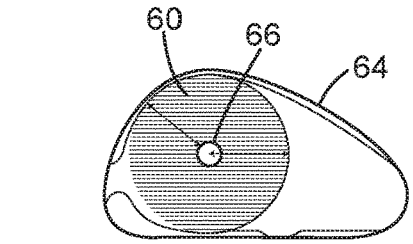
Fig. 41B
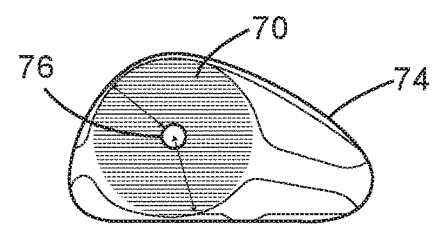
Fig. 42B
Fig. 41C
Fig. 42C

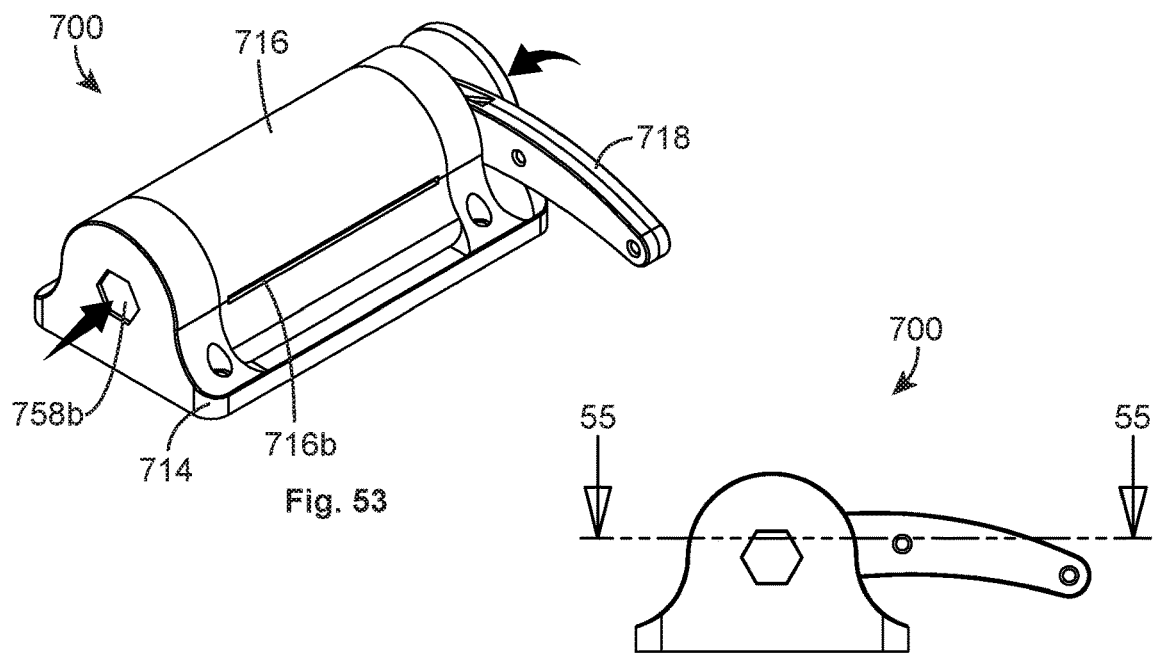
Fig. 53
Fig. 54
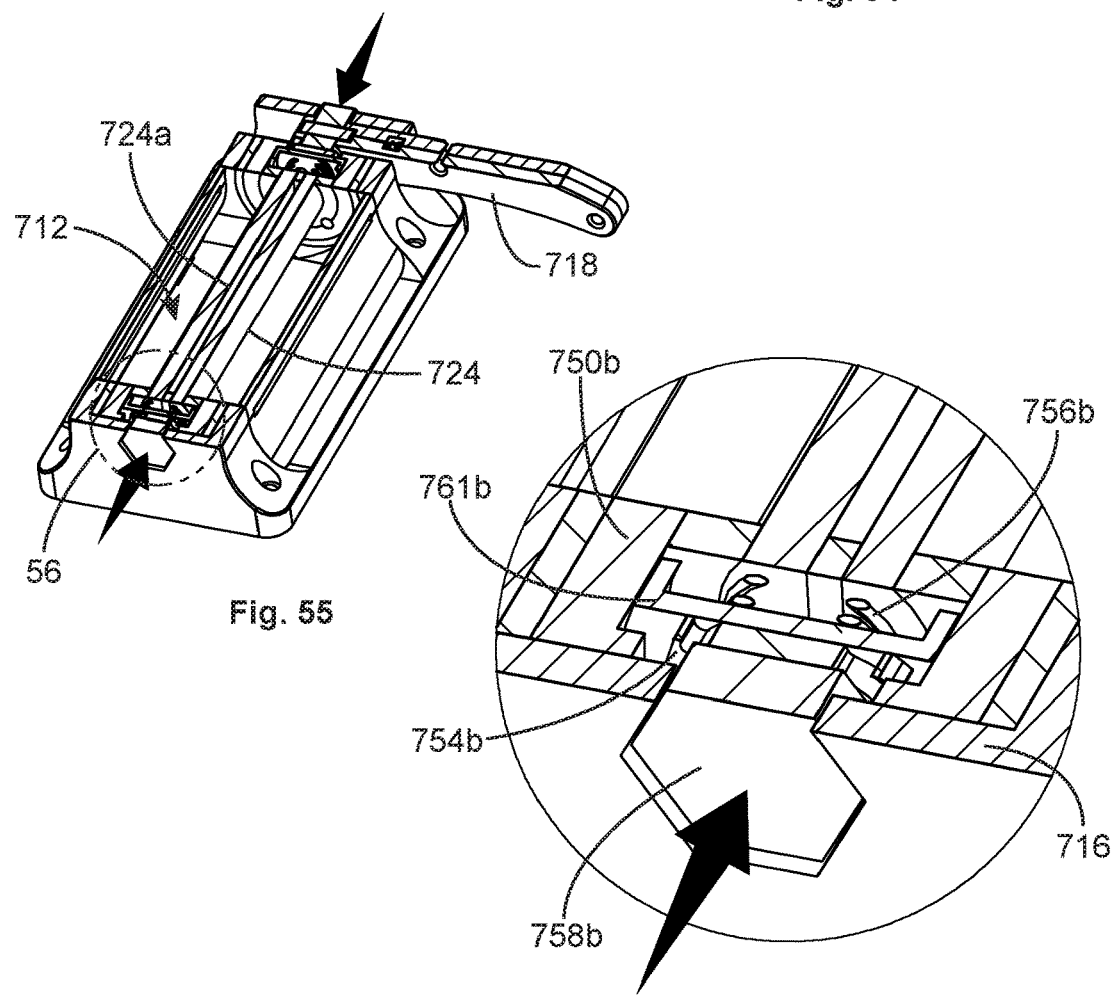
Fig. 55
Fig. 56

LEVER-OPERATED ADJUSTMENT DEVICES, FIT SYSTEMS, AND LINE TENSIONING SYSTEMS

This application is the National Stage of International Patent Application No. PCT/US2020/036324 filed on Jun. 5, 2020, which claims priority to U.S. Provisional Application 62/857,320 filed Jun. 5, 2019, and to U.S. Provisional Application 62/937,808 filed Nov. 20, 2019, the entire contents of which are hereby incorporated herein in their entireties.

BACKGROUND

1. Field

The present disclosure relates to low profile adjustment devices for use with various articles, fit system, and line tensioning systems.

2. State of the Art

How well a wearable article or device fits the body is highly important in the daily function of humans or even for animals. For example, wearable articles and devices can include, by way of example, garments, shoes, backpacks, sporting gear, wearable protective devices, sporting braces, orthosis, and/or prosthesis. Several factors can be weighed in how appropriate or satisfactory a wearable article or device fits the body, including whether the fit system transmits satisfactory load, provides satisfactory stability, suspends on the body, provides efficient congruency of the article or device during motion, provides sufficient mobility, is easily fitted, and/or is comfortable. These factors can be considered determinates in how appropriate or effective the fit of the article or device is on the body and they are directly related to how the article or device is secured or fastened to the body. Generally, the wearable articles or devices are secured to the body by tightening around the body. The mechanisms and associated methods of how articles or devices are secured to the body are hereby referred to as fit systems.

Fit systems and related devices and methods generally are operably attached to one or more flexible elongate members or tension lines (such as straps, cables, laces, etc.) with one or more attachment points or interfaces to the article or device. The attachment points or interfaces may decrease in distance relative to one another or relative to the fit system, which can be referred to as contraction or shortening. Such contraction can involve decreasing the effective length of the flexible elongate member(s) of the fit system and possibly increasing the amount of tension (or tensile loading) experienced by the flexible elongate member(s) of the fit system. Such contraction can occur when tightening or closing or other movement of the article or device with respect to the body. Alternatively, the attachment points or interfaces may increase in distance relative to one another or relative to the fit system, which can be referred to as extension or lengthening. Such extension can involve increasing the effective length of the flexible elongate member(s) of the fit system and possibly deceasing the amount of tension (or tensile loading) experienced by the flexible elongate member(s) of the fit system. Such extension can occur when loosening or other movement of the article or device with respect to the body.

The determinates of the appropriateness and effectiveness of a fit system may be associated with design elements of the fit system including: the mechanisms and associated methods for contraction and extension, the inherent mechanical advantage of a given fit system, mechanical reliability of the overall system and toughness of individual components, maximum load and tension, distance between the attachment points or interfaces in the maximum contracted and maximum extended positions, profile height of the fit system, width and length of the fit system, rigidity of the fit system and its components, whether the contraction and extension is incremental or analog in nature, how smooth or abrupt is the contraction and extension, attachment requirements of the fit system, system weight and suspension forces provided by the fit system, and pressure distribution of the fit system.

The mechanism/s and associated methods of use weigh heavily on the user experience of the fit system and is the driving factor for many of the other determinates of the fit system. For example, a mechanism may be mechanically effective but may have poor ergonomics. The mechanism may also affect the speed and direction of the contraction and extension. For example, the gear ratio mechanism within a fit system may provide high mechanical advantage, but a slow speed of contraction, which may be ideal for some applications and too slow for others. In another applications, the speeds of contraction and extension may be key for some applications. For example, certain military applications such as a fit system for a military aid pack or backpack may need to have a high speed of contraction and very high speed of extension such that the operator can quickly remove the pack if they need to quickly become mobile to avoid harm. In this application, a high mechanical advantage for contraction or extension may be less important because most users would have a relatively high level of strength. In still other applications, the direction of pull of the contraction or extension may be important. For example, contracting in a single direction could cause misalignment of a knee joint in an orthosis as the user tightens the brace onto their body. In these cases, a balanced, dual direction fit system would be more appropriate. How easily a fit system performs contraction and extension is paramount in its ability to deliver optimal fit and user experience. Many users of orthopedic devices have compromised strength and/or dexterity so mechanisms and methods that make the fit system easy for them to contract to the desired amount and easily extend for release is a huge need and large benefit. Conversely, if a fit system is so easily engaged for contraction or extension that it is accidentally triggered, that can be a serious functional problem as well. Mechanism and methods drive other factors such as the inherent mechanical advantage of the system and the increments of tightening. Some applications may require small increments of contraction or extension whereas others may be optimized by larger and therefore faster increments of change.

In addition, some mechanisms and methods of fit systems may allow for an opening or separation between attachment points or interfaces whereas others may be better suited or even require the fit system to remain as a single unit between attachment points or interfaces. Some applications may require that a fit system opens up in order to don and doff the device while others may not. For example, a leg brace may require that users open up the device in order to place their leg into the device whereas protective pants for motorcycle riders may allow for a waist fit system stay in one piece and loosen only while they pull it up to their waist.

The inherent mechanical advantage of a fit system is a byproduct of the mechanisms and the methods associated with the fit system. Such fit system can provide a quantifiable mechanical advantage ratio which is the amount of output force over the amount of input force. The speed or time needed to contract or extend the fit system a given distance is usually inversely correlated with mechanical advantage such that when mechanical advantage is high, speed is low and vice versa. Many applications differ in the mechanical advantage requirement, but most applications have a specific ratio or range of ratios that is optimal for function. If the mechanical advantage is too high or more than required for a given application, it may unnecessarily sacrifice speed. Mechanical advantage within a fit system directly relates to the maximum tension and load of the system. The maximum tension and load of a fit system is described in detail below.

The mechanical reliability and toughness of the fit system relates to the materials utilized by parts therein, geometry, dimensions, and manufacturing methods. Specifically, the overall fit system may only be as strong as its weakest link. Some parts can fail and cause catastrophic failure while others may not. Failure of some fit systems could lead to the users getting trapped or stuck in their device or with their device. In other situations, the user may be highly dependent on the device. Failure of a fit system could potentially even contribute to a fatal accident. Reliability is therefore extremely important especially in certain circumstances and applications.

Maximum tension of a fit system is typically dependent on the maximum tensile loading of the flexible elongate member(s) of the fit system. In many applications, the maximum tensile loading relates directly to the maximum input force multiplied by the mechanical advantage. The input force is most often the manual force of the user but may be the force imposed by another person or an electronic or other automated system. The input force is transferred to the fit system members via the mechanisms within the fit system which may or may not include mechanical advantage. The tensile loading of the flexible elongate member(s) of the fit system can transfer load or force onto the user's body. Generally, the load is directed into the body or, in other words, towards the center of the body's long axis or the long axis of a limb but may also be slightly oblique to the direction directly towards the long axis. If such loading forces are directed in an angle that is too oblique to the long axis they will likely cause the device to shift proximally or distally on the body unless counterbalanced by a geometric feature of the body or other feature. The amount of load transferred onto the body can also related to other factors. For example, the amount of body exposure from the device seen by the fit system will affect the how much of the tension force is transferred directly onto the body or into the device.

The loading directed into the body can apply pressure to the body. Generally, the pressure distribution applied to the body is dependent on the amount of loading applied by the fit system to the body divided by the surface area of the applied loading. Pressure distribution of the fit system is explained in further detail below. In many cases, the fit system can transfer some tension forces onto the device (for example, by the device changing shape or reducing in volume), thereby reducing load applied to the body. The amount of desired load or optimal load delivered onto the body by the fit system may differ per application, as the body changes, during activity changes, within certain movements, in certain positions, and/or over time. Although the optimal loads may vary per application and other variables, optimal performance is generally seen within a definitive range. The humans and animals generally prefer a similar range of load and associated pressure onto the body and within specific segments of the body. Beyond the level of preference, loads and pressures that are beyond a recommended range may cause a reduction in blood flow and/or other damage, discomfort, or pain. Conversely, if loads and pressures are too low, the device may fall down on the body or be loose on the body which may lead to damage, discomfort, or pain.

The maximum effective length of the flexible elongate members of the fit system can be referred to as the travel within a fit system. Travel within a fit system may relate to the amount of space available for a flexible elongate member to collect into the fit system or the distance of linear teeth in a ratchet ladder. The available amount of travel within a fit system may limit the amount of load that a fit system can deliver onto the body in that the maximum travel may be reached before the user gets to their desired amount of load onto the body. Travel may also directly affect device sizing in that a fit system with greater travel is likely to accommodate a wider range of body sizes and vice versa. These factors might suggest that fit systems should always include a maximum or large amount of travel. However, while increased travel may be beneficial, it often has a negative or inverse correlation on other determinates of the fit system such as the size, profile, weight, and other factors discussed below.

The profile height of the fit system is extremely important to product developers and end users. Profile height refers to the distance that the fit system protrudes away from the body or, in other words, how much it sticks out. Developers and end users have a strong preference or requirement for the fit system to have a low-profile for the aesthetic look and finish quality that they demand. Moreover, the profile height also plays a role in function and safety. If a fit system has a large profile height it will have a higher risk of catching on things or it may make it difficult or impossible to wear clothing over the fit system. Beyond these undesirable attributes, a fit system with a large profile can be a significant risk of injury due to the fact that if the user falls or bumps into something, the bulk of the fit system can be pushed into the body and can cause injury.

Similar to the profile height, the width and length of a fit system may also be important for applications of use. Width or length can limit applicability in some cases that may have a limited surface area of application. For example, shoes have a limited surface area that is acceptable for a fit system. Fit systems may be limited in their applicability to shoes if their width or length is over 45 mm or even 35 mm in some cases. However, beyond surface area limitations, larger width and length are far more acceptable for most applications fitting the body as compared to profile height.

In some cases, fit requirements can be very specific and a distance of one millimeter can be the difference in too loose and just right. In these cases, an analog fit system that can adjust in a continuous and controlled manor may be ideal. In other applications, incremental tightening provides the appropriate amount of fidelity while enabling for a wider array of fit system mechanisms. Incremental systems are often faster than analog systems that provide a control at a micro level. All incremental systems are not created equal. Some incremental fit system may offer small increments like 1.5 millimeters whereas others may offer large steps of 6 millimeters. Requirements for the distance between increments are specific per application but in general the range is between 0.5 mm and 8 mm. Regardless of whether a system is incremental or analog, the mechanism or method of use may provide a smooth transition as it is used to adjust fit or it may provide an abrupt experience. In general, the experience is understandably more favorable if it is more controlled and smoother. However, some cases require fast release or removal of a device.

Various fit systems have been proposed. An example of one such device is described in U.S. Pat. No. 9,867,430 (Boa Technologies). This prior art stacks fit system mechanisms and members vertically and thereby has a large profile height. The profile of commercial embodiments of this technology are relatively high in order to provide their respective mechanical advantage. Moreover, such profile heights for this technology are excessive for many applications. This commercial technology is also limited in mechanical reliability. The system utilizes cables or laces that are approximately 0.8 mm to 1.0 mm thick and can fail during use of many applications. Additionally, release is abrupt and may be shocking and jarring to the user. Moreover, users with poor hand dexterity lack the capacity to wind or release the tension line of the fit system.

Ratchet ladders have sufficient mechanical advantage for many applications, but the ladder strap teeth often cannot accommodate angles greater than 30 degrees without skipping. Additionally, release is abrupt and may be shocking and jarring to the user. Also, these systems are generally between 25 mm and 45 mm and are thereby excessively bulky in profile for many applications.

Ratchet straps offer large mechanical advantage and high mechanical reliability, however their profile height, difficulty and abruptness in releasing mechanisms, and challenge of donning wherein one needs to feed a strap through a split axis and hold the strap in tension in order to start it: all make for these systems to be inapplicable as a fit system.

Over-center cam buckles serve as fit systems for ski boots and other similar products. These fit systems and other similar products effectively provide mechanical advantage when they are attached to rigid plastic structures on both sides but they do not include fastening mechanism that allow them to mount to a strap and the base of the over-center cam would create high peak pressures if it were used on a loose strap due to its small base of support. The catch mechanisms for these devices are also not designed to work with a loose strap and create difficult ergonomics if they are used with loose straps. Moreover, these systems offer no security latch mechanisms to maintain the strap in the closed position, do not offer macro tightening and loosening, and are highly dependent on the specific geometry (angles and contours) of the application. All of these factors amount to over-center systems not being applicable to products fitting the body with the exception of products that include hard plastic rigid shells like ski boots.

Webbing straps with hook and loop fasteners (sold under the tradename VELCRO) is often used as a fit system in almost all devices that fit the body ranging from shoes to neck braces. The ubiquitous use of hook and loop systems may relate to its low cost, accessibility, low-profile, and ease in integration into product development; all fit system factors that affect a company's motivation to integrate a fit system into their product beyond the end user attributes discussed in detail above. Buckles, fasteners, and chafes are often utilized in combination with hook and loop fasteners in order to add some mechanical advantage and/or provide greater ease of use. Although hook and loop fasteners are widely used, end users often complain of the noise it makes during removal, how it often attaches to unintended materials and surfaces, how it collects lint, how it is difficult to tighten and loosen especially for those with low strength capacity, and how it tends to wear out with prolonged cycle use.

The most common fit system utilized for shoes is traditional laces. Laces offer minimal mechanical advantage but that is all that is needed in most shoes since the dorsum of the foot offers a large surface area to suspend on. Even though the need for mechanical advantage and suspension are low, fast, and ergonomic methods to tighten and loosen shoes is still desired.

Line tensioning systems and related methods can generally include one or more flexible elongate members (such as straps, cables, wires, etc.) with one or more attachment points or interfaces to an article, device, or structure. Similar to fit systems, the attachment points or interfaces may decrease in distance relative to one another or relative to the line tensioning system, which can be referred to as contraction or shortening. Such contraction can involve decreasing the effective length of the flexible elongate member(s) of the line tensioning system and possibly increasing the amount of tension (or tensile loading) experienced by the flexible elongate member(s) of the line tensioning system. Alternatively, the attachment points or interfaces may increase in distance relative to one another or relative to the line tensioning system, which can be referred to as extension or lengthening. Such extension can involve increasing the effective length of the flexible elongate member(s) of the line tensioning system and possibly deceasing the amount of tension (or tensile loading) experienced by the flexible elongate member(s) of the line tensioning system.

The determinates of the appropriateness and effectiveness of a line tensioning system may be associated with design elements of the line tensioning system including: the mechanisms and associated methods for contraction and extension, the inherent mechanical advantage of a given line tensioning system, mechanical reliability of the overall system and toughness of individual components, maximum load and tension, distance between the attachment points or interfaces in the maximum contracted and maximum extended positions, profile height of the line tensioning system, width and length of the line tensioning system, rigidity of the line tensioning system and its components, whether the contraction and extension is incremental or analog in nature, how smooth or abrupt is the contraction and extension, attachment requirements of the line tensioning system, system weight and suspension forces provided by the line tensioning system, and pressure distribution and loading provided by the line tensioning system.

SUMMARY

Lever-operated adjustment devices (such as for fit systems and line tensioning systems) are described herein that may be useful in a variety of applications, including for wearable articles and devices. The adjustment devices include a ratcheting lever operable to drive a spool for winding at least one flexible elongate member or tension line about the spool. The lever operated adjustment devices in accordance with this disclosure have relatively higher mechanical advantage and lower profile as compared to prior art devices. In addition, the lever-operated adjustment devices include a single-handed release mechanism that facilitates quick removal of tension in the at least one tension line.

In accordance with a first aspect, a lever-operated adjustment device includes a housing comprising a base having a lower surface extending in a plane and a cover coupled to the base. The device also includes a spool pivotally coupled to the base of housing and surrounded by the cover. The spool is configured to rotate about a first axis in a first rotational direction to wind the at least one tension line around the spool. The spool is also configured to rotate about the first axis in a second rotational direction (opposite the first rotational direction) to unwind the at least one tension line from the spool. The winding of the at least one tension line on the spool can provide for retraction of the adjustment device as part of a fit system or line tensioning system. The unwinding of the at least one tension line from the spool can provide for extension of the adjustment device as part of a fit system or line tensioning system. The first axis can be parallel to the plane of the lower surface of the base. The lever can be pivotally coupled to the housing and configured to rotate about a second axis, where the lever is operatively configured to drive the spool in the first direction to wind the at least one tension line around the spool.

The attachment device can also include a ratcheting adjustment mechanism that includes first and second engagement members supported by the housing and the lever. The first engagement member is operably coupled between the lever and the spool and has a coupled configuration that mechanically couples the lever to the spool such that pivoting motion of the lever drives the spool in the first rotational direction and prevents the spool from rotating in the second rotational direction. Also, the first engagement member has a decoupled configuration that mechanically decouples the lever from the spool.

The second engagement member is selectively coupled to the spool. The second engagement member has a coupled configuration that permits the spool to rotate in the first rotational direction while preventing the spool from rotating in the second rotational direction. Also, the second engagement member has a decoupled configuration that that mechanically decouples the second engagement member from the spool.

The release mechanism is configured to selectively release the spool by simultaneously configuring the first and second engagement members into their respective decoupled configurations. The operation of the release mechanism can be initiated by single hand movement of a user.

In embodiments, the release mechanism is configured to release the spool in response to a manual force applied to the device in a direction perpendicular to the first axis and parallel to a direction in which the tension line extends from the housing of the device. In embodiments, the release mechanism is configured to release the spool in response to a manual force applied to the device in a direction parallel to the first axis. In embodiments, the release mechanism is configured to release the spool in response to a pair of oppositely directed forces (e.g., parallel to the first axis of the spool) applied to the device.

In embodiments, the second axis can be parallel to the first axis. The second axis may be coaxial with the first axis.

In embodiments, the lever can be configured to translate relative to the housing and the spool in a first longitudinal direction parallel to the first axis to cause simultaneous disengagement of the first and second engagement members from the spool. The release mechanism can include a biasing member between the base and the lever that is configured to bias the lever in a second longitudinal direction opposite the first longitudinal direction.

In embodiments, the spool can be configured to translate relative to the housing and the lever in the first longitudinal direction parallel to the first axis. In embodiments, the spool can include an axle extending along the first axis as well as first and second driven gears fixed to the axle and spaced apart from one another along the axle. The first engagement member can include a driving gear configured to engage the first driven gear of the spool, and the second engagement member can include a ratchet gear configured to engage the second driven gear of the spool.

In embodiments, the first and second driven gears, the driving gear, and the ratchet gear can be side-facing gears having gear teeth extending in a direction parallel to the first axis. The driving gear, first and second driven gears, and the ratchet gear can be coaxially aligned with one another along the first axis. In embodiments, the first and second driven gears can have angled teeth with a drive side and a coast side, where the angle of the teeth of the first and second driven gears are oppositely arranged. In embodiments, the driving gear can be fixed or otherwise mechanically coupled to the lever, and the ratchet gear can be fixed or otherwise mechanically secured to the housing.

In embodiments, the axle can extend from a first end to a second end, and the lever extends in a u-shape across the axle from a first end at the first end of the axle to a second end at the second end of the axle. The first end of the lever defines a first hole configured to receive the first driven gear and the second end defines a second hole configured to receive the ratchet gear. A length measured along the first axis between bases of the first and second holes is larger, by a first predefined amount, than a length between the first driven gear and the ratchet gear.

In embodiments, the first end of the lever can define a first axle hole configured to receive the first end of the axle and the second end of the lever defines a second axle hole configured to receive the second end of the axle. A length measured along the first axis between bases of the first and second axle holes is larger, by a second predetermined amount, than a length between the first and second ends of the axle.

In embodiments, the axle can include a circumferential lip extending around the outer surface of the axle and positioned between the first and second driven gears and defining a first annular groove between the lip and the first driven gear. A width of the annular groove measured along the first axis can be at least equal to the first predetermined amount.

In embodiments, the attachment device can further include a fin extending between an outer surface of the axle and the base. The fin can be located at an intermediate position between the first and second driven gears. The fin can extend in a plane perpendicular to a plane in which a lower surface of the base extends. The fin can have a bearing surface that contacts and supports the axle.

In embodiments, the base can have a mounting flange for mounting the attachment device to a substrate, which can include part of a wearable article (e.g., a shoe) or other device as part of a fit system. In embodiments, the mounting flange can be configured to be sewn to the substrate. In other embodiments, the mounting flange can be configured to be mechanically connected to the substrate with snap-fit connection. In still other embodiments, the mounting flange can be configured to be mechanically connected to the substrate with adhesive.

In embodiments, the attachment device also includes a tension limiter coupled between the lever and the ratcheting adjustment mechanism.

In embodiments, the attachment device can have a mechanical advantage of over 2:1.

In embodiments, the housing defines two openings through which one or more tension lines may pass for support on the spool. The spool can be configured to draw the one or more tension lines onto the spool through the two openings. In other embodiments, the housing can define a single opening through which a tension line may pass for support on the spool. The spool can be configured to draw the tension line onto the spool through the single opening.

In embodiments, a preferred profile height may between 5 and 25 mm. If the profile height is under 5 mm, there is a risk of making sharp edges, and there is a risk that the device may become difficult to operate for people with poor dexterity or in applications requiring speed of use. Also, if the profile height is under 5 mm, the device may lack the strength needed for mechanical reliability. Profiles over 25 mm are beyond the point of being reasonable for most wearable applications aesthetically and my lead to safety hazards as discussed above. Nonetheless, in embodiments, the profile height may be up to 29 mm or more. In embodiments, the axle has a diameter of about 3 mm to about 5 mm.

In embodiments, the axle can be hollow. In other embodiments, the axle can be solid. In embodiments, the axle can define an elongated slotted opening to retain a flat strap tension line. In embodiments, the axle can define at least one hole configured to retain a cable or lace tension line having a round cross section.

In embodiments, the attachment device can include a pressure distribution pad in contact with the lower surface of the base. The pressure distribution pad can be configured to extend the area of base for pressure reduction.

BRIEF DESCRIPTION OF THE DRAWINGS

FIG. 39A is a transparent plan view of another embodiment of a tension device in accordance with an aspect of the disclosure.

FIG. 39B is a transparent side elevation view of the device shown in FIG. 39.

FIG. 40A is a transparent side elevation view of another embodiment of a tension device in accordance with an aspect of the disclosure.

FIG. 40B is a transparent plan view of the device shown in FIG. 39 shown with a tension line wound about an axle of the device.

FIG. 40C is a transparent plan view of the device shown in FIG. 39 shown with the tension line passing through the device and over the axle but now being wound about the axle.

FIG. 40D is a transparent side elevation view showing the lever being rotated and the resulting winding of the tension line about the axle.

FIGS. 41A-41C show details of a collection volume of an embodiment of a single action tension device in accordance with an aspect of the disclosure.

FIGS. 42A-42C show details of a collection volume of an embodiment of a single action tension device in accordance with an aspect of the disclosure.

FIG. 53 is a top, front, and side perspective view of another embodiment of a tension device.

FIG. 54 is a side elevation view of the device of FIG. 53.

FIG. 55 is a view of the device shown in FIG. 53 along line 55-55 in FIG. 54.

FIG. 56 is a detailed view of detail D in FIG. 55.

Prior Art

DETAILED DESCRIPTION

The present disclosure describes a number of embodiments of adjustment devices that employ a spool that interfaces to and supports at least one tension line. Thus, while some embodiments of the adjustment devices have been shown without connection to a tension line, all of the adjustment devices can be used with one or more tension lines. Note that each one the adjustment devices can be part of a fit system or a line tensioning system as described herein.

As used herein, a "tension line" refers to a flexible elongate member that can be gathered and wound onto a spool and unwound therefrom. The material of the tension line can be inelastic in nature or possibly have some elasticity. The tension line can be a cord, rope, cable, filament, or lace having a generally round profile, as well as flat straps having rectangular or square profiles. The material of the tension line can be any material typically used as a tension line in the same application. Thus, for a footwear application, the tension line used by the adjustment device in accordance with this description may be made from the same material currently in use for shoe laces. Also, the materials used may differ from those typically used for the application. The materials used for the tension line can include metal (e.g., steel) cable, and polyester webbing.

As used herein, a "fit system" refers to an adjustment device connected to a wearable article with at least one tension line (flexible elongate members such as straps, cables, wires, etc.) with one or more attachment points or interfaces to the article or device. The adjustment devices used in fit systems As used herein, a "line tensioning system" refers to an adjustment device connected to a non-wearable article or structure with at least one tension line (flexible elongate members such as straps, cables, wires, etc.) with one or more attachment points or interfaces to the article, device, or structure. Similar to fit systems, the attachment points or interfaces may decrease in distance relative to one another or relative to the line tensioning system, which can be referred to as contraction or shortening. The adjustment devices used in line tensioning systems may operate in space without being directly mounted to an article or structure.

Figure 1:
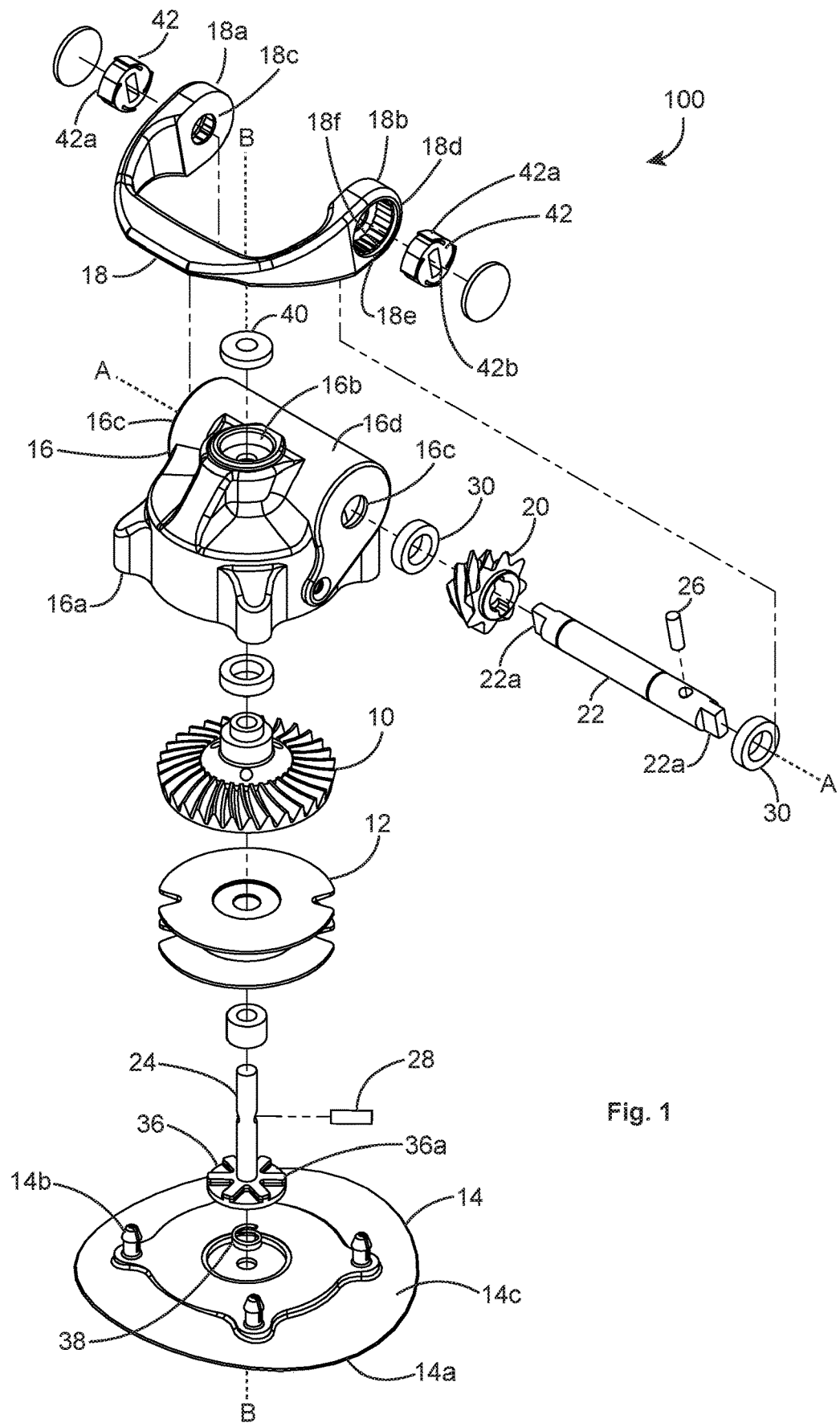
FIG. 1 is an assembly view of a first embodiment of a lever-operated fit device in accordance with an aspect of the disclosure.
Figure 2:
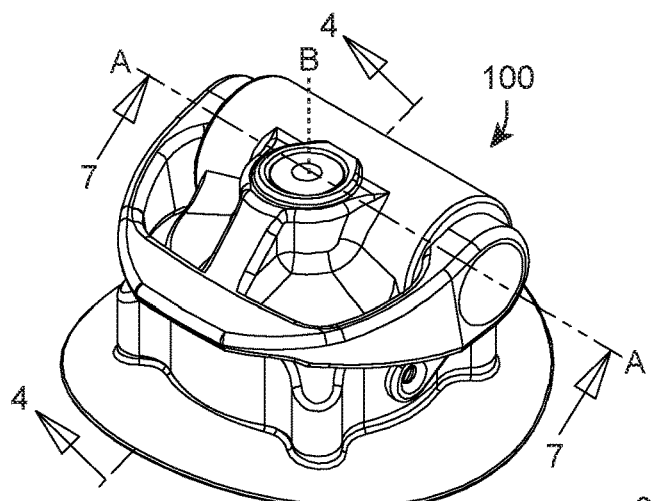
FIG. 2 is a front, side, and top perspective view of the device of FIG. 1A in an assembled condition.

FIGS. 1 to 11 show details of an adjustment device 100 that incorporates a hypoid gear 10 to drive a tension line spool 12 configured to wind a tension line (not shown) about the spool 12. As shown in FIG. 1, the attachment device 100 includes a base 14 and a cover 16, which when connected together to form a housing. The system 100 also includes a winding lever 18, a driving gear 20, and a driving axle 22. The cover 16 includes a top cage portion 16*d* that receives and houses the driving axle 22 for orientation along an axis A-A. The driving gear 20 is fixed to the driving axle 22 with a pin 26. The top cage portion 16*d* of the cover 16 permits the assembly of the driving axle 22 and gear 20 with the lever 18. The lever 18 is mechanically coupled to the driving axle 22 and the driving gear 20 such that manual pivoting motion of the lever 18 about the axis A-A drives rotation of the driving axle 22 and the driving gear 20 about the axis A-A.

The system 100 also includes the driven hypoid gear 10 and tension line spool 12 which are supported by a driven axle 24 that is pivotally coupled to the cover 16. The hypoid gear 10 is fixed to the driven axle 24 with a pin 28. The adjustment device 100 is shown fully assembled in FIG. 2 with the lever 18 shown in a first position in which the lever 18 is fully folded in an initial or rest position relative to the cover 16.

The driving axle 22 extends along the axis A-A through the center of the driving gear 20. The axis A-A extends parallel to a plane in which a lower surface 14*a* of the base 14 extends. Due to the fixation of the driving gear 20 to the driving axle 22, the driving axle 22 and the driving gear 20 rotate together in unison about the axis A-A. The driven axle 24 extends along an axis B-B that is perpendicular to the axis A-A. The driven axle 24 extends coaxially through the center of the hypoid gear 10. Due to the fixation of the hypoid gear 10 to the driven axle 24, the driven axle 24 and the hypoid gear 10 rotate together in unison about the axis B-B. The hypoid (driven) gear 10 is fixed to the driven axle 24 at a position that ensures that the driving gear 20 remains enmeshed or otherwise engaged with the hypoid gear 10 at all times.

Figure 3:
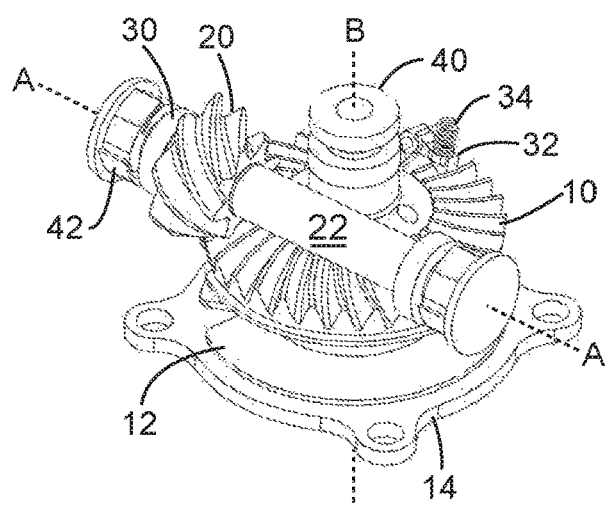
FIG. 3 shows the device of FIG. 2 with a cover of the device omitted to show detail of a hypoid gear mechanism.
Figure 4:
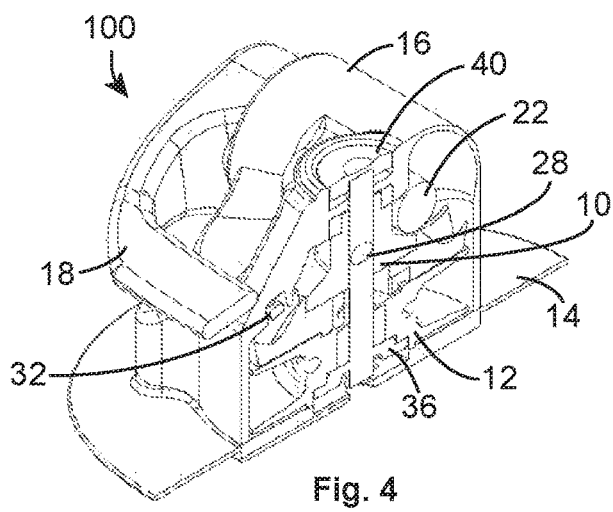
FIG. 4 is view of the device of FIG. 2 along line 4-4 in FIG. 2.
Figure 5:
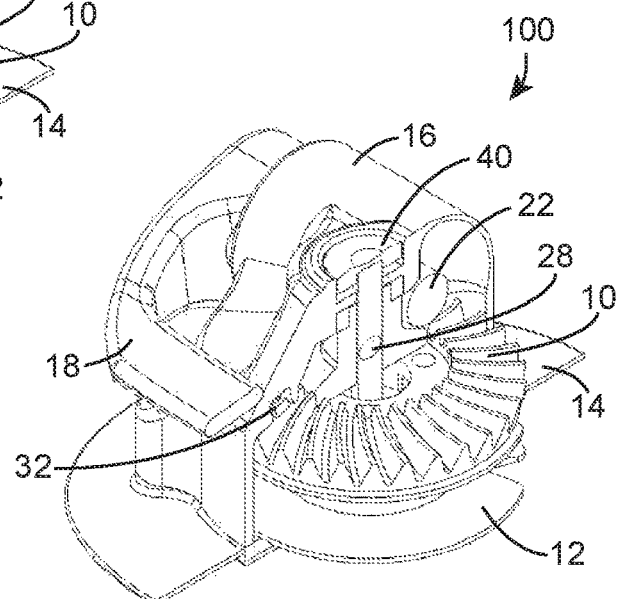
FIG. 5 is a partial cutaway view of the device of FIG. 2 along line 4-4 in FIG. 2.
Figure 8:
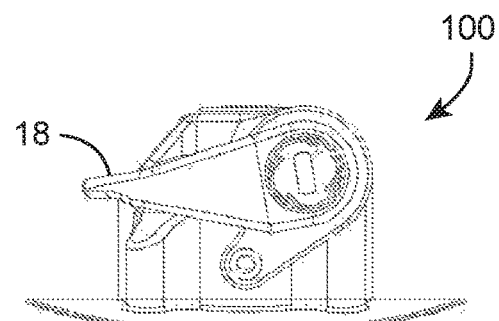
FIG. 8 is a side view of the device of FIG. 2 with the lever in a first, rest position.
Figure 6:
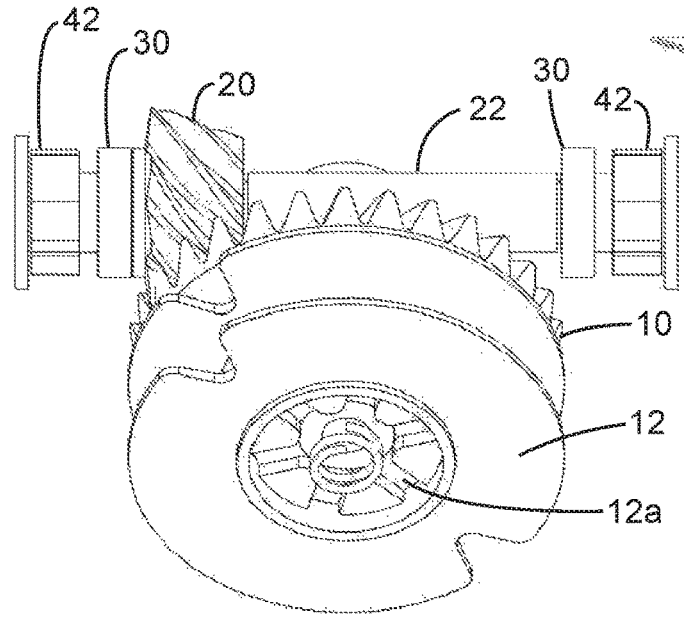
FIG. 6 is a bottom and side perspective view of a portion of the hypoid gear mechanism shown in FIG. 3.
Figure 9:
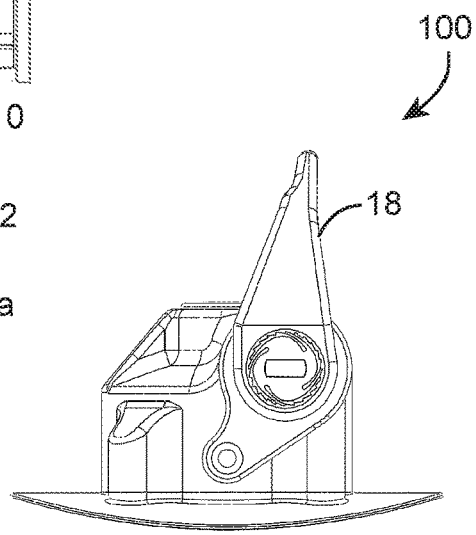
FIG. 9 shows the device of FIG. 8 with the lever rotated from the first position to a second position in a first advancing direction.

As shown in greater detail in FIG. 3, the axes A-A and B-B do not intersect one another, but are positioned in spaced relation to one another to position the teeth of the driving gear 20 and the hypoid gear 10 into meshed engagement. The driving gear 20 has helical teeth that are configured to always be enmeshed with teeth of the hypoid gear 10. The driving gear 20 is configured to rotate about the axis A-A to drive rotation of the hypoid gear 10 about the axis B-B in a first rotational direction.

The driven axle 24 (and its rotational axis B-B) also extends coaxially through the center of the spool 12. The spool 12 is not directly secured to the driven axle 24. Instead, the spool 12 can be selectively and indirectly coupled to the driven axle 24 with an engagement member 36 that is fixed to a lower end of the driven axle 24. When the engagement member 36 is configured to couple the spool 12 to the driven axle 24, the spool 12 rotates in unison with the rotation of the driven axle 24 (and also in unison with the rotation of the hypoid gear 10 coupled thereto). In this manner, the engagement member 36 is configured to selectively engage and join the spool 12 to the driven axle 24 to prevent relative rotation between the driven axle 24 and the spool 12. Specifically, the engagement member 36 can have protrusions or teeth 36*a* and the spool 12 has corresponding recesses or teeth 12*a* (FIG. 6) that are configured to mate with the protrusions or teeth 36*a* of the engagement member 36 in a first configuration of the engagement member 36. A biasing member 38 (e.g., a spring) is engaged between the bottom of the engagement member 38 and the top of the base 14. The biasing member 38 biases the engagement member 36 (and thus the driven axle 24) upwardly so that the protrusions or teeth 36*a* of the engagement member 36 are engaged with the recesses or teeth 12*a* of the spool 12. The biasing member 38 also translates the spool 12 axially upward into contact with an underside of the hypoid gear 10 so that the spool 12 will not move axially out of engagement with the engagement member 36.

The cover 16 defines a central opening 16*b* aligned with the axis B-B. The central opening 16*b* is coaxial with the driven axle 24, the spool 12, and the hypoid gear 10. The cover 16 also defines opposed openings 16*c* in sides of the cover that align with the axis A-A. The side openings 16*c* are coaxial with the driving axle 22 and the driving gear 20. The driving axle 22 extends along the axis A-A and has ends 22*a* that extend through the side openings 16*c* of the cover 16. The driving axle 22 is supported near its ends by bearings 30 seated in grooves (not shown) formed in the wall of the cover adjacent the side openings 16*c* of the cover 16.

The driven axle 24 extends through the opening in the top of the cover 16. A push button 40 is attached to the upper end of the driven axle 24. The engagement member 36 can be disengaged from the spool 12 by translating the driven axle 24 along axis B-B in the downward direction by depressing the push button 40. When the push button 40 is not depressed, the engagement member 36 remains engaged with the spool 12 in the first configuration so that the spool is rotationally fixed to the driven axle 24. Also, since the hypoid gear 10 is rotationally fixed to the driven axle 24 with the pin 28, rotation of the hypoid gear 10 directly causes the driven axle 24 to rotate in unison with the hypoid gear 10. Thus, rotation of the hypoid gear 10 about the axis B-B in a first rotational direction causes rotation of the spool 12 in the first rotational direction when the spool 12 is engaged with the engagement member 36. However, if the push button 40 is depressed to disengage the spool 12 from the engagement member 36 in a second configuration, rotation of the hypoid gear 10 will not cause the spool 12 to rotate in the first direction in unison with the hypoid gear 10 and the driven axle 24, since the spool 12 is disengaged from the driven axle 24 permitting relative rotation between the driven axle 24 and the spool 12. Thus, when the spool is in the second configuration, the spool 12 rotates freely in either of the first direction or a second direction opposite the first direction, which can allow a user to unwind tension line from the spool 12, either partially or fully as long as the button 40 remains depressed. Once a user releases the button 40, the spring 38 will reconfigure the spool 12 into the first configuration so that the spool 12 can only be rotated with the shaft in the first direction to wind the tension line.

Figure 7:
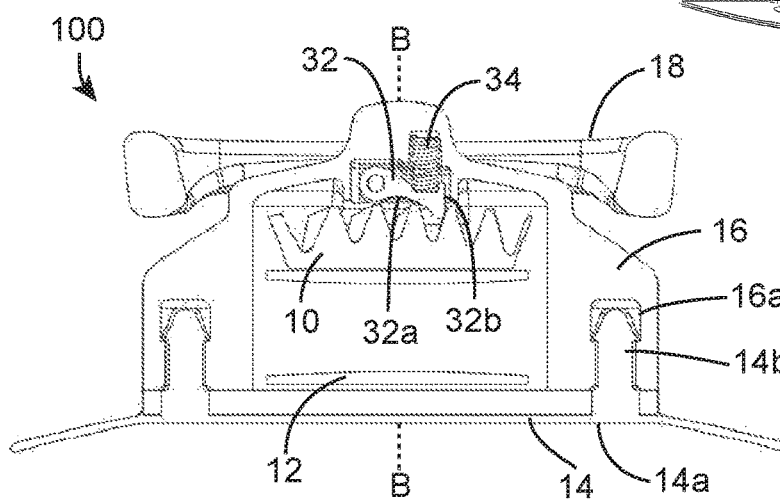
FIG. 7 is view of the device of FIG. 2 along line 7-7 in FIG. 2.
Figure 10:
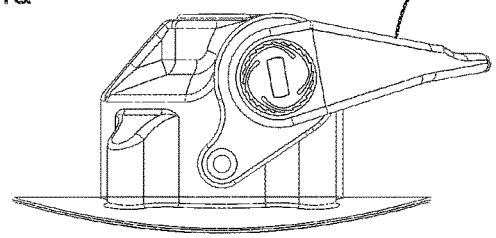
FIG. 10 shows the device of FIG. 8 with the lever rotated further in the first winding direction from the second position to a third position.

As shown in greater detail in FIG. 7, a pawl 32, resiliently biased with spring 34, is pivotally coupled to an underside of the cover 16. The pawl 32 has a curved underside 32*a* that is configured to allow the pawl 32 to ride over the teeth of the hypoid gear 10 when the hypoid gear 10 rotates about the axis B-B in a first advancing direction (to the right in FIG. 7). The pawl 32 has a sharp distal edge 32*b* that is angled to fit between adjacent teeth of the hypoid gear 10, which prevents rotation of the hypoid gear 10 in a second direction (to the left in FIG. 7) opposite the first direction. The spring 34 maintains engagement between the pawl 32 and the teeth of the hypoid gear 10. Thus, the pawl 32 aids in maintaining tension in the tension line during winding by preventing the hypoid gear 10 (and also the engaged spool 12) from reversing direction.

Rotation of the hypoid gear 10 is accomplished by driving (rotating) the driving gear 20 using the lever 18. The lever 18 is connected to the driving axle 22 at spaced apart regions thereof and preferably at opposing ends thereof. The lever 18 is shown u-shaped for convenience of use but can be of other shapes. The lever 18 has openings 18*c*, 18*d* at its ends 18*a*, 18*b* that are aligned along the axis A-A. The inner surface (e.g., 18*e* is shown and is the mirror image for opening 18*c*) of the openings 18*c*, 18*d* are circular and define a plurality of teeth 18*f* equally spaced circumferentially. The teeth 18*f* are rounded one-way slopping gear teeth (gear teeth with a coast side and a drive side). Each opening 18*c*, 18*d* is configured to receive a corresponding ratcheting pawl member 42 that has pawls 42*a* that engage and are driven by the drive side of the teeth on the inner surface 18*e* of the openings 18*c*, 18*d* when lever 18 is rotated a first direction (i.e., clockwise in FIG. 1) about axis A-A. Otherwise, if the lever 18 is rotated in a second direction about axis A-A opposite the first direction (i.e., counter-clockwise in FIG. 1), the coast side of the gear teeth 18*f* ride or skip over the pawls 42*a* allowing for a ratcheting operation of the lever 18. Each pawl member 42 defines a central through hole 42*b* that is keyed or otherwise shaped to fit a mating end 22*a* of the driving axle 22. Thus, when the pawls 42*a*, 42*b* are engaged when the lever 18 rotates in the first direction about axis A-A, the driving shaft 22 and driving gear 20 rotate together in unison with the pawl members 42 and the lever 18 about axis A-A. Further, since the driving gear 20 is enmeshed with the hypoid gear 10 at all times, the rotation of the driving gear 20 causes rotation of the hypoid gear 10 about the axis B-B, which thereby causes the engaged spool 12 to rotate in the first rotational direction about axis B-B. Any tension line connected to the spool will be drawn toward and wound around the spool 12.

Once the spool 12 has been wound to tighten the tension line to a desired amount by the user, or if the lever 18 cannot be rotated any further (i.e., because a portion of the article coupled to the adjustment device 100 interferes with the lever 18 or the volume between the spool 12 and the housing 16 is full of tension line), further rotation of the lever 18 in the first direction about axis A-A stops and the pawl 32 locks the hypoid gear 10 from unwinding in the second direction about axis B-B. The lever 18 can then be rotated about axis A-A in a second direction back toward the first rest position (i.e., counterclockwise). As the lever 18 is rotated about axis A-A in the second direction back toward the first rest position, the coast side of the inner teeth of the lever 18 ride over the pawls 42*a* as the pawl member 42 and the driving axle 22 remain rotationally stationary relative to the cover 16 due to the locked position of the hypoid gear 10 enmeshed with the driving gear 20. Thus, the pawl members 32 and 42 permit a one-way winding of the spool 12 and a ratcheting operation of the lever 18. Additional rotation of the spool 12 in the first rotational direction about axis B-B to wind additional tension line can be accomplished by repeating the rotation of the lever 18 about its pivot axis A-A back and forth as many times as desired to achieve the desired tension in the tension line and/or desired amount of tension line collected Any tension in the tension line connected to the spool 12 can be reduced by disengaging the spool 12 from the engagement member 36 by depressing the push button 40, which permits the spool 12 to rotate relative to the driven axle 24 and the hypoid gear 10 in the second direction about axis B-B opposite the first direction to loosen the tension line. Once the spool 12 is disengaged, the spool 12 is free to rotate in the second direction opposite the first direction to pay out tension line to reduce tension.

The cover 16 and the base 14 are removably coupled together to form a housing. In the embodiment shown, the base 14 includes snap fit connectors 14*b* formed as projections that are configured to snap into recesses 16*a* (FIG. 7) formed in the underside of the cover 16 to join the cover to the base. Other coupling arrangements are contemplated, including threaded fasteners and other snap fit arrangements. The base 14 has a flange 14*c* that may be formed as a flexible material, such as plastic or durable fabric that can be sewn to an article, such as a wearable article (e.g., shoes, belts, straps, helmets). Alternatively, the flange 14c may be adhesively connected along its lower surface 14a to an article. Also, a portion of an article may be coupled between the cover and the base 14 using the snap fit connectors 14b as both a means of coupling the base 14 to the cover 16, but also as a means of interconnecting the article between the base 14 and cover 16. For example, an article may have a mounting flange having four holes formed that match the pattern of the four projections 14b in the base 16 to permit the projections 14b to pass through the holes in the flange of the article and to then snap into the recesses 16a of the cover, thereby locking the article between the base 14 and the cover 16.

Figures 11, 12, 13, 14:
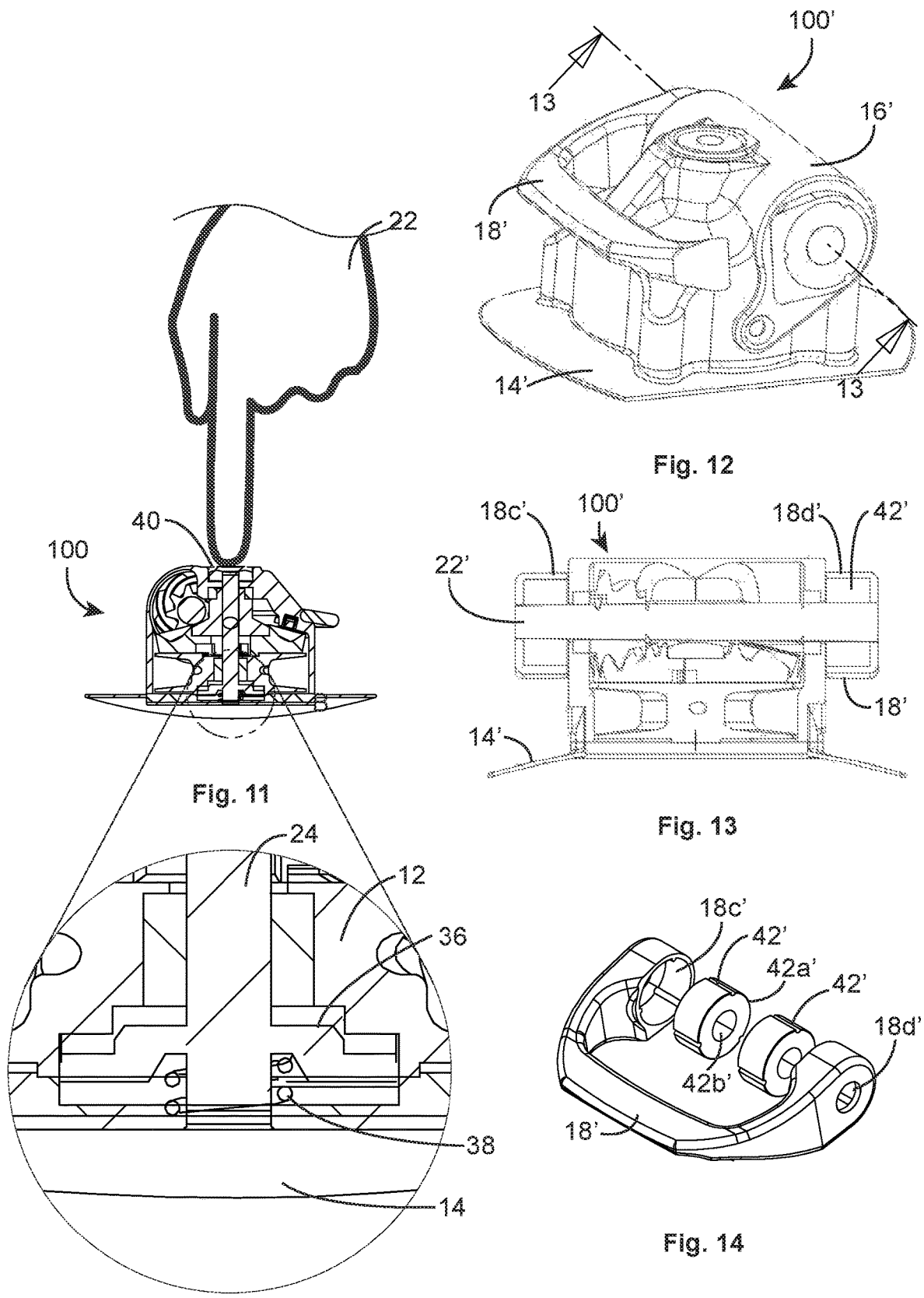
FIG. 11 shows details of a user hand movement to disengage and release the spool to permit the spool to rotate in a reverse direction to unwind tension line.
FIG. 12 is a perspective view of an alternate embodiment of the device of FIG. 1 with a portion of the side of the device removed to show detail of connection between the lever and housing of the device.
FIG. 13 is a view of the device of FIG. 12 along line 13-13 in FIG. 12.
FIG. 14 is an assembly drawing of the lever and one-way bearings used in the device shown in FIG. 12.

FIGS. 12-14 show an alternative adjustment device 100' to the adjustment device 100. In FIGS. 12-14, elements corresponding to adjustment device 100 are referenced with like reference numbers appended with "'". Specifically, adjustment device 100' differs from adjustment device 100 as follows. The adjustment device 100' includes one-way bearings 42' as a substitute for pawl members 42 and the inner gear teeth 18f of lever 18. In adjustment device 100', the lever 18' has inner openings (opening facing the center of the housing 16') 18c', 18d' formed in the ends 18a', 18b' of the lever 18' that are keyed to receive outer race 42a' of one-way bearings 42'. The outer race 42a' of the bearings 42' are keyed with grooves to mate with corresponding protrusions in the openings 18c', 18d' to prevent relative rotation between the outer race 42a' and the lever 18'. A driving axle 22' is received and rotationally fixed to inner races 42b' of the bearings 42'. The operation of the lever 18' to drive and rotate the spool 12' about axis B-B is the same as in device 100, however the one-way winding function provided by the pawl members 42 and inner teeth 18f are provided by an internal mechanism of the one-way bearings 42', as is known in the art.

Figure 15:
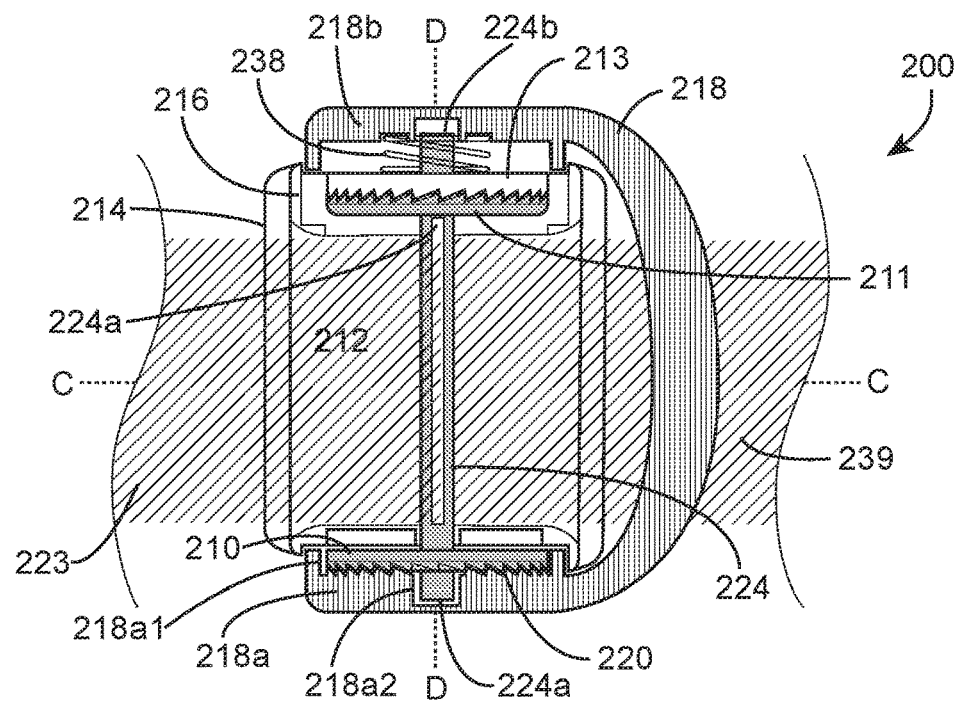
FIG. 15 shows another embodiment of an adjustment device in accordance with an aspect of the disclosure.
Figure 16:
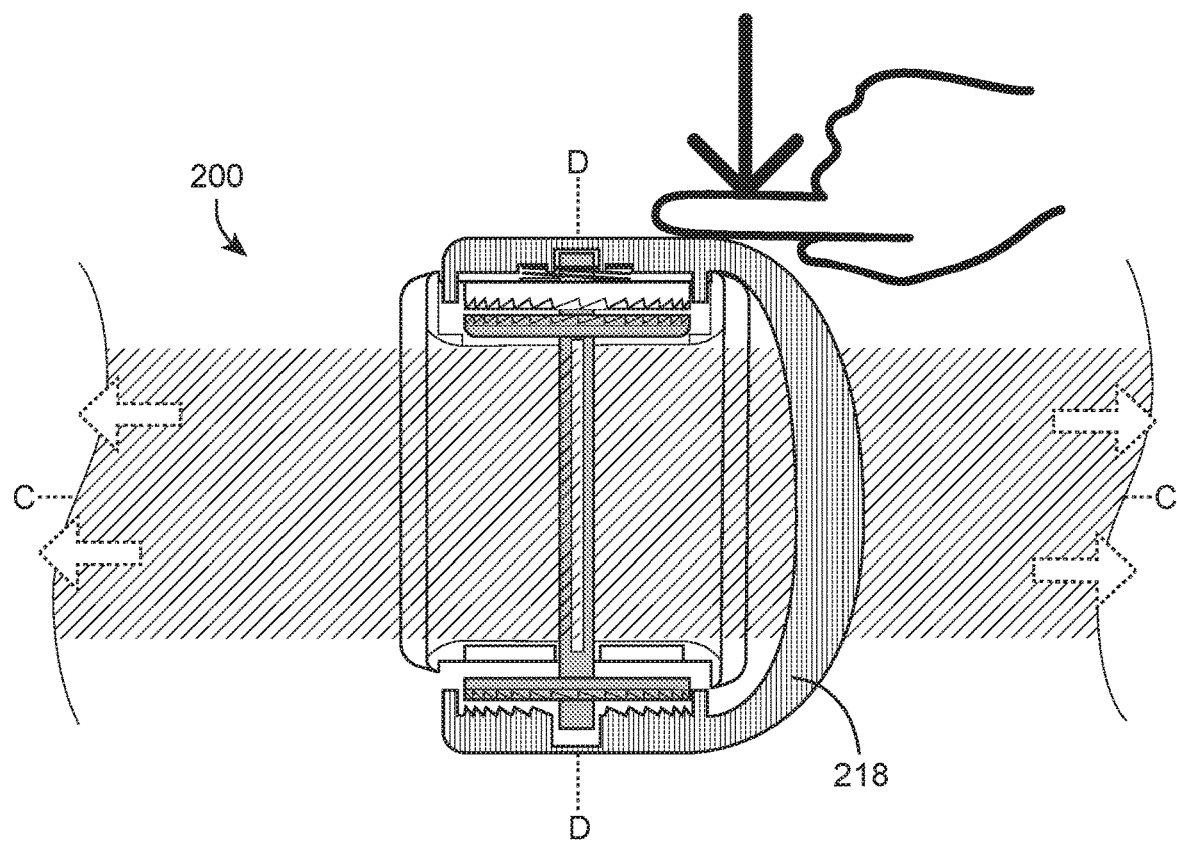
FIG. 16 shows a method of manually operating a release mechanism of the device of FIG. 15 to release tension in a tension line connected to a spool of the device.
Figure 17:
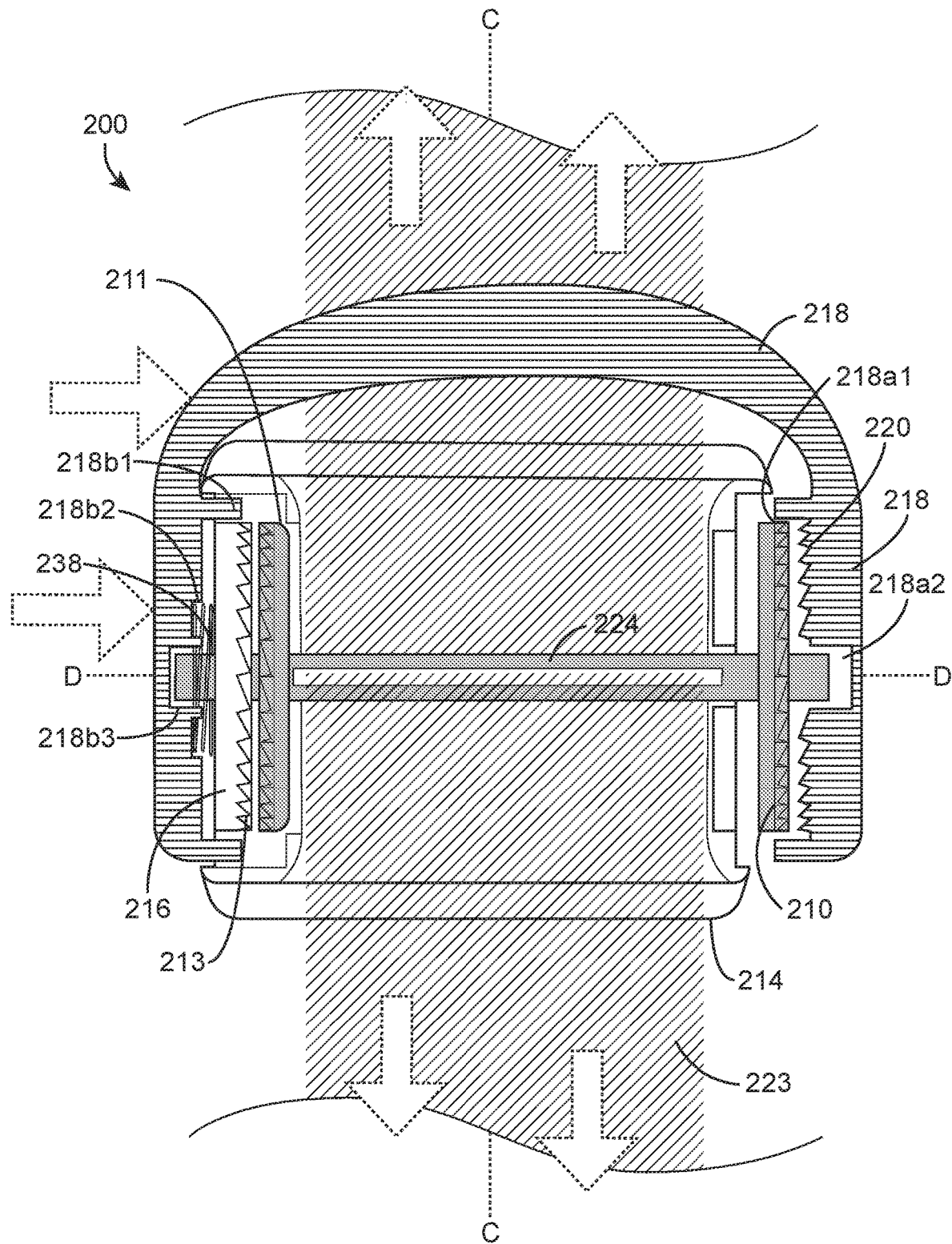
FIG. 17 is an enlarged view of the device shown in the released configuration shown in FIG. 16.

FIGS. 15-17 show another embodiment of an adjustment device 200 with dual-direction adjustment (the device has pathways to wind the strap from two different directions, e.g., left, and right in FIG. 15). As shown in FIG. 15, the device 200 includes a base 214 with a ratchet gear 213, a cover 216 (shown transparent in FIG. 15) or housing connected to the base 214, a winding lever 218 having a side-facing driving gear 220, and a driven axle 224 connected to a first driven gear 210 and a second driven gear 211 forming a winding spool 212 for winding a tension line 223 (e.g., a strap). The driven axle 224 extends from a first end 224a to a second end 224b. The first and second driven gears 210 and 211 are fixed to the driven axle 224 and rotate in unison together with the axle 224 coaxially about a central axis of the axle D-D, that extends perpendicular to axis C-C. The first driven gear 210 and the second driven gear 211 are located at intermediate positions between the first and second ends 224a, 224b of the driven axle 224. Thus, the driven gear 210 is spaced from the first end 224a of the axle 224 and the second driven gear 211 is spaced from the second end 224b of the axle 224.

The adjustment device 200 is shown fully assembled in FIG. 15 with the lever 218 shown in a first position in which the lever 218 is fully folded in an initial or home position relative to the base 214. The driven axle 224 has a longitudinal split opening 224a to receive a tension line 223 (e.g., a strap) therethrough. The split opening 224a can be pinched to close on the strap 223 to retain the strap relative to the axle 224.

The driving gear 220, driven gears 210, 211, and ratchet gear 213 have side-oriented teeth that extend generally parallel to the longitudinal axis D-D. The driving gear 220 and first driven gear 210 have gear teeth have oppositely sloping coasting surfaces and driving surfaces compared to the gear teeth of the second driven gear 211 and ratchet gear 213. The coasting surfaces extend at an acute angle with respect to the axis C-C. The driving surfaces extend substantially (within about 15 degrees) parallel to the longitudinal axis D-D. The side-facing orientation of the gear teeth differ from prior art gears that have gear teeth that extend radially outward in a direction perpendicular to the axis of rotation of the gear. The side facing gears 220, 210, 211, and 213 used in the adjustment device 200 allow for a lower profile and compact design as compared to what would be required using prior art gear arrangements.

The adjustment device 200 also includes the u-shaped lever 218 that extend from a first end 218a to a second end 218b. The first end 218a has a first bore 218a1 in which the side-oriented driving gear 220 is recessed. The driving gear 220 is configured to engage and drive the first driven gear 210 of the spool 212. The first end 218a also has a second bore 218a2 configured to receive the first end 224a of the driven axle 224. The second end 218b has a first bore 218b1 coaxially aligned with the driven axle 224 and configured to receive the ratchet gear 213. The second end 218b also defines a second bore 218b2 formed as a shallow spring seat in the base of the first bore 218b1 to receive a spring 238 extending between the spring seat 218b2 and an outer side of the ratchet gear 213, which is an outer side of the cover 216. A third bore 218b3 is defined in the base of the second bore 218b2 that is configured to receive the second end 224b of the driven axle 224.

The ratchet gear 213 is fixed on the inside of the cover 216 and is configured to mesh with the second driven gear 211. The spring 238 biases the entire lever 218 axially along axis D-D in a direction toward the ratchet gear 213 so that the driving gear 220 is engaged with the first driven gear 210 and the second driven gear 211 is engaged with the ratchet gear 213. When the lever is rotated from the first position in the direction of the curved arrow about axis D-D, the driving gear 220 drives the first driven gear 210 in the same direction. The entire spool 212 rotates with the first driven gear 210 to wind the tension line 223 in the direction of the opposing arrows. Also, when the lever rotates in the first direction about axis D-D, the coast side of the teeth of the second driven gear 211 skip over the coast side of the teeth of the ratchet gear 213. When lever 218 and the driving gear 220 rotates in a second direction about axis D-D opposite the first direction, the coast side of the teeth of the driving gear 220 skip over the coast side of the teeth of the first driven gear 210 so that the tension line 223 is not unwound. Also, when the lever 218 is rotated in the second direction, the drive side of the gears of the ratchet gear 213 and the second driven gear 211 engage to prevent the axle 224 from rotating in the second direction about axis D-D. This allows the lever 218 to reset back to the first position without reducing the tension in the tension line 223.

As shown in FIGS. 16 and 17, the entire lever 218 can be translated along axis D-D relative to the base 214 and the cover 216 to simultaneously disengage the driving gear 220 from the first driven gear 210 and to disengage the second driven gear 211 from the ratchet gear 213. Such disengagement permits the spool to rotate in the second direction about axis D-D to unwind the tension line 223. Specifically, FIG. 16 shows a method of releasing the tension in the tension line by way of pressing on the lever with a finger or hand of a user to impart a force on the lever 218 at least partly in a direction of the arrow, which is in a direction parallel to the axis D-D. When the lever 218 translates, the spring 238 becomes compressed as the second end 224b of the axle 224 is received in the third bore 218b3 and the ratchet gear 213 is received in the first bore 218b2. Also, when lever 218 is translated, the first end 224a of the axle 224 slides in a direction away from a bottom of the second bore 218a2 as the first driven gear 210 moves out of engagement with the driving gear 220 and out of the first bore 218a1 of the first end 218a of the lever 218. This release of the spool 212 from engagement with the driving gear 220 and the ratchet gear 213 is made possible by the spaces of the first bores 218a1, 218b1 of the lever 218 that are specifically designed to allow the lever 218 to translate relative to the spool 212. Upon release of the lever 218 in FIG. 16, the spring 238 will push the driving gear 220 into engagement with driven gear 210 and push the driven gear 211 into engagement with ratchet gear 213 (as shown in FIG. 15).

FIGS. 18-32 show an alternate adjustment device 300 to that shown in FIGS. 15-17 and described above. In FIGS. 18-32 like elements to those of device 200 will be referred to with like numbers incremented by "100". The adjustment device 300 has corresponding elements and function as the device 200 described above but has the following additional features.

Figure 18:
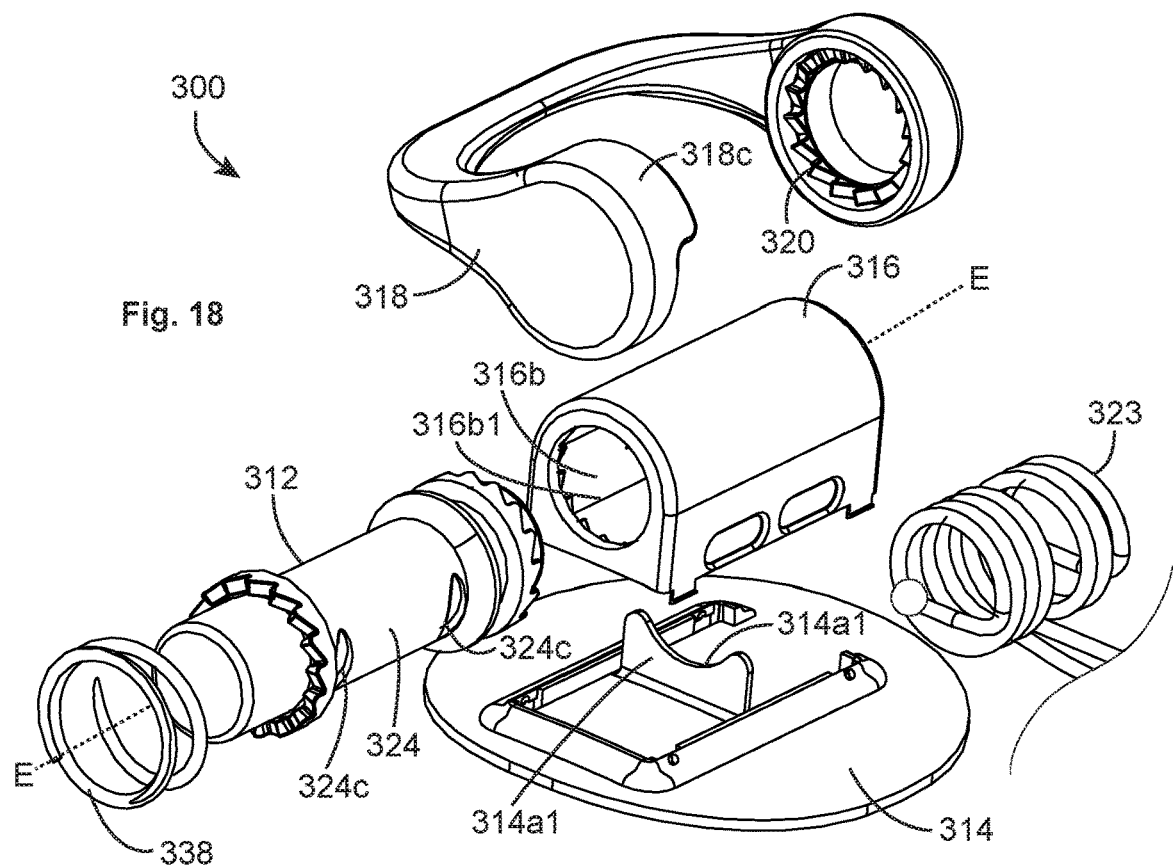
FIG. 18 is an assembly drawing of another embodiment of an adjustment device in accordance with an aspect of the disclosure, viewed from a rear, top, and side of the device.
Figure 19:
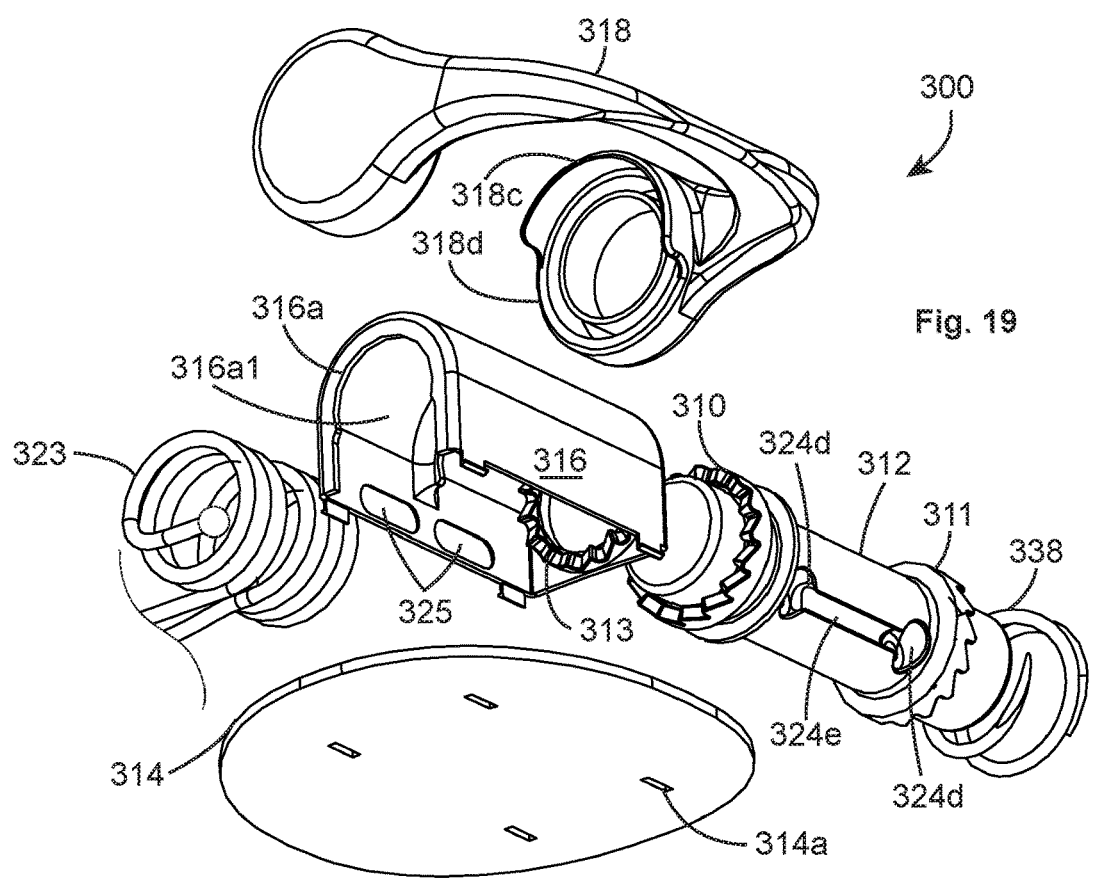
FIG. 19 is an assembly drawing of the device of FIG. 18 viewed from a front, bottom, and side of the device.

As shown in FIGS. 18 and 19, the device 300 includes a base 314 and a cover 316 that connect together form a housing to house the spool 312 and tension line in a generally annular collection volume between the outer surface of the axle 324 of the spool 312 and the inner surfaces of the base 314 and the cover 316. The base 314 may be connected to the cover 316 with a snap fit connection or with other fasteners, such as threaded fasteners.

The cover 316 extends longitudinally along axis E-E from a first open end 316a to a second open end 316b. The cover 316 defines a u-shaped hole 316a1 at the first end of the cover 316a and a circular hole 316b1 at the second end 316b of the cover. The u-shaped hole 316a1 and the circular hole 316b1 have smooth mating and bearing surfaces for supporting the first and second ends 324a, 324b of the driven axle 324, which extends coaxially with the cover 316 along axis E-E. The u-shaped hole 316a1 provides an opening at the bottom of the cover 316 that allows the first end 324a of the driven axle 324 to be assembled into the cover 316 after a tension line 323 (e.g., lace or cable) has been joined to the axle 324. The second end 324b of the driven axle 324 extends through the circular hole 316b1. Like the device 200, a ratchet gear 313 with side-facing teeth (facing the first end 316a of the cover 316) is located on an inner side wall of the cover 316 at the second end 316b of the cover 316. The ratchet gear 313 is configured to engage the second driven gear 311 of the spool 312 when the spool 312 is assembled between with the base 314 and the cover 316.

The base 314 is has a generally planar bottom surface 314a (FIG. 19) and top surface. The lower surface 314a of the base 314 extends in a plane parallel to the axis E-E of the axle 324. The base 314 has a peripheral flange 314c that can serve as a stitch flange wherein the stitching flange can be integrated into an article, such as a garment.

The base 314 includes a central fin 314a or wall that extends perpendicular to the bottom surface 314a of the base 314. The fin 314a also extends perpendicular to the longitudinal axis E-E of the axle 324. The cover 316 may also include a central fin that aligns with the fin 314a of the base 314. The fin 314a has a semicircular cutout 314a1 that is configured to engage and bear against a lower half of the outer surface of the axle 324. The cutout 314a1 matches the contour of the profile of the driven axle 324. Thus, when the device 300 is assembled, the fin 314a1 at least partially surrounds the outer circumference of the axle 324 to thereby divide the annular collection volume into two parts. The fin 314a may be positioned centrally on the axle 324 to divide the collection volume into two equal parts. Dividing the collection volume is advantageous because it can help maintain the tension line 323 (e.g., lace or cable) organized and avoid issues of the tension line 323 collecting on one side of the collection volume, thereby prematurely jamming the collection channel volume. The fin 314a may also act as a bearing support for the axle 324 at an intermediate position between the ends of the axle 324, thereby improving the structural integrity of the axle 324 and possibly allowing for use of lighter-weight materials that may reduce the cost of manufacturing the adjustment device 300. As an alternative, the fin 314a may be part of the axle 324 and extend as a disc from the axle 324 at an axial location along axis E-E between the driven gear 310 and driven gear 311.

Figure 20:
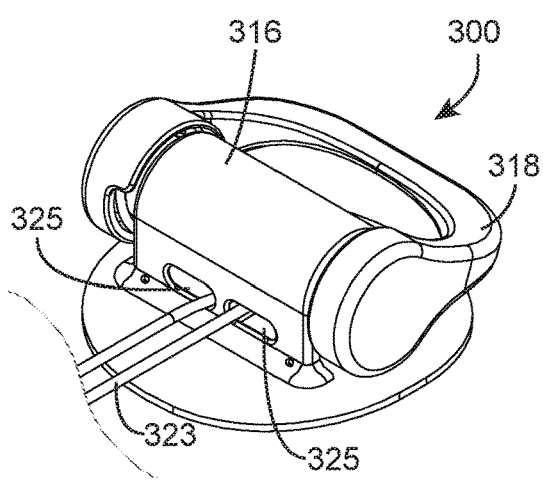
FIG. 20 is a top, rear, and side perspective view of the device of FIGS. 18 and 19 along with a tension line connected to the device.
Figure 21:
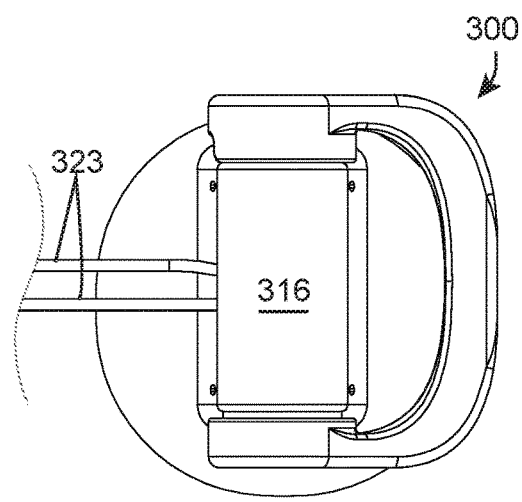
FIG. 21 is a plan view of the device and tension line shown in FIG. 20.
Figure 22:
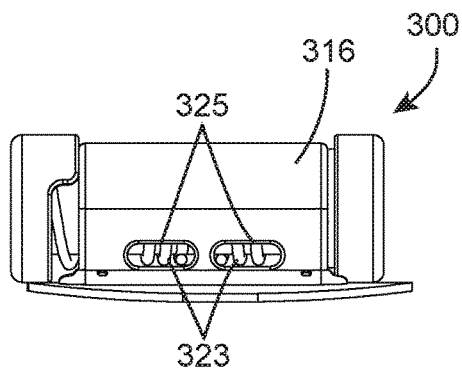
FIG. 22 is a rear elevation view of device and tension line shown in FIG. 22.
Figure 23:
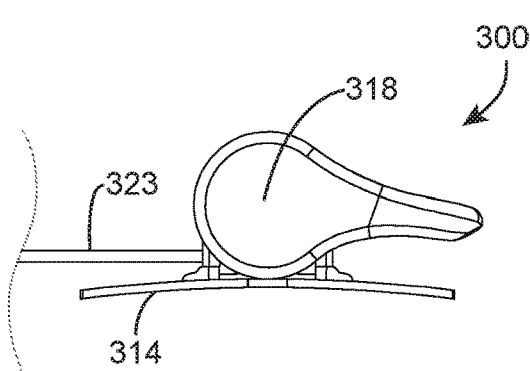
FIG. 23 is a side elevation view of the device and tension line shown in FIG. 23.
Figure 24:
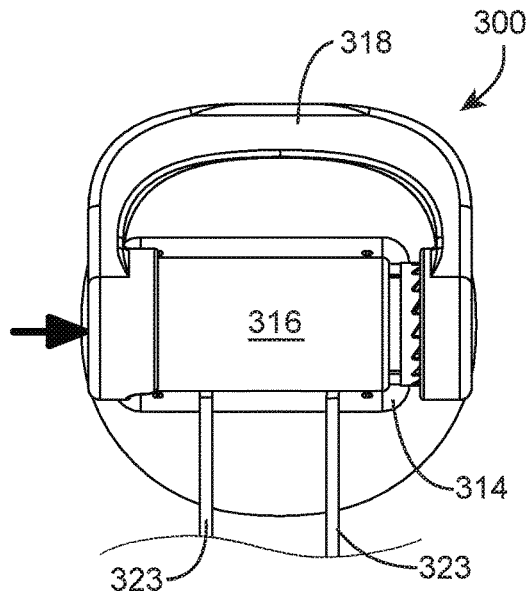
FIG. 24 is a plan view of the device of FIG. 22 with the lever of the device translated in the direction of arrow to release tension in the tension line.
Figure 25:
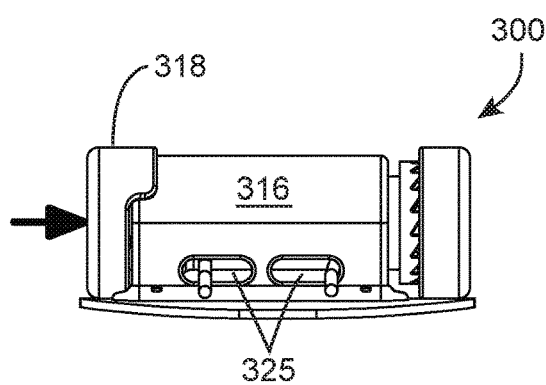
FIG. 25 is a rear elevation view of the device shown in FIG. 24.
Figure 26:
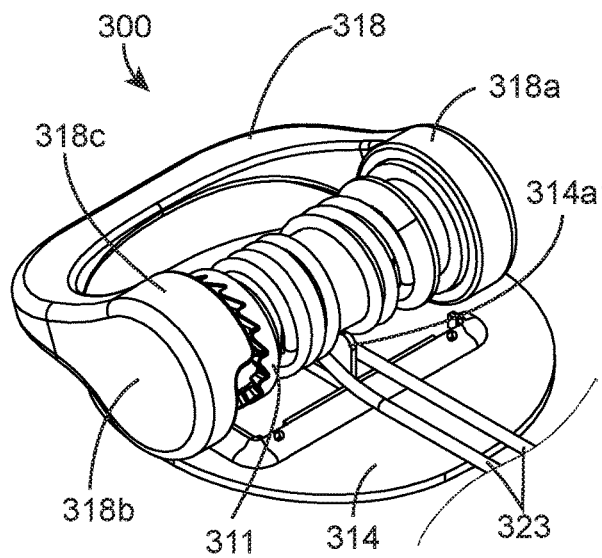
FIG. 26 shows the device of FIG. 20 with a cover removed to show detail underneath.
Figure 27:
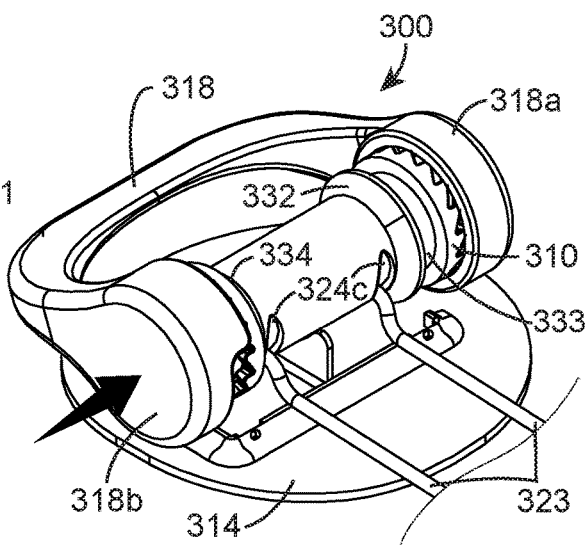
FIG. 27 shows the device of FIG. 24 with a cover removed to show detail underneath.
Figure 28:
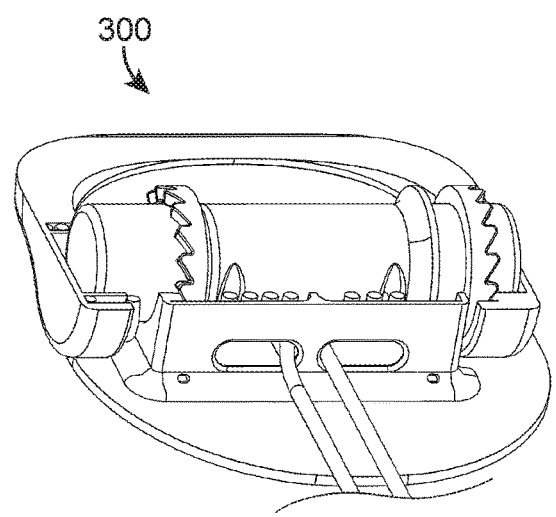
FIG. 28 is a partial cutaway of the device shown in FIG. 26.
Figure 29:
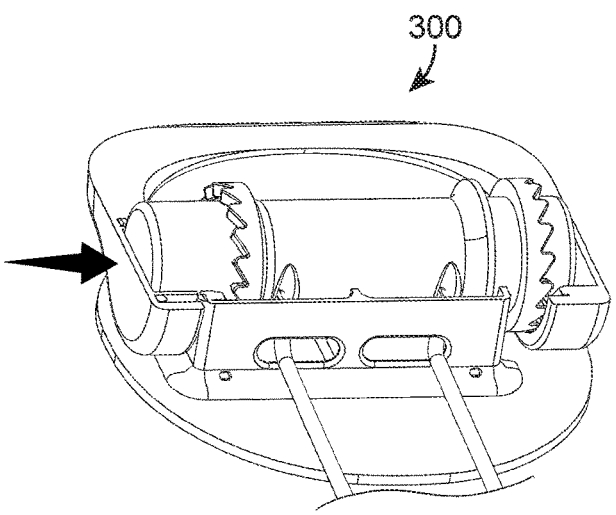
FIG. 29 is a partial cutaway of the device shown in FIG. 27.
Figure 30:
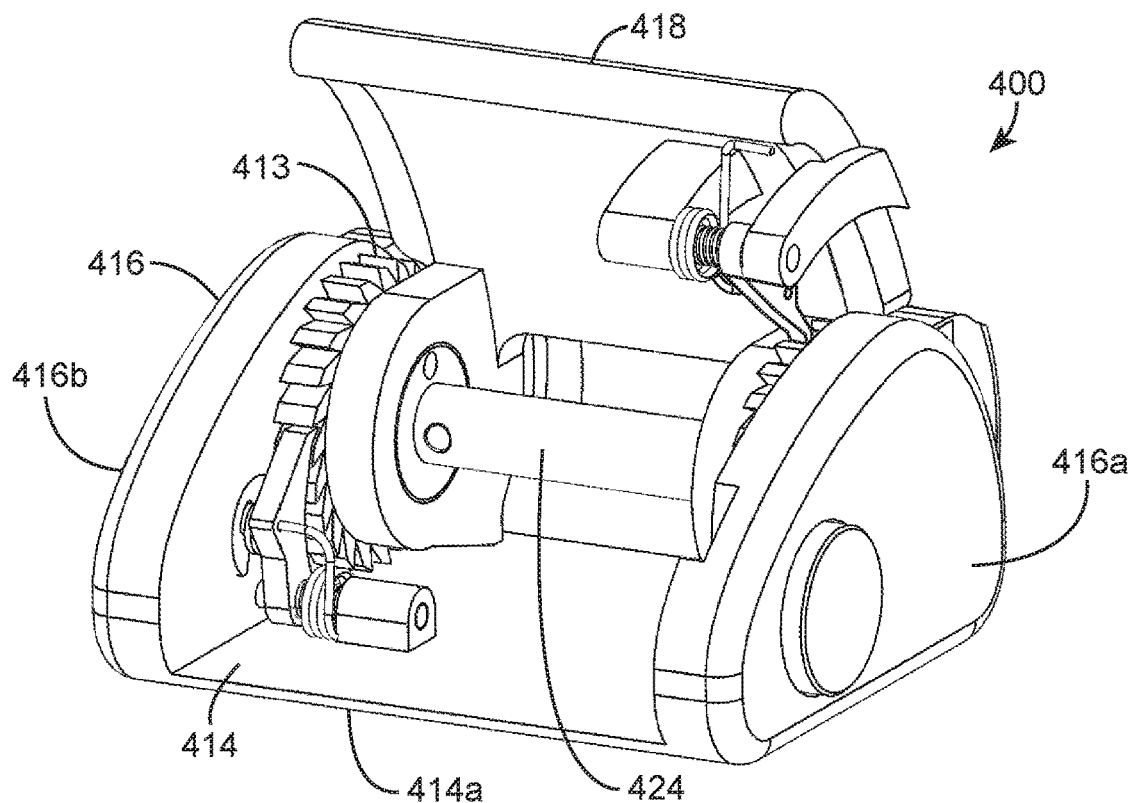
FIG. 30 is a front, top, and side perspective view of another embodiment of an adjustment device in accordance with an aspect of the disclosure.
Figure 31:
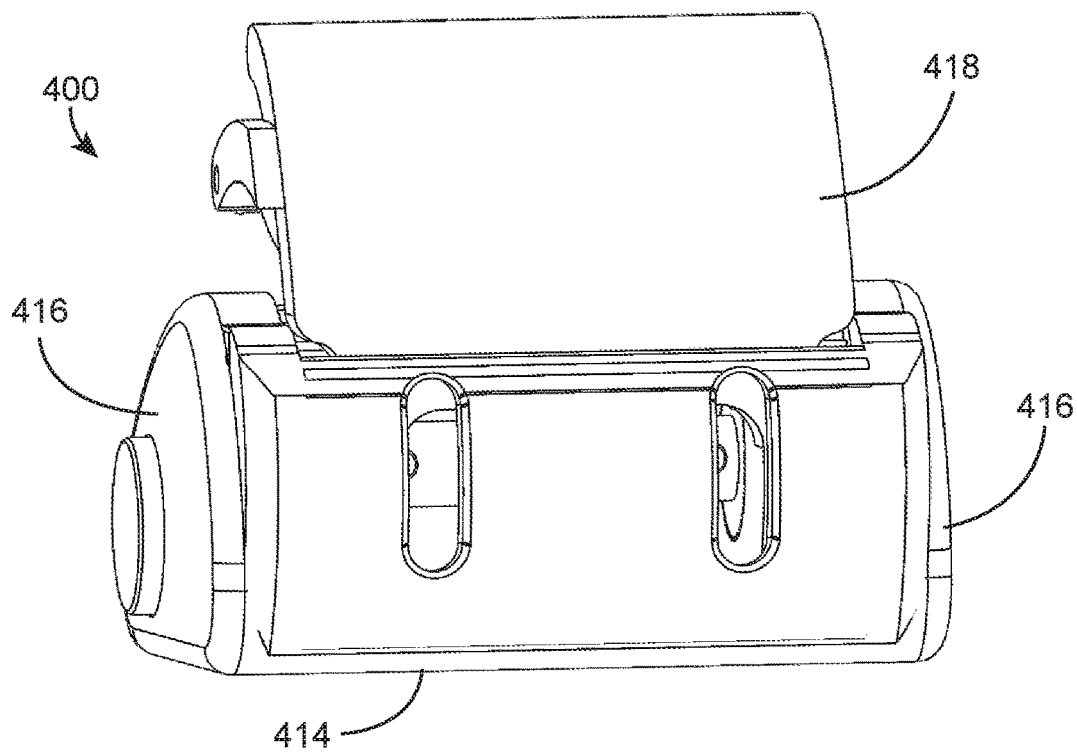
FIG. 31 shows a rear, top, and side perspective view of the device of FIG. 30.

The cover 316 also defines entrance and exit holes 325 (FIG. 19) for the tension line 323 to pass into the collection volume, as shown more fully in FIGS. 20, 28, and 29. The holes 325 may be elongated slots that are elongated in a direction parallel to the axis E-E, as shown in FIG. 19. The slotted holes 325 may allow the tension line 323 to shift slightly in the axial direction to accommodate different angles and forces in the tension line 323 as the tension line 323 passes through the cover as it is being collected around the axle 324. For example, the tension line shown in FIG. 20 extend near the inner ends of the slotted holes 325, whereas in FIG. 24, the tension line shown extend near the outer ends of the slotted holes 325.

The axle 324 defines two holes 324c (FIGS. 18, 27) passing through for connection of the tension line 323 to the axle 324. The axle 324 is configured to terminate the tension line 323 (e.g., lace or cable) at the axle 324 or to allow for a continuous tension line (e.g., cable or lace) to pass through the holes 324c of the axle 324 whereby the tension line 323 will be appropriately collected around the axle 324 upon rotation of the axle 324 relative to the cover 316 and the base 314.

In the embodiment shown, there are two through holes 324c passing through the axle 324 at an angle that enables the tension line 323 to exit the holes 324c at an angle that is sufficiently tangent to the outer circumference of the axle 324 in order to mitigate weakening the tension line 323 upon winding (i.e., collection) of the tension line 323. The end of the holes 324c (shown in FIG. 19) also includes a blind hole 324d that is larger than the corresponding through holes 324c such that a lace knot or cable termination feature (swaged onto the cable) can recess into this portion of the feature for applications that choose to terminate the lace or cable at the axle 324. For embodiments where it is desired to pass the tension line 323 through the axle 324 in one continuous cable, a trough 324e (shown as an elongated recess below the surface of the axle 324) is formed in the axle to allow the tension line 323 to route from one hole 324c to the other hole 324c so that the tension line 323 does not interfere with the fin 314a that extends from the base 314. In the alternative embodiment were the fin 314a1 extends from the axle 324 instead of the base 314 or cover 316, a split or dart in the fin could also provide clearance for a continuous cable to be passed from one side hole to the other in the axle 324.

The axle 324 has additional distinguishing features from the axle 224 of the previously described device 200. In the embodiment shown, the axle 324 includes a first lip extending circumferentially around the axle 324. The first lip extends radially from the outer surface of the axle 324. The first lip 332 (FIG. 27) is spaced axially along axis E-E from the first driven gear 310 and is positioned to block the tension line 323 from collecting into an annular groove 333 between the first lip 332 and the first driven gear 310. The groove 333 extends a predetermined amount along axis E-E that is required to allow for translation of the axle 324 during disengagement of the driving gear 320 and first driven gear 310. This annular groove 333 along the axle 324 should not contain tension line 323 to ensure full translation of the 318 lever and simultaneous disengagement of the spool 312 from the driving gear 320 and the ratchet gear 313. It will be appreciated that if the first lip 332 is omitted, the tension line 323 could collect onto the spool 324 up to the back side of the driving gear 320, which could inhibit relative axial translation between the axle 324 and the lever 318.

The axle 324 also includes a second lip 334 (FIG. 27) extending circumferentially around the axle 324 along the back side of the second driven gear 311. The second lip 334 includes a filleted corner to facilitate manufacturing.

The lever 318 has ends 318*a* and 318*b* have similar construction to ends 218*a* and 218*b* of lever 218. The lever 318 has the same function as the lever 318 for winding the axle 324. In addition, the second end 318*b* of the lever 318 in the embodiment shown has a shoulder 318*c* that extends axially (parallel to axis E-E) from a circular outer edge 318*d* of the second end 318*b*. The shoulder 318*c* extends circumferentially about 180 degrees around the outer edge 318*d*. The shoulder 318*c* extends to cover and protect (e.g., from incursion of debris) a space between the second end 318*b* of the lever 318 and the second end 316*b* of the cover 316. Due to the location and extent of the shoulder 318*c* relative to the sides of the cover 316, the shoulder 318*c* will interfere with the cover 316 and prevent the lever 318 from being translated axially along axis E-E when the lever 318 is rotated about axis E-E more than 45 degrees from the initial rest position shown in FIG. 20, for example. However, the shoulder 318*c* does not otherwise interfere or restrict any other movement of the lever 318 required for rotation of the spool 312 in a first direction where tension line is collected or otherwise wound on the spool 312.

An example adjustment device 300 may have the following features and dimensions, which may be for an adjustment device used on an article of footwear, such as a shoe or boot. The lever may have an arm length of 19 mm measured from the central axis extending through first and second ends of the lever. The axle diameter may be about 8 mm. The driving and driven gears may have 16 teeth. The degree of rotation per gear tooth may be 22.5 degrees. The spool diameter may have a range of 8 mm (when the axle is empty) to 12 mm when the axle is full. The spool length between lips 332 and 334 may be 16 mm. The collection volume may be approximately 1005 cubic mm. It is notable that that the volume of tension line collection is relatively small because the volume requirement for collection of lace for a shoe, such as a bicycle shoe, is low. This volume is still more than double that of the low-profile designs for some prior art devices.

The example device may have approximate dimensions of length (measured along the longitudinal axis), width, and height of 33 mm, 25.5 mm, and 13 mm, respectively. When the spool is empty, the mechanical advantage starts at 2.1:1, and when the spool is full (has collected tension line) the mechanical advantage is 1.7:1.

In the example embodiment of device 300, all parts except for the spring 338 may be made as a thin walled part made from injection molded plastic such as nylon. The axle 324 may alternately be a solid plastic part or be made of metal. Alternatively, any combination or all parts of the device 300 may be made of metal.

Figure 35:
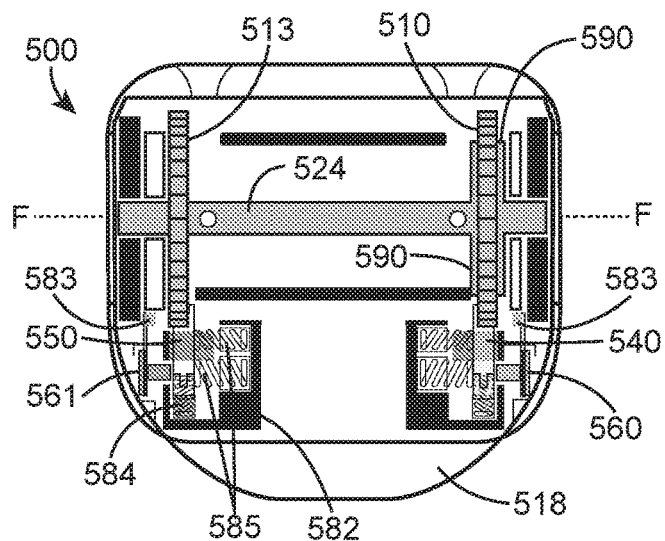
FIG. 35 is a plan view of another embodiment of a tension device in accordance with the disclosure. The lever is shown transparent to show details of the device underneath the lever.
Figure 36:
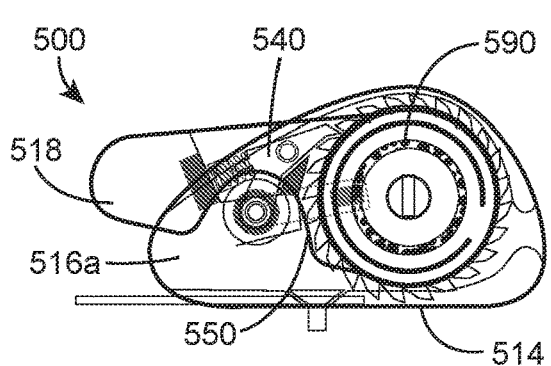
FIG. 36 is a transparent side elevation view of the device shown in FIG. 35.
Figure 37:
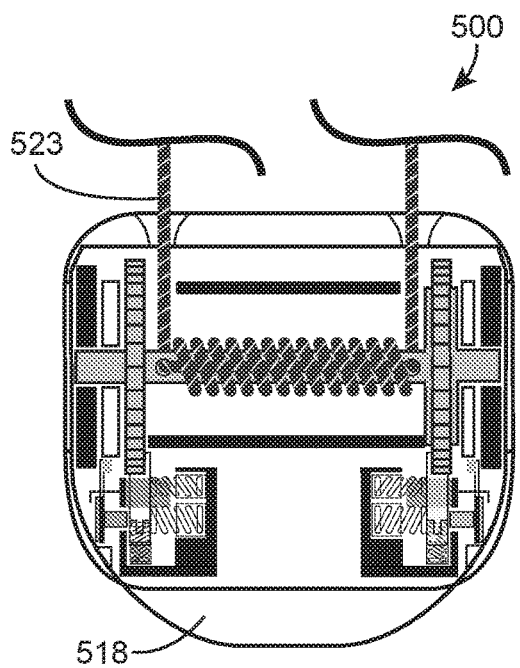
FIG. 37 is a transparent plan view of another embodiment of a tension device in accordance with an aspect of the disclosure.
Figure 38:
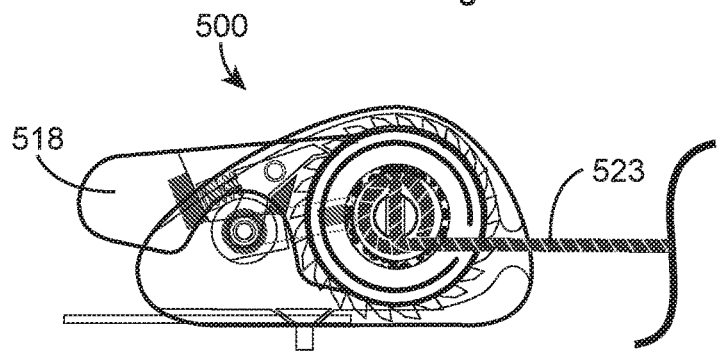
FIG. 38 is a transparent side elevation view of the device shown in FIG. 37.
Figure 43:
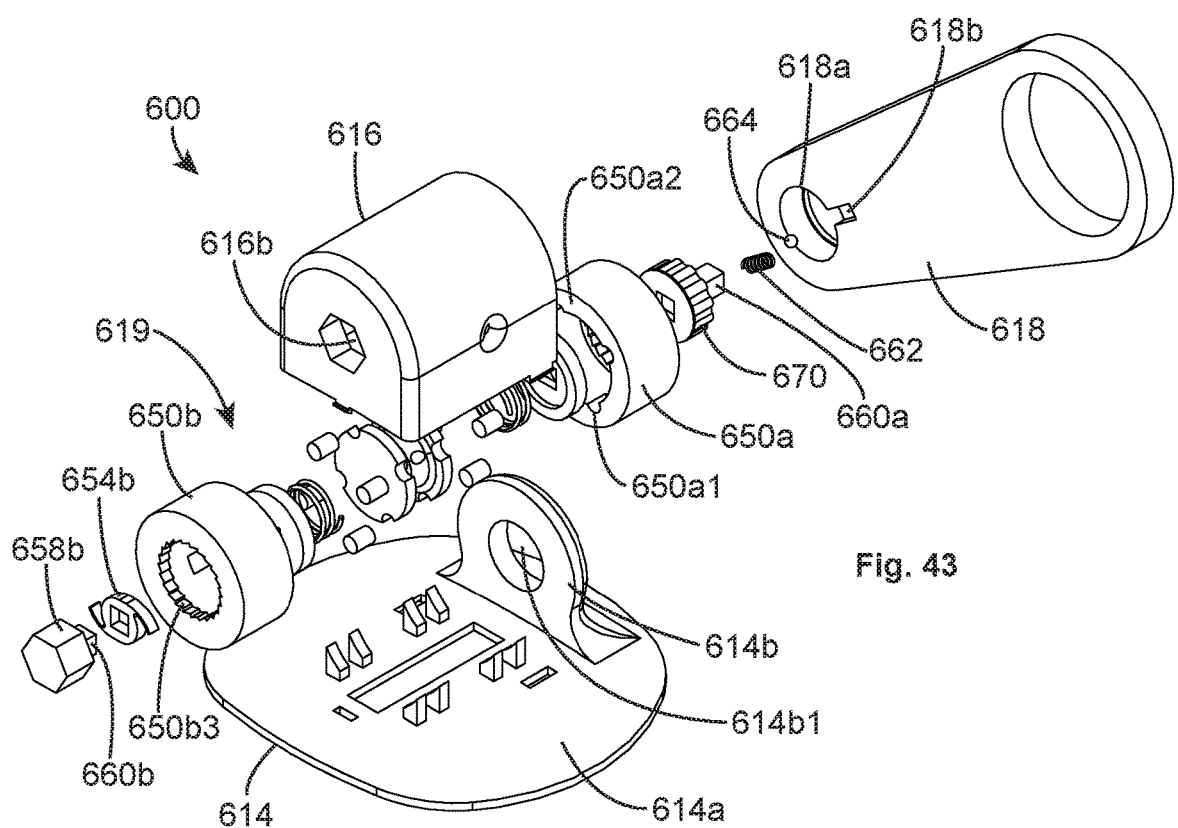
FIG. 43 is an assembly drawing of another embodiment of a tension device in accordance with an aspect of the disclosure, viewed from a top, front, and side of the device.
Figure 44:
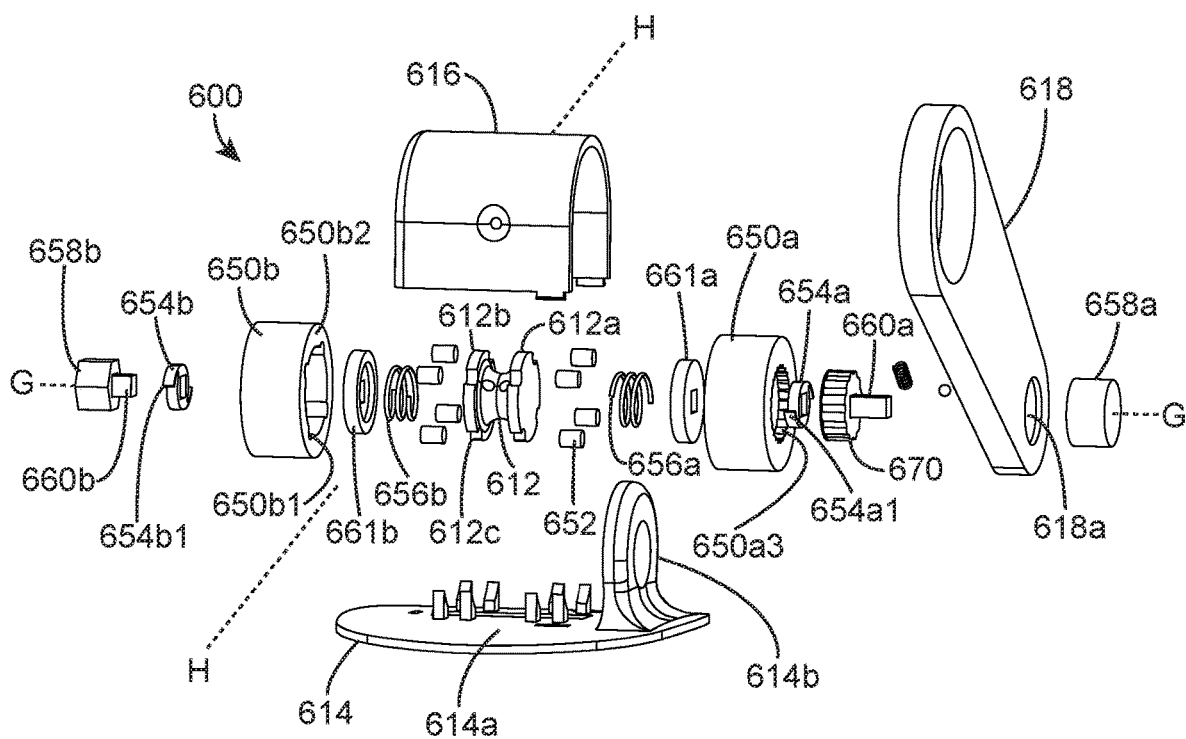
FIG. 44 shows the device of FIG. 43 viewed from the top and side of the device.
Figure 45:
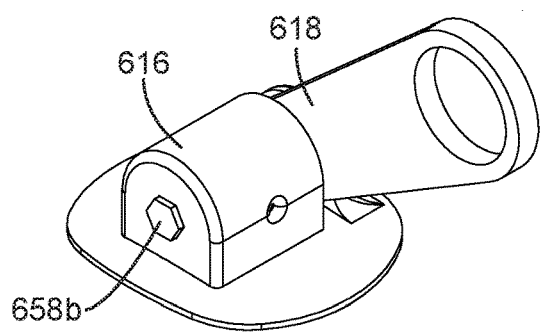
FIG. 45 shows the device of FIG. 43 assembled.
Figure 46:
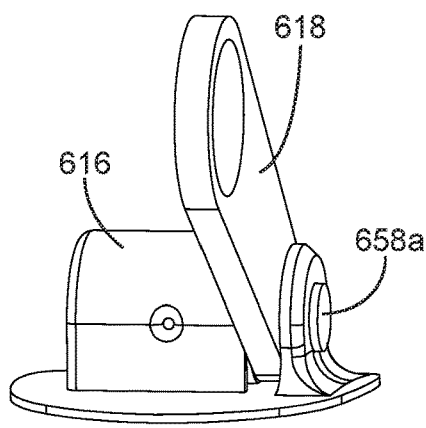
FIG. 46 shows the device of FIG. 44 assembled.

FIGS. 30-34 show views of another adjustment device 400 that includes a housing comprised of upstanding sides 416*a*, 416*b* and a base 414, a ratcheting winding lever 418 pivotally connected to the sides 416, and a spool 412 pivotally connected to the sides 416. The sides 416*a*, 416*b* extend from the base 414, which is generally planar. The base has a lower surface 414*a* for attachment to an article, such as a wearable article. The spool 412 includes a central axle 424 that extends between the sides 416*a* and 416*b* of the housing 416. The axle 424 extends from a first end 424*a* to a second end 424*b* along a longitudinal axis F-F (FIG. 35) that is parallel to the plane of the lower surface 414*a* of the base 414. The spool 412 includes a driven gear 410 and a ratchet gear 413 fixed to the axle 424. The driven gear 410 and the ratchet gear 413 are spaced from the ends 424*a* and 424*b* of the axle 424. The gears 410 and 413 have teeth that extend perpendicular to the longitudinal axis F-F. The gears 410 and 413 have curved teeth that are oriented in the same direction. The teeth have a coasting side and a driving side.

Figure 32:
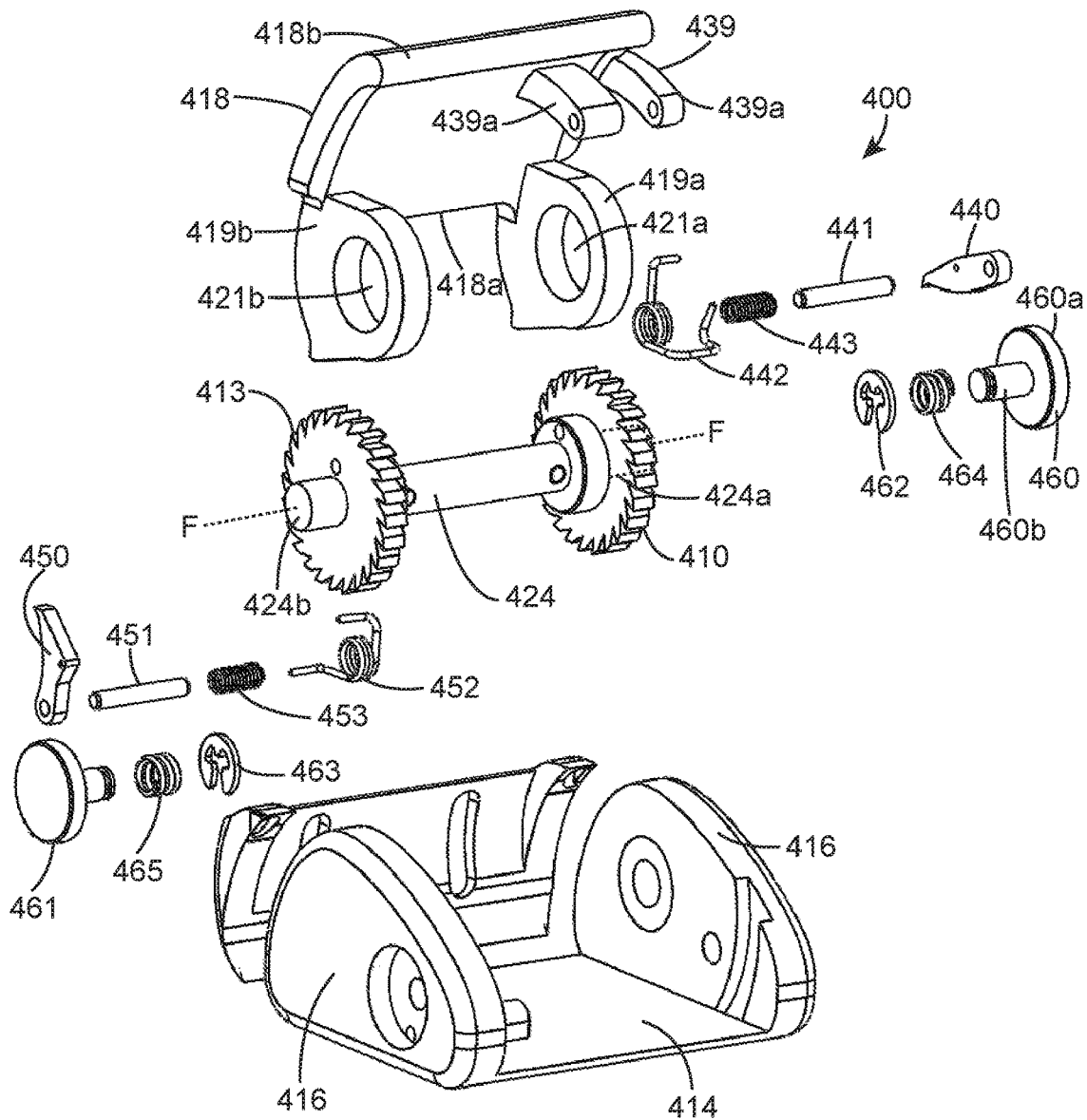
FIG. 32 is an assembly drawing of the device shown in FIGS. 30 and 31.

As shown in greater detail in FIG. 32, the lever 418 has a first end 418*a* with first and second hinge flanges 419*a*, 419*b* having axially aligned openings 421*a*, 421*b* through which the first and second ends 424*a*, 424*b* of the axle 424 are received. Thus, when the device 400 is assembled, a first hinge flange 419*a* is positioned between a first side 416*a* of the housing 416 and the driven gear 410 and the second hinge flange 419*b* is positioned between the second side 416*b* of the housing 416 and the ratchet gear 413. The ends 424*a*, 424*b* of the axle 424 extend outwardly beyond the hinge flanges 419*a*, 419*b* and are seated in holes (not shown) of the sides 416*a*, 416*b* of the housing 416. The axle 424 may be a solid axle with through holes for receiving a tension line (not shown).

The lever 418 has a second end 418*b* opposite the first end 418*a*. A pawl 440 is pivotally mounted with a hinge pin 441 to the underside of the lever 418 at the second end 418*b* thereof. Specifically, a hinge 439 extends from the underside of the lever 418. A hinge pin 441 extends through the knuckles of the hinge 439 and through the pawl 440, a torsional spring 442, and a coil spring 443, which are all positioned side by side between the knuckles of the hinge 439. The knuckles of the hinge 439 are spaced far enough apart to provide the pawl 440 with a range of translational movement parallel to axis F-F. The coil spring 443 urges the pawl 440 outward into alignment with the teeth of the driven gear 410.

The pawl 440 is also biased by the torsion spring 442 to engage the teeth of the driven gear 410. The pawl 440 is configured to engage the drive side of the teeth of the driven gear 410 so that the driven gear 410 and the axle 424 (and thus the entire spool 412) are rotated in a first direction about axis F-F as the lever 418 is pivoted about the axis F-F in a first rotational direction (i.e., clockwise in FIG. 33). The pawl 440 is configured to skip across the coast side of teeth of the driven gear 410 when the lever 418 is pivoted about the axis F-F in a second rotational direction opposite the first direction.

A spring biased ratchet pawl 450 is mounted to the base 414 to engage the ratchet gear 413. Specifically, when the spool 412 is rotated in the first direction about axis F-F, the pawl 450 is configured to skip over the teeth of the ratchet gear 413. When the lever 418 rotates in the second direction about axis F-F, or when the lever 418 is stationary, the pawl 450 engages the drive side of the teeth of the ratchet gear 413 to prevent the axle 424 (and thus the spool 412) from rotating in the second direction (i.e., prevent the axle and spool from reversing and loosening tension in the tension line). The ratchet pawl 450 is mounted to the base 414 on a sliding mount like the lever-mounted pawl 440 so that the pawl 450 is configured to translate axially parallel to axis F-F. A hinge pin 451 extends through the pawl 450, a torsional spring 452, and a coil spring 453. The pawl 450 is configured to translate along the hinge pin 451, which is parallel to axis F-F. The coil spring 453 urges the pawl 450 into engagement with the teeth of the ratchet gear 413.

Two coaxially aligned push buttons 460, 461 are mounted, respectively, to the sides 416a, 416b. A first push button 460 has a head 460a and a grooved stem 460b that extends through the first side 416a of the housing 416 and is connected thereto with a circlip 462. The button 460 is urged outwardly away from the first side 416a with a spring 464 around the stem 460b and positioned between the head 460a and the first side 416a. A second push button 461 has a head 461a and a grooved stem 461b that extends through the second side 416b of the housing 416 and is connected thereto with a circlip 463. The button 461 is urged outwardly away from the second side 416a with a spring 465 around the stem 461b and positioned between the head 461a and the second side 416b.

Figures 33, 34:
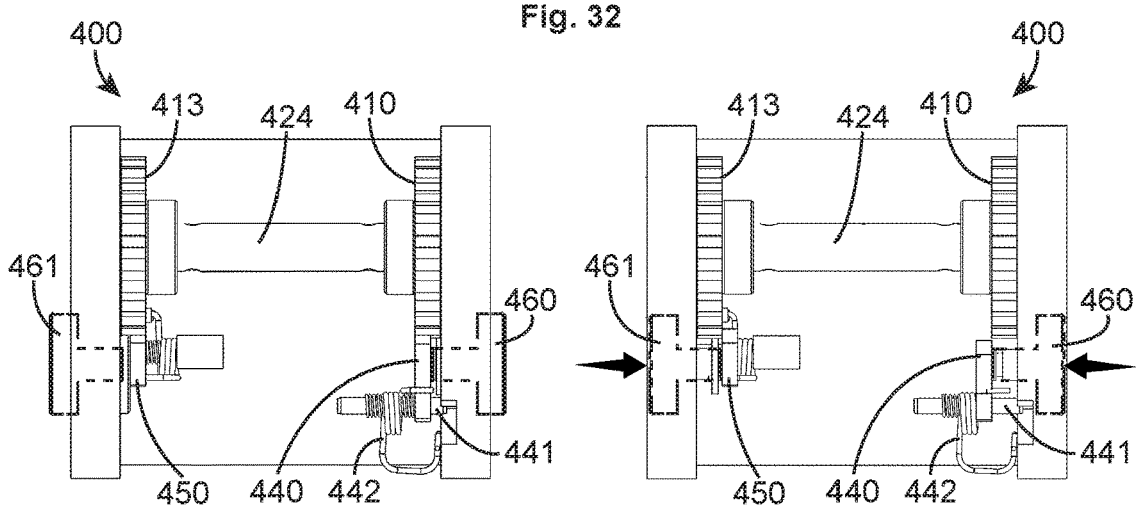
FIG. 33 is a plan view of the device of FIG. 30 with the lever removed for clarity of illustration and with the pawls shown in engagement with the gears of the spool.
FIG. 34 is a plan view of the device of FIG. 30 with the lever removed for clarity of illustration and with the pawls shown disengaged from the gears of the spool.

The push buttons 460 and 461 are coaxially aligned along an axis parallel to axis F-F. The first push button 460 is configured to align with the first pawl 440 when the lever 418 is rotated to a fully closed or folded position (FIG. 34). When the lever 418 is in the fully closed or folded position, the push button 460 can be pushed inwardly to translate the pawl 440 in a direction parallel to the longitudinal axis F-F, which disengages the first pawl 440 from the driven gear 410. The second push button 461 aligns with the second pawl 450. When the second push button 461 is pushed inwardly, the pawl 450 translates inwardly out of engagement with the ratchet gear 413. When both the first and second push buttons 460, 461 are pushed inwardly (opposing forces are applied to the buttons), both gears 410 and 413 are disengaged from the first and second pawls 440, 450, allowing the spool 412 to rotate freely about axis F-F so that the tension line can be unwound. The push buttons 460 and 461 are arranged so that they can be pushed manually using a one-handed pinching motion of a user, using the thumb and index finger, for example.

FIGS. 35-38 show an alternative adjustment device 500 to adjustment device 400, where like elements are shown incremented by "100". Specifically, the adjustment device 500 includes a tension limiter to avoid overtightening the tension line.

Also, the adjustment device 500 include a different pawl disengagement mechanism from that of device 400. Rather than use torsional springs, the adjustment device uses only coil springs for its pawl disengagement mechanism. Specifically, the device 500 includes a spool 512 with an axle 524 fixed to a driven gear 510 and a ratchet gear 513. A pawl 540 is used to drive the driven gear 510 as the lever 518 is rotated about axis F-F in a first advancing direction. A ratchet pawl 550 prevents the unwinding of the spool 510 after the tension line is wound onto the spool 512. The ratchet pawl 550 is mounted to the base 514 with a pawl release housing 582 and a release braking mechanism 583, while the ratchet pawl 540 is mounted to the lever 518 with a pawl release housing 582 and a release braking mechanism 583. The release housing and braking mechanisms on both sides of the spool 512 are constructed and operate the same way so the remaining discussion is of the engagement and disengagement and braking mechanism of the ratchet pawl 550.

The ratchet pawl 550 permits rotation of the spool 512 with the lever 518 in a first rotational direction to wind tension line and blocks rotation of the spool 512 in the second direction opposite the first direction as previously described. In order to release the pawl 550, the user can push on the release button 561 located on the side of the base 514. The pawl housing 582 includes helical compression springs 584 that biases the pawl 550 into the drive side of the gear teeth of ratchet gear 513, and includes helical compression springs 585 that bias the pawl 550 (in a direction parallel to the axis F-F) back into alignment with the gear 513 when the pressure has been removed from the release button 561.

The pawl disengagement mechanism is also connected to a release braking mechanism that is engaged with the gears 510 and 513 when the pawls 540, 550 are disengaged from the gears 510, 513. The release braking mechanism includes a friction brake 583 connected to the push button 561 that simultaneously translates into engagement with the side of the gear 513 as the pawl 550 translates out of engagement with the gear 513. The release braking mechanism provides the user with the ability to control the speed and amount of tension line released upon disengagement of the pawls 540, 550 in order to prevent a rapid or complete unwinding of the tension line upon release.

FIGS. 39A-39B show an alternate device 500' that is the same as the device 500 but differs as follows. Specifically, the device 500' omits the tension limiter of device 500 and includes a spool 512' with an axle 524' configured to wind a flat strap tension line 523' with a looped end instead of a lace or cable.

The spool 512' includes a strap capturing mechanism that includes an off-axis pin 522' that is rigidly mounted parallel to and radially spaced from the axle 524'. The pin 522' extends from driven gear 510' to ratchet gear 513'. The device 500' is configured to wind a strap 523' that has ends formed as a stitched or fastened loop 523a', such as shown in FIG. 39B. The axle 524' extends through the loop 523a' to retain the strap 523' to the axle 524'. Due to the off-axis position of the pin 522', the pin 522' catches the strap 523' that is looped around the axle 524' and extending in opening 514d' during the first rotation of the pin 522' about the axis axle 524', as shown in greater detail in FIG. 39B. This arrangement allows the device 500' to wind and release a single strap along a single pathway (i.e., from one direction).

In prior art, tension line strap is captured by a split axis wherein a strap can pass through but as the axis is rotated, the strap is captured and collected around. In device 500', the profile height of the adjustment device 500' can be greatly reduced by using a solid axle 524'. This arrangement avoids the need for the user to manually feed the strap through a split axis or other mechanism in order to use the device 500'. The solid axle can be strong enough to maintain the strap 523' with a much smaller diameter than is required for an axle with a greatly compromised strength due to a split axis or hole through the axis.

FIGS. 40A to 40D show yet another alternate device 500" having features corresponding to device 500'. Notably, the base 514" defines a tension line pathway that permits dual direction tension line adjustment so that the tension line can be wound into (and dispensed from) the device from two directions. The device 500" has a spool 512" that is the same as spool 512' of device 500'. However, the strap 523" differs from strap 523' in that strap 523" does not have a closed or looped end fastened to the axle 524". Instead, as shown in FIG. 40C, the strap tension line 523" extends through the device 500" from a first open end 514a" over the axle 524" and between the axle 524" and the pin 522" and through a second opening 514b". Then, when a user rotates the lever 518" in the advancing direction shown in FIG. 40D, the tension line 523" is drawn into the device 500" through both openings 514a" and 514b" in the direction of the arrows.

FIGS. 41A-41C show various side views of a one directional fit system, such as adjustment device 500', with a focus on a side view of a toroidal tensioning line channel 60 disposed therein. FIG. 41A shows an outline view of the channel 60 in relationship to a hinged lever 62 and a housing 64. FIG. 41B shows a view similar to that of FIG. 41A, but with radial dimension of the toroidal tensioning line channel 60 measured from an outer side of a spool axle 66 to an inner side of housing 64. The radial dimension is a determinant of the length of tension line that can be wound on the axle 66 and stored in the toroidal tensioning line channel 60. FIG. 41C shows a view similar to those of FIGS. 41A-41B, but with a focus on depicting the toroidal tensioning line channel 60 as a pseudo-solid for illustrative purpose, and further showing a single entry and exit pathway 68 of tensioning line into the channel 60.

FIGS. 42A-42C show embodiments of a toroidal tensioning line channel 70 within a dual-direction fit system, such as adjustment device 500". FIG. 42A shows an outline view of the channel 70 in relationship to a hinged lever 72 and a housing 74. FIG. 42B shows a view similar to that of FIG. 42A, but with radial dimension of the toroidal tensioning line channel 70 measured from an outer side of a spool axle 76 to an inner side of housing 74. The radial dimension is a determinant of the length of tension line that can be wound on the axle and stored in the toroidal tensioning line channel 70. FIG. 42C shows a view similar to those of FIGS. 42A-42B, but with a focus on depicting the toroidal tensioning line channel 70 as pseudo-solid for illustrative purpose, and further showing a dual entry and exit pathway 78a, 78b of tensioning line into the channel 70.

FIGS. 43-52 show another adjustment device 600, which includes a base 614 and cover 616 forming a housing, a spool 612, a lever 618 coupled to the spool 612, and a ratcheting advance and release mechanism 619 (FIG. 43) coupled between the lever 618 and the spool 612 configured to drive (i.e., rotate) the spool 612 in a first rotational winding direction and to selectively permit the spool 612 to rotate in a second rotational unwinding direction opposite the first direction.

The base 614 and the cover 616 connect together, such as by snap fit or other fastening means. The base 614 includes a mounting flange 614a for mounting to an article, such as a wearable article. The flange 614a may be a stitch flange that can be attached to an article by sewing with needle and thread.

The cover 616 houses the spool 612 and portions of the ratcheting advance and release mechanism 619. The spool 612 and ratcheting advance and release mechanism are coaxially aligned with a central longitudinal axis G-G around which the spool 612 rotates. A central axis H-H extends through the device 600 perpendicular to axis G-G. The spool 612 has opposing end flanges 612a, 612b with a plurality of circular grooves 612c formed along outer edges of the flanges 612a, 612b. The grooves 612c are spaced circumferentially apart, e.g., equidistantly.

Figure 48:
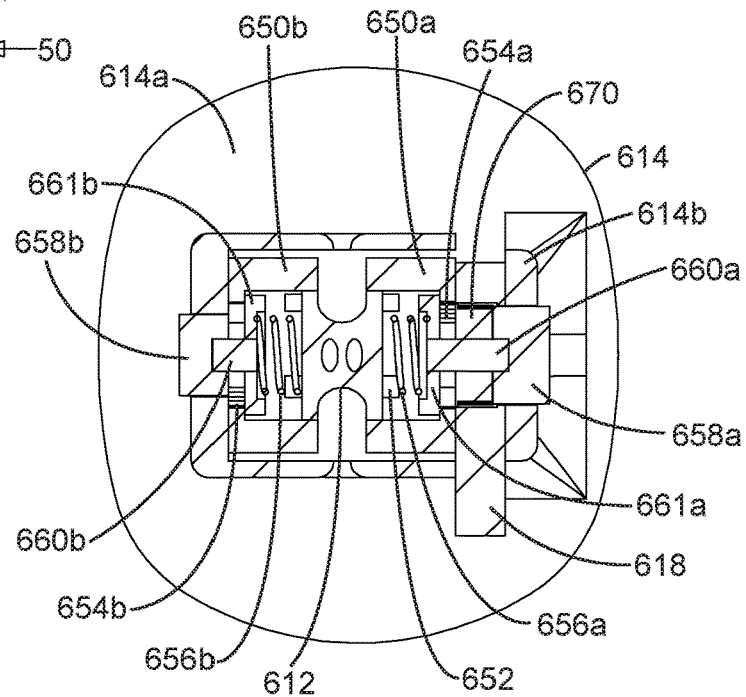
FIG. 48 is a view of the device of FIG. 47 viewed along line 47-47 in FIG. 47.
Figure 49:
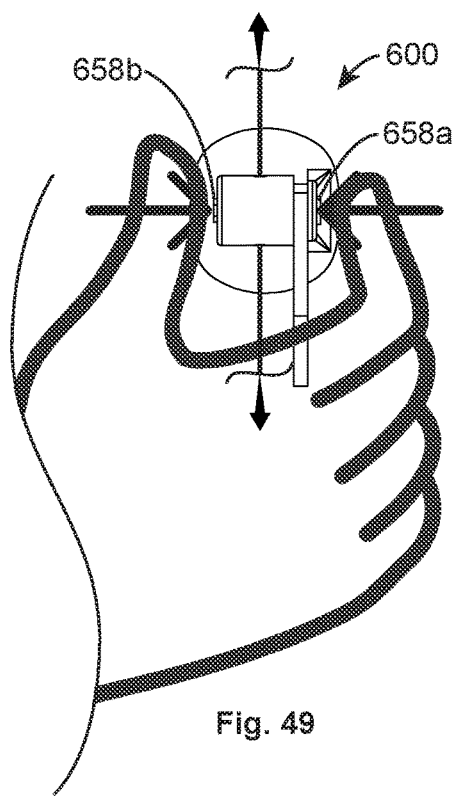
FIG. 49 shows a one-handed releasing motion to release tension in the device of FIGS. 45 and 46.
Figure 50:
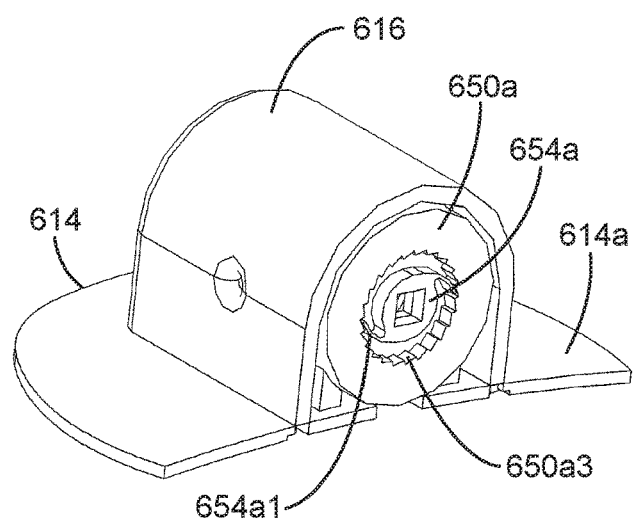
FIG. 50 shows a view of the device of FIG. 46 viewed along line 50-50 in FIG. 46.

The spool 612 is coupled to the ratcheting advance and release mechanism 619 as follows. Annular shaft couplers 650a, 650b are coaxial with the spool 612 and are connected to corresponding flanges 612a, 612b of the spool 612 with pins 652. Specifically, coupler 650a defines grooves 650a1 that align with grooves 612c on first flange 612a of spool 612 and coupler 650b defines grooves 650b1 that align with grooves 612c on the second flange 612b of spool 612. The grooves 612c are located on an outer edge of the flanges 612a and 612b, while the grooves 650b1 and 650b2 are located on an inner annular edge of the couplers 650a, 650b so that the flanges 612a and 612b are received into inner annular openings of the couplers 650a, 650b, as shown in FIG. 48. The pins 652 rotationally fix the spool 612 to both couplers 650a, 650b so that the spool and the couplers 650a, 650b rotate in unison axis G-G.

Also housed within the inner annular openings of the couplers 650a and 650b are respective ratchet plates or wheels 654a, 654b, springs 656a, 656b, and spring caps 661a, 661b. The springs 656a, 656b urge the ratchet wheels 654a, 654b outward (with respect to central axis H-H) along axis G-G. Each coupler 650a, 650b has a radially inner (radially with respect to the central axis of G-G) cylindrical surface divided into an inner side and an outer side (with respect to central axis H-H). The outer side of the cylindrical surface has a plurality of inner gear teeth 650a3, 650b3 while the inner side of the cylindrical surface is relatively smooth. Ratchet plate 654a includes pawls 654a1 that are oppositely directed from pawls 654b1 of ratchet plate 654b. The pawls 654a1 are configured to engage and drive the gear teeth 650a3 when the ratchet plate 654a rotates in the first rotational direction about axis G-G and to skip over the gear teeth when the ratchet plate 654a rotates in a second direction opposite the first direction. The pawls 654b1 are configured to skip over the gear teeth 650b3 when the ratchet plate 654b rotates in the first rotational direction about axis G-G and to engage with the gear teeth when the ratchet plate 654b is rotated in the second direction. This arrangement allows for a one-way spool winding of the spool 612.

A keyed central shaft 660a extends coaxially through ratchet wheel 654a, spring 656a, and spring cap 661a, while a keyed central shaft 660b extends coaxially through ratchet wheel 654b, spring 656b, and spring cap 661b. The central shaft 660a rotates in unison with ratchet wheel 654a and spring cap 661a, which have a keyed central opening mating with the shaft 660a. The central shaft 660b rotates in unison with ratchet wheel 654b and spring cap 661b, which have a keyed central opening mating with the shaft 660b.

FIG. 48 shows the ratchet plates 654a, 654b in a first configuration in which they both ratchet plates 654a, 654b are engaged with respective gear teeth 650a3, 650b3 on the outer side of the cylindrical surface of the couplers 650a and 650b. The ratchet plates 654a, 654b are longitudinally translatable along axis G-G from the outer sides to the inner sides of the cylindrical surface to disengage the pawls 654a1, 654b1 from the respective gear teeth 650a3, 650b3 in a second configuration. Disengagement of the ratchet plates 654a, 654b permits the spool to rotate freely in the second direction to unwind tension line. The longitudinal displacement of the ratchet plates 654a, 654b is selectively controlled by actuation of buttons 658a, 658b, further details of which are provided below. In a default position, the ratchet plates 654a, 654b are urged into the first configuration shown in FIG. 48.

As shown in FIG. 48, the ratchet plate 654a is coupled to the lever 618 by a gear 670 which is rotationally fixed to the central shaft 660a. The gear 670 is configured to be driven by the lever 618. Thus, rotation of the gear 670 caused by the lever 618 can be transmitted to ratchet plate 654a through the central shaft 660a.

Figure 47:
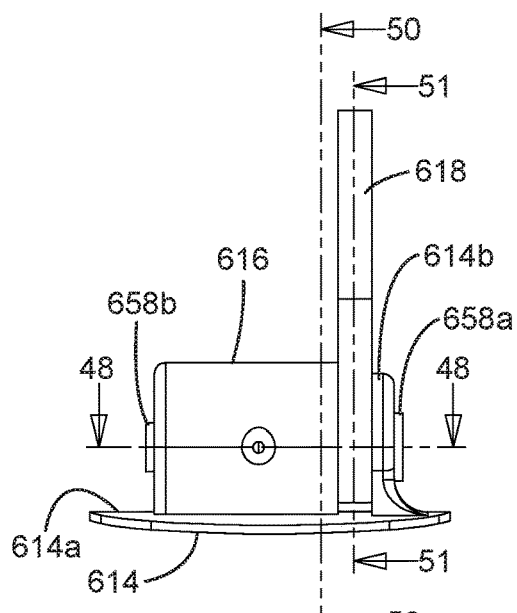
FIG. 47 is a front elevation view of the device shown in FIGS. 45 and 46.

The lever 618 defines a hole 618a and a radially directed slot 618b extending from the hole on an inner side (relative to axis H-H) of the lever 618. The hole 618a receives the gear 670 and the radial slot receives a spring 662 and a ball bearing 664 engaging the gear 670. The base 614 includes a flange 614b defining an opening 614b1 in axial alignment with the longitudinal axis G-G. The flange 614b extends perpendicular to the lower surface 614a of the base 614. The push button 658a extends outwardly (with respect to axis H-H) from and is retained in the opening 614b1 in the flange 614b. As shown in FIGS. 47 and 48, the lever 618 is assembled between the flange 614b and the coupler 650a.

The gear 670 is longitudinally (along axis G-G) displaceable on central shaft 660a relative to the hole 618a in the lever 618. As shown in FIG. 48, the gear 670 is adjacent the ratchet plate 654a, which are both urged longitudinally outwardly against the push button 658a by the spring 656a. The push button 658a may be pushed inwardly against the force of the spring 656a to longitudinally translate the gear 670 and the ratchet plate 654a to disengage the pawls 654a1 of the ratchet plate 654a from the internal gear teeth 650a3 of the shaft coupler 650a. Release of the button 658a causes the spring 656a to expand to translate the ratchet plate 654a back to its engagement position where the pawls 654a1 engage with the gear teeth 650a3.

The button 658b extends through a hole 616b of the cover 616. The button 658b has a hexagonal profile and the hole 616b is hexagonal. The mating shapes prevents rotation of the button 658b in the hole 616b. The button 658b has a central opening that receives an end of shaft 660b. The button 658b is configured to be pushed inward (relative to axis H-H) along axis G-G, in opposition of the force of the spring 656b, to translate the ratchet plate 654b along axis G-G to disengage the pawls 654b1 from the teeth 650b3. Release of the button 658b, causes the spring 656b to expand and translate the ratchet plate 654b back into engagement with the gear teeth 650b3.

Thus, the release of the ratchet plates 654a and 654b is parallel with the longitudinal axis G-G. When both ratchet plates 654a, 654b are in their first, engaged configuration, rotation of the lever about axis G-G in a first direction will cause the ratchet plate 654a to drive the coupler 650a and the spool 612 connected thereto to rotate in unison with the coupler 650a, which will cause tension line to be drawn inward and gathered around the spool 612. Also, when a user releases the lever 618, the reverse orientation of the pawls 654a1, 654b1 prevents the spool 612 from being unwound. However, when the ratchet plates 654a, 654b are in their second, disengaged configuration, by simultaneously pushing on both buttons 658a and 658b, the spool 612 is free to rotate in a reverse direction to permit the tension line to be reduced and the tension line to be unwound from the spool 612.

Figure 51:
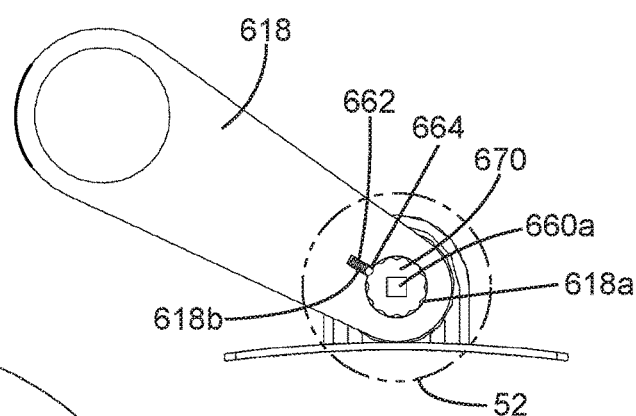
FIG. 51 shows a view of the device of FIG. 47 viewed along line 51-51 in FIG. 47.
Figure 52:
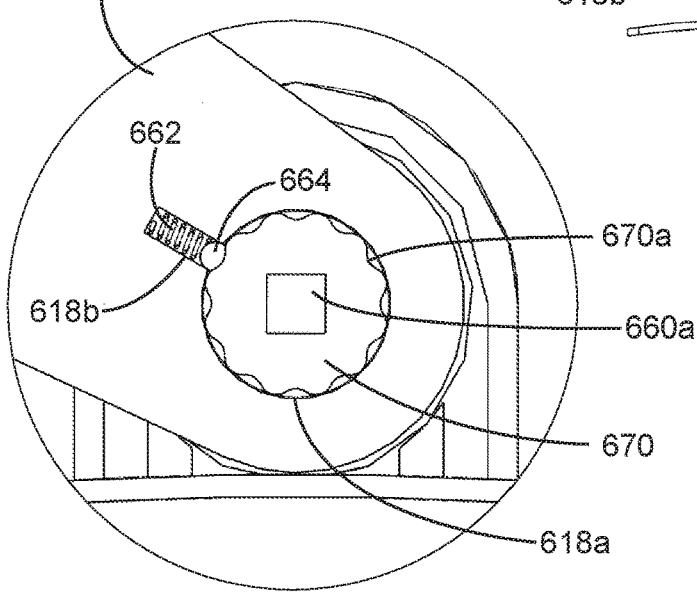
FIG. 52 is an exploded view of the area labeled 52 in FIG. 51.
Figure 57:
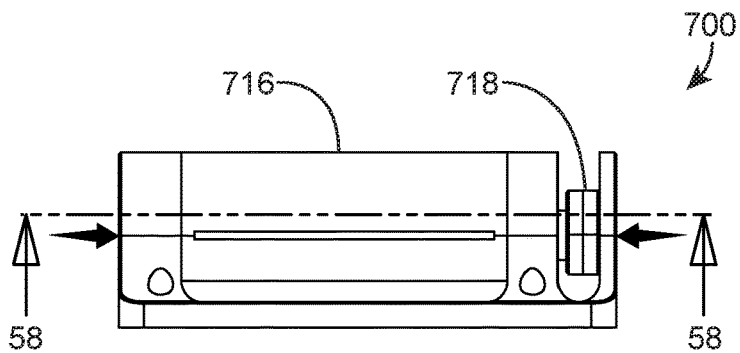
FIG. 57 is a front elevation view of the device of FIG. 53.
Figure 58:
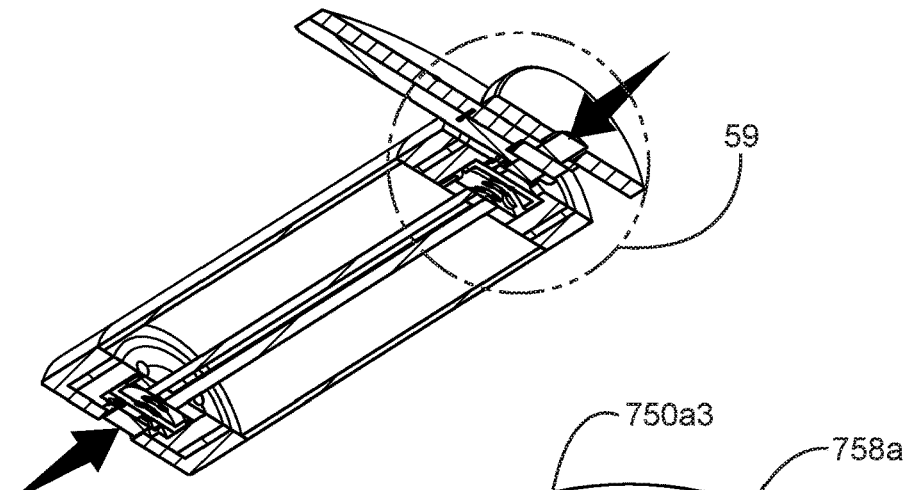
FIG. 58 is a view of the device shown in FIG. 53 along line 58-58 in FIG. 57.
Figure 59:
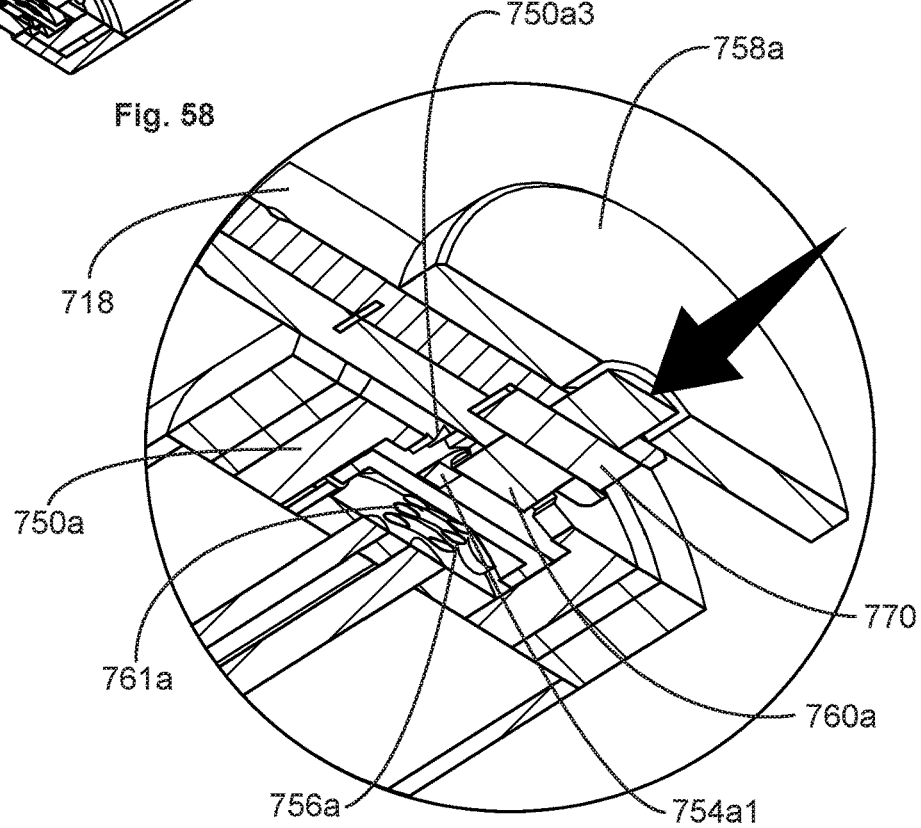
FIG. 59 is a detailed view of detail C in FIG. 58.

The spring 662, ball bearing 664, and gear 670 comprise a tension limiting mechanism, shown in greater detail in FIGS. 51 and 52. This mechanism limits the amount of tension in the tension line by limiting the amount of torque that can be applied to the gear 670 by the lever 618. The gear 670 is driven by the lever 618 through the spring-biased ball bearing 664 that is mounted in the lever 618. If the force input to the lever 618 is above a predetermined threshold, the force of the spring engagement onto the gear 670 will cause the ball bearing 664 to be pushed back (radially outward from the gear) against the force of the spring 662 and will thus skip teeth 670a on the gear 670. This will cause the lever 618 to rotate about the axis G-G, while the gear 670 remains stationary relative to the base 614 and the cover 616. However, if the force input to the lever 618 is below the predetermined threshold, the ball bearing 664 does not skip teeth 670a of the gear 670 and the lever 618 and the gear 670 will rotate about axis G-G in unison. The predetermined force limit depends on the stiffness of the spring 664, which can be selected based on the intended application for the device 600.

FIGS. 53-57 show an alternative adjustment device 700 similar to the adjustment device 600. The adjustment device 700 differs mainly from adjustment device 600 in that adjustment device 700 includes an elongated spool 712 that is configured for winding tension lines that are flat straps rather than laces or cables that are used with spool 612. In FIGS. 54-63, like elements of adjustment device 600 are shown incremented by "100".

Device 700 has an elongated removable cover 716 with an elongated slot through which the tension line strap can pass to a split axle 724 of the spool 712, shown in greater detail in FIG. 55. As shown in FIG. 55, the spool 712 corresponds to spool 612, but includes an elongated slot 724a to receive and secure the tension line strap to the axle 724. The device 700 includes push buttons 758a and 758b which are used to disengage the ratchet wheels 754a (FIG. 59) and 754b (FIG. 56), in the same way buttons 658a and 658b are used to disengage ratchet wheels 654a and 654b, to permit the spool 712 to freely rotate to unwind.

Figure 60:
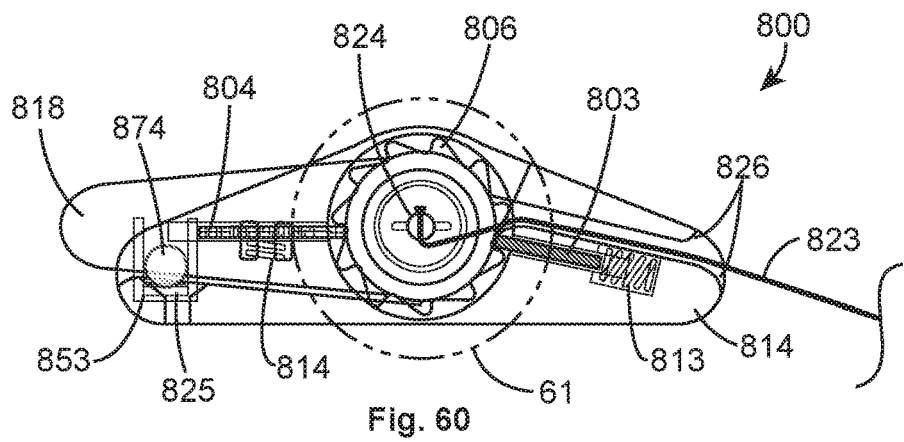
FIG. 60 is a transparent side elevation view of another embodiment of a tension device in accordance with an aspect of the disclosure.
Figure 61:
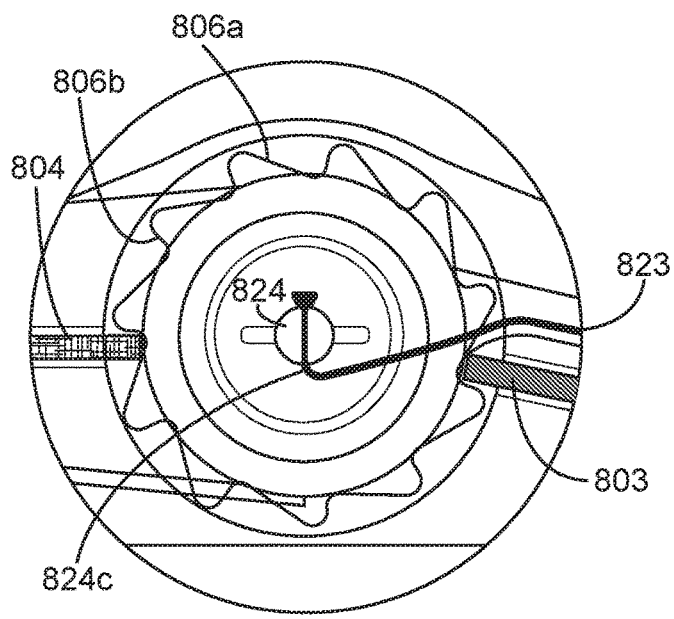
FIG. 61 is a detailed view of the detail E in FIG. 60.
Figure 62:
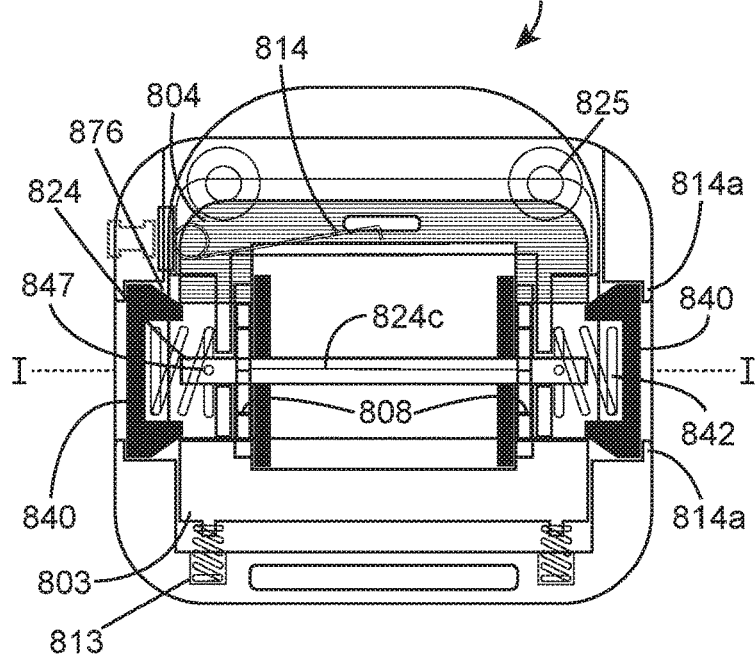
FIG. 62 is a plan view of the tension device shown in FIG. 62.
Figure 63:
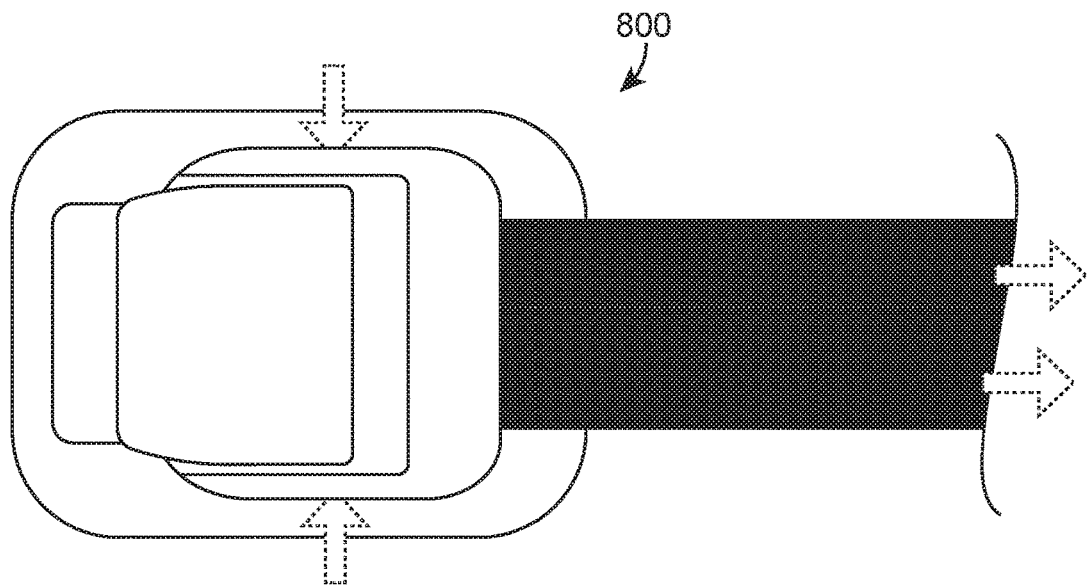
FIG. 63 shows the tension device of FIG. 62 connected to a tension line with solid outlined arrows showing a direction of application of forces to the tension device to release tension in the tension line of the device, allowing the tension line to move in the direction of broken line arrows.

FIGS. 60-64 relate to an adjustment device 800 that includes a base 814, a lever 818, pivotally connected to the base 814, and spool 812 pivotally connected to the base 814. The spool 812 includes an axle 824 and two longitudinally spaced gears 806 fixed to the axle 824. The gears 806 have rounded one-way slopping gear teeth with a coast side 806a and a drive side 806b. The axle 824 extends longitudinally along axis I-I (FIG. 62). The axle 824 defines a longitudinal slot 824c, which is compressible about a tension line strap 823 to substantially secure the strap 823 to the axle 824 as shown in FIGS. 60 and 61. A retaining pin 847 is shown and is utilized in this embodiment to retain the lever 818 around the gears 806.

The device 800 includes a ratcheting strap advancement mechanism comprising a lever arm-mounted ratchet advancement tab 804 and a base-mounted tab 803. The tabs 804 and 803 are configured to engage the gears 806 of the spool 812. Both the lever arm tab 804 and the base mounted tab 803 are biased into the gears 806 such that the tabs (803 and 804) are pushed into the teeth of the gears 806 such that the tabs 803 and 804 block the gears from retraction when the adjustment device user wishes to wind the strap 823 under tension. The lever arm tab 804 is biased by a torsional spring 814 (FIG. 62) and the base mounted tab 803 is biased by helical compression springs 813 (FIG. 62). The springs 814 and 813 urge the tabs 804 and 803 radially inwardly (with respect to axis I-I) into engagement with the teeth of gears 806.

As the lever 818 is rotated relative to the base 814 about axis I-I in a first direction (in FIG. 60, gear rotation is in a clockwise direction although the rotation is in the counterclockwise direction when viewed from the other side of the device from that shown in FIG. 60), the lever arm tab 804 catches the drive side 806b of the gears 806 and thereby rotates the gears 806 and axle 824 about the base 814 in the first direction. When the lever arm 818 is rotated in a second direction opposite the first direction (counterclockwise in FIG. 60), the base mounted tab 803 engages the drive side 806b of the gears 806 and blocks the gears 806 from reversing rotational direction while the lever arm tab 804 skips over the coast side 806a of the gears 806, which has a gradual slope that pushes the lever arm tab 804 away from the gear 806 against the force of the spring 814 until the tab 804 passes the gear tooth and clicks down into the space between the gear teeth. A repeating clicking noise occurs as the lever arm tab 804 skips over the teeth of the gears 808 as the lever 818 rotates about the base 814 in the second direction.

The adjustment device 800 provides significant mechanical advantage for the user to wind the tension line strap 823 in applications where the device 800 is coupled to a wearable article or otherwise used to fit about the body of a human or animal. The mechanical advantage of this device is provided, in part, by the length of the lever 818, which, in the illustrated embodiment, is approximately 33 mm long and is approximately 26 mm from the end of the lever 818 to the center of the axle 824. The lever 818 could be made longer to provide more mechanical advantage, but the overall profile and bulk of the adjustment device 800 would also increase as well. Moreover, a longer lever 808 may increase the chance for inadvertent rotation of the lever 818 and winding of the strap 823. Furthermore, without being bound by theory, it is believed that that the length of the lever 818 in combination with the base 814, gears 808, and gear teeth (in terms of teeth size and number of teeth) is preferred for applications fitting to the body wherein a human user can create a suitable amount of tension and resulting load in the tension line 823, but not an excessive amount that could be detrimental to circulation or otherwise inappropriate.

The device 800 includes a mounting mechanism for the base 814 wherein the base can be fastened to an article. As shown in FIG. 60 the base 814 defines a plurality of countersunk holes 825 which are designed to receive fasteners (not shown) for fastening the base 814 to an article. The fasteners are designed to be accessible for assembly by advancing the lever arm 818, but to be concealed (as in FIG. 60) under the lever arm 818 for visual simplicity.

The adjustment device 800 also includes a collection funnel mechanism which is shown as rounded edges 826 (FIG. 60) where the tension line strap 823 enters and exits the base 814. The rounded edges 826 aid in collecting and organizing the strap 823 as it is drawn toward and around the collecting axle 824 or is released from it. Furthermore, the rounded edges 826 help to reduce abrasion of the strap 823 by the base 814 during use.

The device 800 includes a release mechanism that allows the user to quickly and easily simultaneously release both the lever arm tab 804 and the base mounted tab 803 from the spool 812 with one hand. The release mechanism of device 800 can be better viewed from the top and is demonstrated in further detail in FIGS. 62-64. FIG. 62 shows release buttons 840 and helical compression springs 842 for the release buttons 840 on opposite sides of the base 814. The release buttons 840 and springs 842 are coaxial with the axle 824. The springs 842 bias the release buttons 840 back away from the lever arm tab 804 and away from the base mounted tab 803. Each release button 840 has a circumferential tab 828 with a tapered cam surface 876 that engages the tabs 804 and 803. The base 814 includes retention tabs 814a that abuts the outer sides of the release buttons 840 to retain the release buttons 840.

Figure 64:
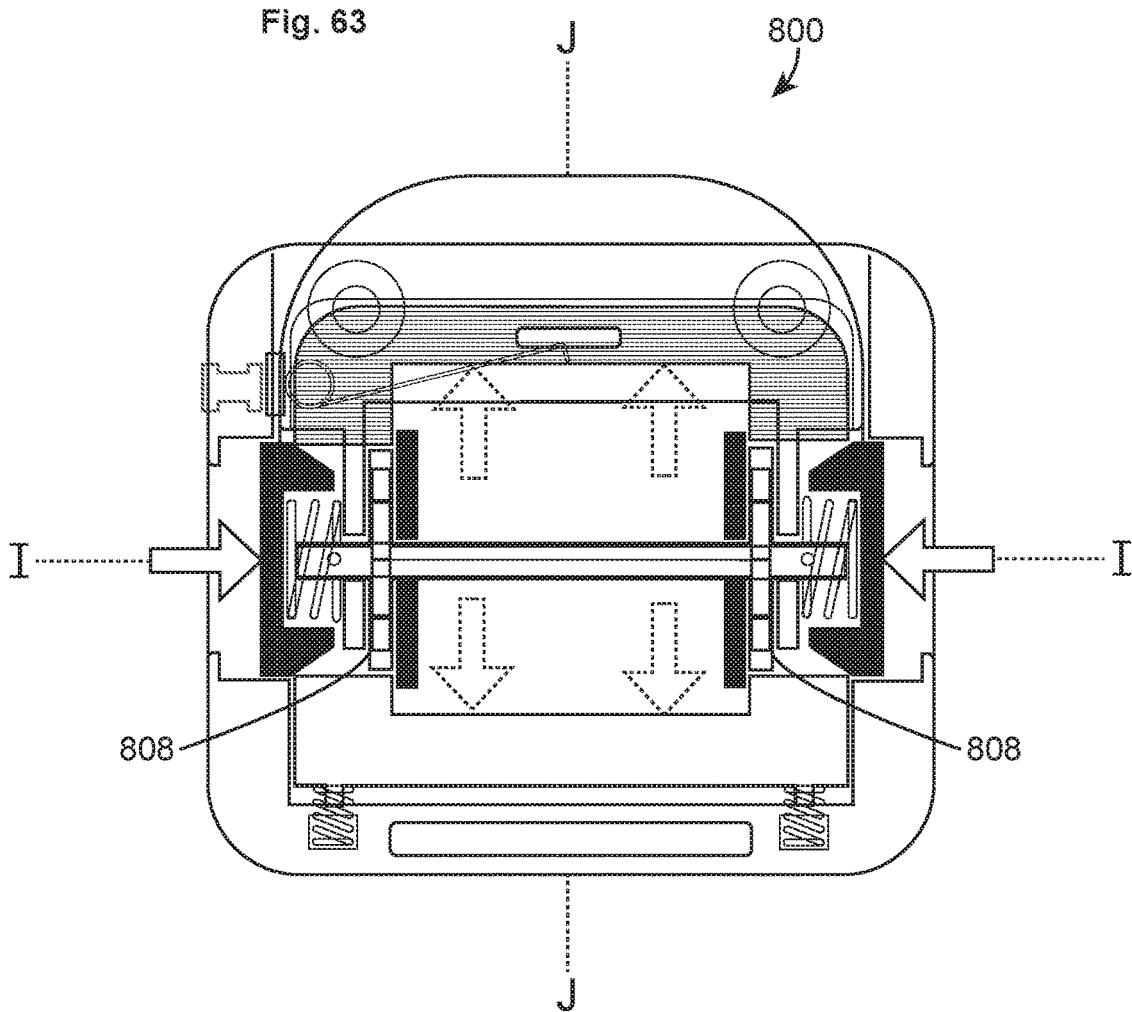
FIG. 64 shows the tension line of FIG. 63 after forces are applied to the tension device to release the tension line.

FIG. 62 show a detailed view of one of the release buttons 840 in a first position where the buttons 840 are in contact with the retention tabs 814a. FIG. 64 demonstrates how the base mounted tab 803 and the lever arm tab 804 can be simultaneously disengaged from the gears 806 by pushing both release buttons 840 in the direction of the arrows along axis I-I. As the buttons 840 are pushed in, the tapered cam surface 876 of the circumferential tabs 828 slide against edges of the tabs 803 and 804 to spread the tabs 803 and 804 outwardly along an axis J-J perpendicular to axis I-I in the direction of arrows.

The device 800 also provides a lower profile solution than the split axis and manual feeding strap axis solution presented in the prior art. In this embodiment, the axle 824 is fabricated as two separate halves that are assembled together when coupled with the gears 808 on both sides of the axle 824. When the two halves of the axle 824 are joined together and coupled with a gear 808 on each side, a strap 823 with melted or otherwise expanded end (such as including a small retention pin at the end of the strap) is placed between the halves of the axle 824. The strap 824 is thereby pinched in between the halves of the axle 824 and retained. This arrangement would also allow for the gear to be on the outside of the lever 818 and base 814.

The release mechanism and method described herein allows a user to quickly and easily release both the lever arm tab 804 and the base mounted tab 803 simultaneously with one hand, which thereby allows the spool 812 to unwind partially or fully, if desired. The method to release the strap in the prior art included the need to use two hands in a multi-step process that also required a separate tab release. In order to release adjustment device 800, the user need only press both release button 840 at the same time with one hand, by way of the ergonomic and strong pinch motion that humans can easily do with one hand, for example, with their thumb and index finger. The use of a two-finger or two-button release using a pinching motion release also helps to avoid unintentional release of the system.

It is also notable that the release buttons 840 can be pushed to release the spool 812 when the lever 818 is in any rotational position relative to the base 814. This ability for the user to release the tension line 823 from any position in an ergonomic way and with ease while also offering a mechanism that is unlikely to inadvertently release provides distinct advantages over the prior art for devices and garments fitting the body.

Turning back to the side view of the device 800 shown in FIG. 60, the lever 818 is shown in a first rest position in a recessed location at one end 814b of the base 814. It will be appreciated that due to the shape of the base 814, the lever 818 may also be recessed when rotated in position at a second end 814c of the base 814, thereby offering a reversible device and the ability for the user to rest the lever 818 in whatever position is best for the user and the particular application.

The device 800 has a tension line collection volume defined between the base 814 and the axle 824. The collection volume is used to store the tension line 823 as the axle 824 winds the tension line 823. The device 800 also includes a lever arm safety catch and release mechanism 874 (FIG. 60), which in this embodiment includes a leaf spring with barbed feature to catch on the matching mechanical catch 853 set in the base 814.

Figure 65:
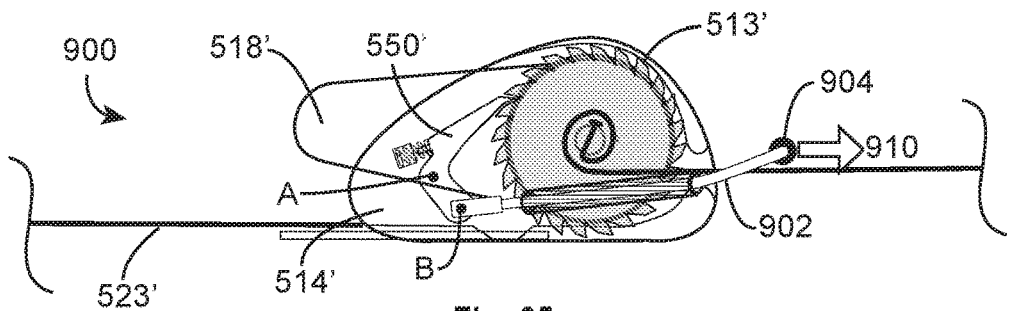
FIG. 65 is a transparent side elevation view of another embodiment of a tension device in accordance with an aspect of the disclosure.

FIG. 65 shows a partially transparent (right side) view of an embodiment of an adjustment device 900 having a release mechanism configured with a front side pull release. Other than the alternative release mechanism, the FIGS. 65-68 use the same adjustment mechanism as the single adjustment embodiment shown in FIGS. 39A-39B. However, the same release mechanism that is highlighted in device 900, is also applicable to the dual adjustment mechanism of FIGS. 40A to 40D. For ease of illustration and by way of example, FIGS. 65-68 refer to features of device 500'

FIG. 65 shows ratchet pawl 550' pivotally connected to the base 514' at A to creating a one-way rotation degree of freedom between the base 514' and the axle 524'. The pawl 550' shown has a lever arm extending from A to a second pivotal connection at B. The pawl 550' is pivotally connected to a release cable 902 at B. The cable 902 includes an ergonomic handle 904 or catch for hand or hook single action pull release. The cable transfers pull force to the pawl 550' by way of a tunnel 906 through the base 514'. If the release cable 902 is pulled to the front (in the direction of arrow) via handle 904, it will cause the pawl 550' to rotate about B and A to disengage the pawl 550' from the ratchet gear 513'. It will be appreciated that the handle 904 transmits a force in a direction of the arrows shown in FIG. 65. This force can also be imparted to the pawl 550' at B if the force was imparted on a side of the housing opposite the handle 904.

Figure 66:
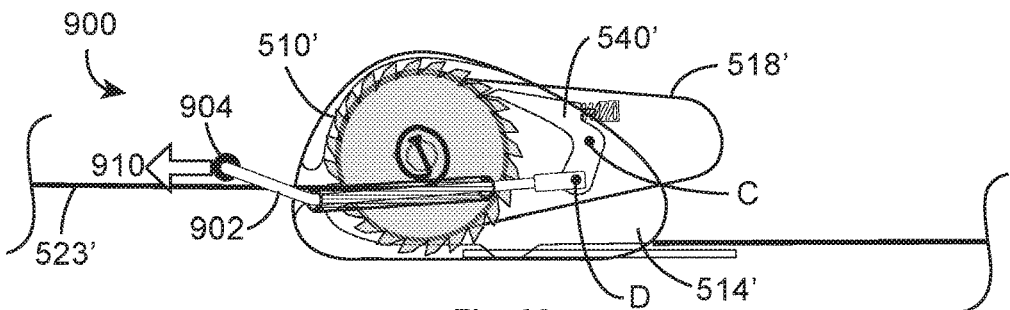
FIG. 66 shows the device of FIG. 65 from an opposite side.

FIG. 66 shows an opposite side of the device 900 shown in FIG. 65. Specifically, FIG. 66 shows ratchet pawl 540' pivotally connected to lever 518' at C. The pawl 540' is also pivotally connected to the release cable 902 at D. The cable 902 must move with the rotation of the lever 518' during winding and retraction of the lever 518'. This movement of the cable 902 is accommodated by routing the cable path from the handle 904 to D near the axis (F-F) of rotation of the lever 518' such that the cable 902 does not need to move excessively to accommodate the motion of the lever 518'. If the release cable 902 is pulled to the front (in the direction of the arrow) via handle 904, it will cause the pawl 540' to rotate about D and C to disengage the pawl 540' from the driven gear 510'.

Figure 67:
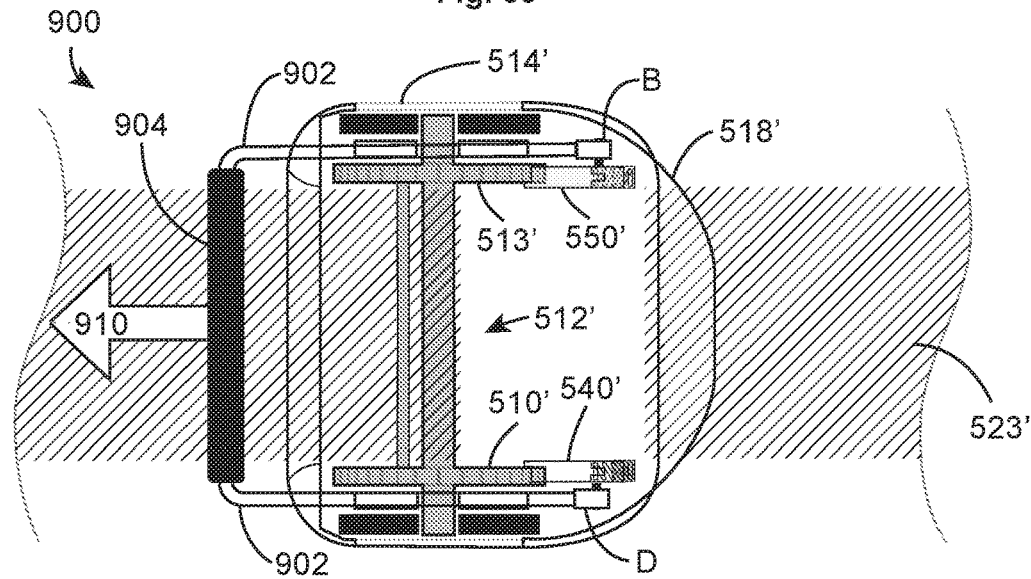
FIG. 67 is a plan view of the device of FIG. 65.
Figure 68:
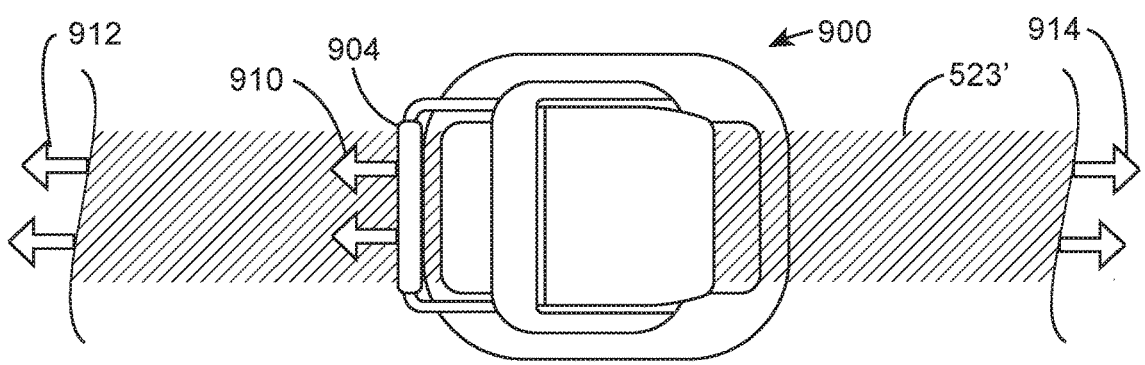
FIG. 68 shows a single-handed pulling movement to pull on a release handle in a direction of solid-line arrows.
Figure 69:
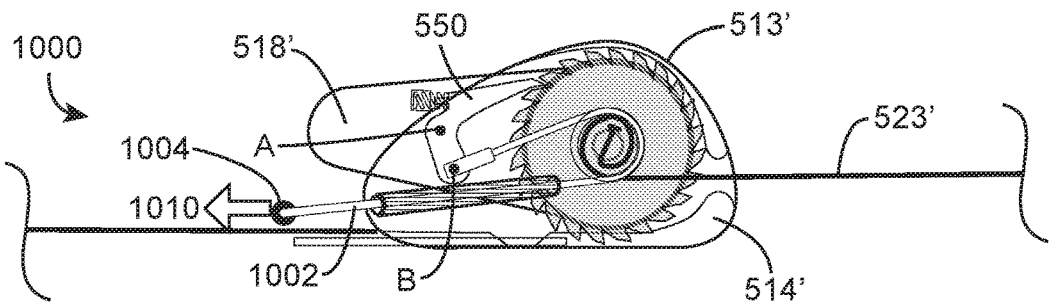
FIG. 69 is a transparent side elevation view of another embodiment of a tension device in accordance with an aspect of the disclosure.
Figure 70:
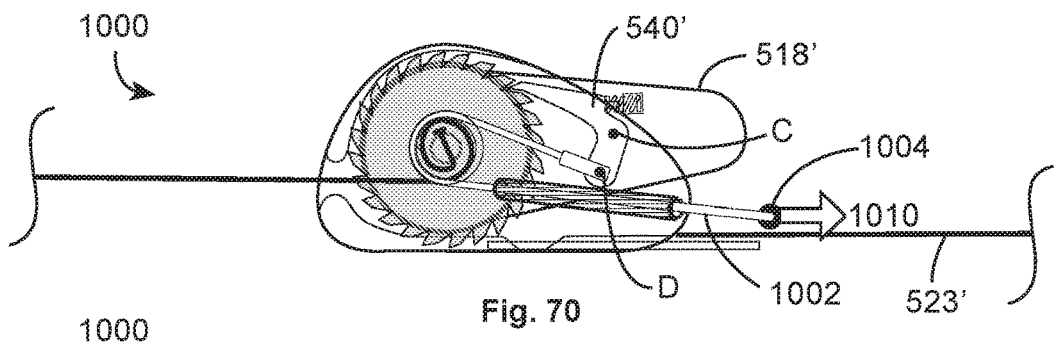
FIG. 70 shows the device of FIG. 69 from an opposite side.

FIG. 67 shows a transparent top view of the device 900 shown in FIG. 65. FIG. 68 shows the motion (a pulling hand gesture) that a user of the device would take to release the spool 512'. FIG. 67 shows that as the handle 904 is pulled forward in the direction of the arrow 910, the cables 902 on both sides of the spool 512' release both pawls 540' and 550' simultaneously, thereby allowing the axle 524' to spin independently from the base 514' and the lever 518'. With tension in the tension line strap 523' the release of the spool 512' will thus naturally cause the tension line strap 523' to unwind out of the spool 512'. The arrows 910 in FIG. 68 show application of the required release force to the handle 904. Arrows 912 show the direction of extension of the tension line 523' in a single adjustment embodiment, whereas arrows 912 and 914 show the direction of extension of the tension line 523' in a dual adjustment embodiment.

Figure 71:
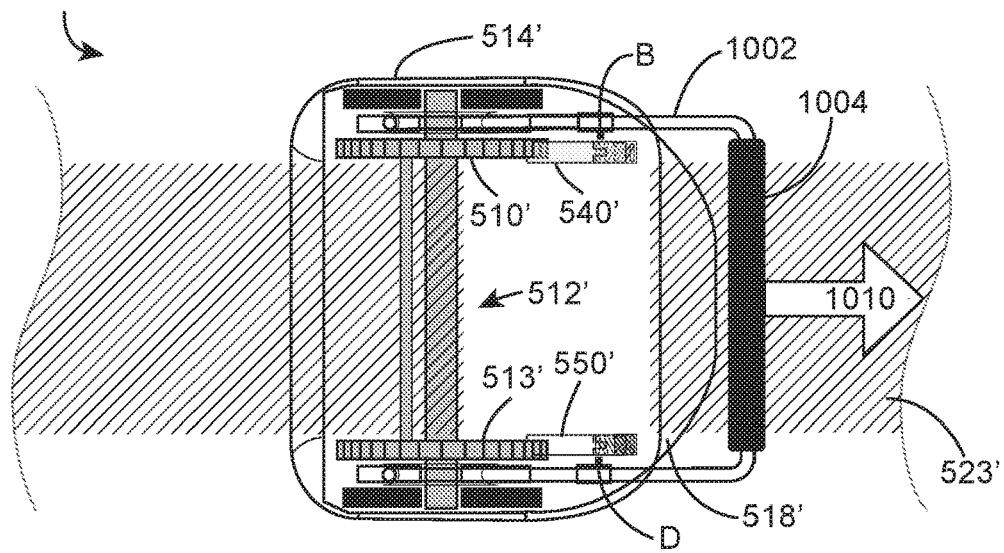
FIG. 71 is a plan view of the device of FIG. 69.

FIGS. 69-72 show embodiments of an adjustment device 1000 with a single-action, back-side pull release. FIGS. 69-72 refer to features of the device 500'. FIGS. 69-72 show an embodiment of an adjustment device 1000 having a release mechanism that includes a back-side pull release cable 1002 and a handle 1004. The release cable 902 is routed from the back around approximately 180 degrees to B on pawl 550' and to D on pawl 540'. Thus, the cable routing transmits rearward force on the handle 1004 to forward directed force acting on the pawls 550' and 540'. FIG. 71 shows a transparent top view of the device embodiment shown in FIGS. 69-70. In view of the routing of the release cable 1002 to the pawls 550' and 540' shown in FIG. 76, both pawls 550' and 540' are configured to simultaneously disengage from the gears 513' and 510'.

Figure 72:
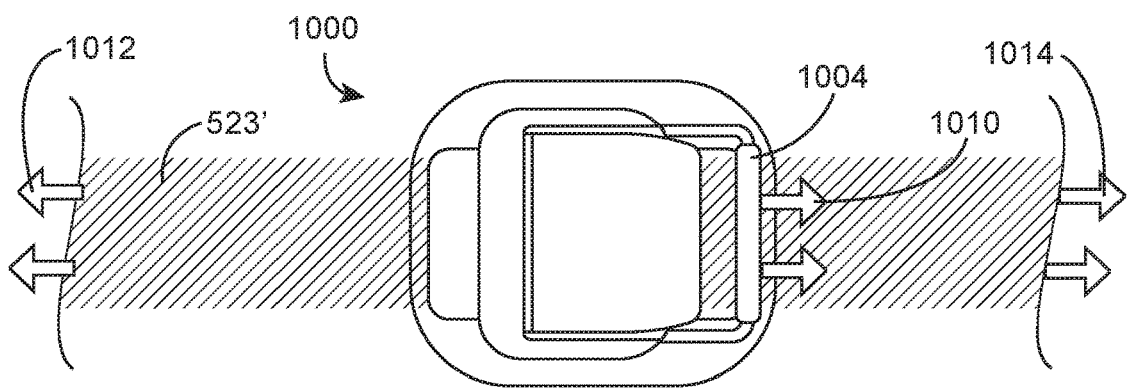
FIG. 72 shows a single-handed pulling movement to pull on a release handle in a direction of solid-line arrows.

FIG. 72 shows a top view of the device 1000 and demonstrates the hand motion that a user would take to release the device 1000, by pulling the handle 1004 in the direction of arrows 1010. The strap or cable 523' would then release out of the spool 512' as described above if there is tension in the system, which is depicted by the arrows on the strap in FIG. 72. The arrows 1010 in FIG. 72 show application of the required release force to the handle 1004. Arrows 1012 show the direction of extension of the tension line 523' in a single adjustment embodiment, whereas arrows 1012 and 1014 show the direction of extension of the tension line 523' in a dual adjustment embodiment.

FIGS. 73-76 show an adjustment device 1100 having release cables 1102, 1103 connected between a rotatable knob 1104 and pawls 540' and 550' to transfer pull force to simultaneously pull the pawls out of engagement with mating gears 510' and 513' in a single action by rotating the knob 1104 (e.g., counterclockwise in these examples).

Figure 73:
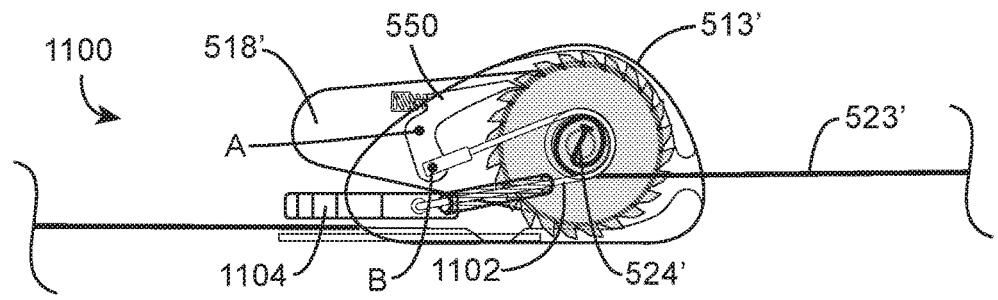
FIG. 73 is a transparent side elevation view of another embodiment of a tension device in accordance with an aspect of the disclosure.
Figure 74:
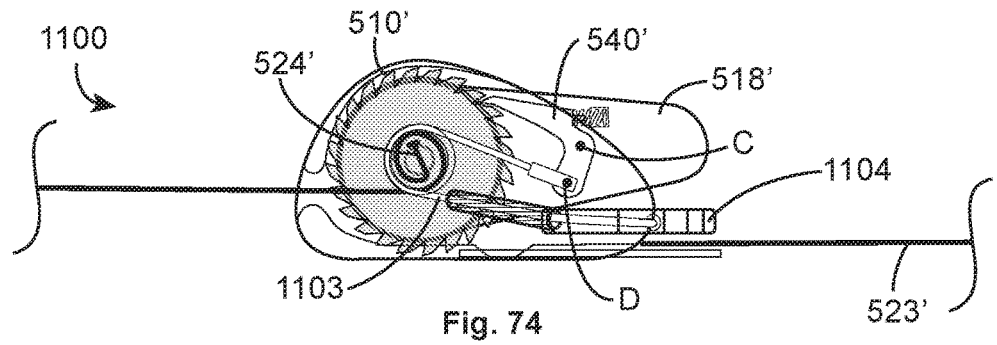
FIG. 74 shows the device of FIG. 73 from an opposite side.

FIG. 73 shows pawl 550' pivotally connected to the base 514' at A and to cable 1102 at B. The cable 1102 is routed rearward over and around axle 524' approximately 180 degrees to rotatable knob 1104. FIG. 74 shows pawl 540' pivotally connected to lever 518' at C and to cable 1103 at D. The cable 1103 is routed rearward over and around axle 524' approximately 180 degrees to rotatable knob 1104.

Figure 75:
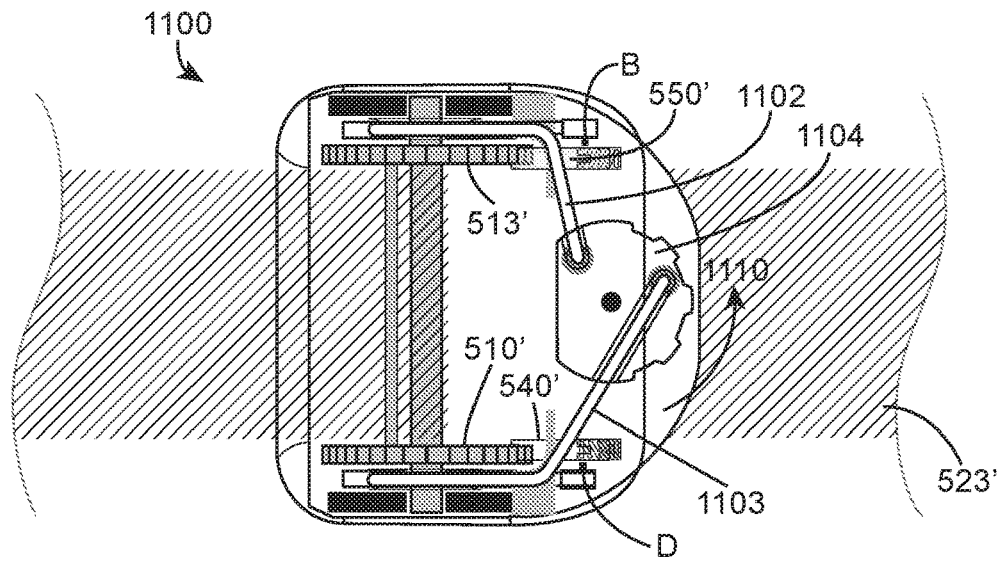
FIG. 75 is a plan view of the device of FIG. 73.

FIG. 75 shows a partially transparent top view of the device 1100 in a neutral state where the pawls 540' and 550' are fully engaged with the gears 510' and 513', respectively. The knob 1104 defines internal pathways for routing cable 1102 to pivot E and for routing cable 1103 to pivot F. The internal pathways increase leverage on the cables 1103 and 1102 when the knob 1104 rotates in the direction of arrow A in FIG. 80. If the knob 1104 is rotated in the direction of arrow 1110, both tension lines 1102 and 1103 will pull in the same direction (e.g., to the right in FIG. 80) simultaneously, thereby pulling on and disengaging the pawls 540' and 550' at the same time.

Figure 76:
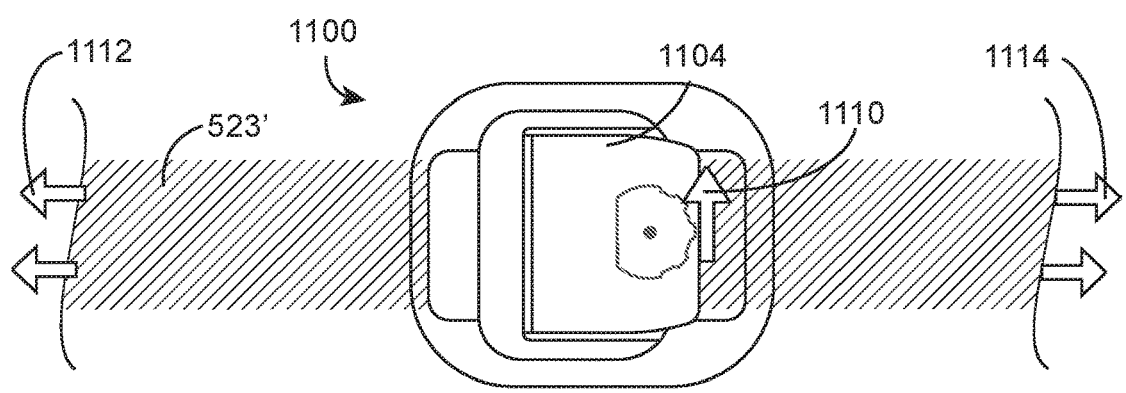
FIG. 76 shows a single-handed sliding movement to rotate a release knob in a direction of solid-line arrows.

FIG. 76 shows a method of releasing the device 1100 by way of rotating the knob 1104 using one finger. The arrow 1110 in FIG. 76 shows application of the required release force to the knob 1104. Arrows 1112 show the direction of extension of the tension line 523' in a single adjustment embodiment, whereas arrows 1112 and 1114 show the direction of extension of the tension line 523' in a dual adjustment embodiment.

FIGS. 77-80 show an embodiment of an adjustment device 1200 having release lines 1202 and 1203, connected between a lever 518' and pawls 540' and 550', that transfer tension to pull pawls 540' and 550' out of engagement with gears 510' and 513', respectively.

Figure 77:
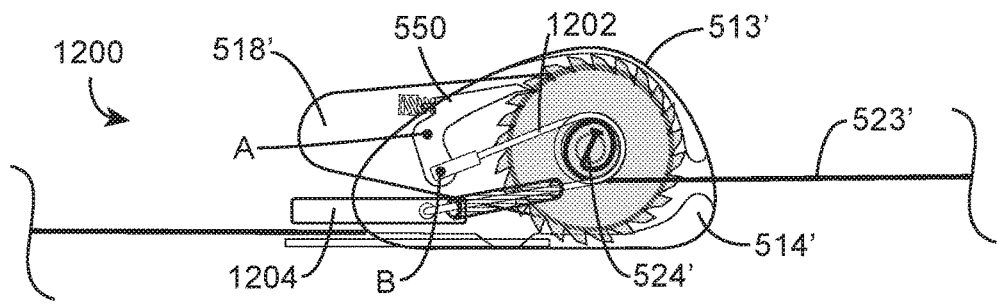
FIG. 77 is a transparent side elevation view of another embodiment of a tension device in accordance with an aspect of the disclosure.
Figure 78:
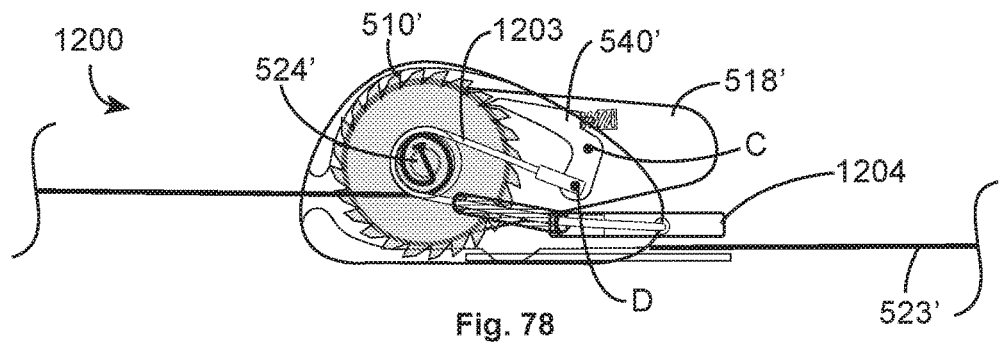
FIG. 78 shows the device of FIG. 77 from an opposite side.

FIG. 77 shows pawl 550' pivotally connected to base 514' at A and to cable 1202 at B. The cable 1202 is routed rearward over and around axle 524' approximately 180 degrees to rotatable lever 1204. FIG. 78 shows pawl 540' pivotally connected to lever 518' at C and to cable 1203 at D. The cable 1203 is routed rearward over and around axle 524' approximately 180 degrees to rotatable lever 1204.

Figure 79:
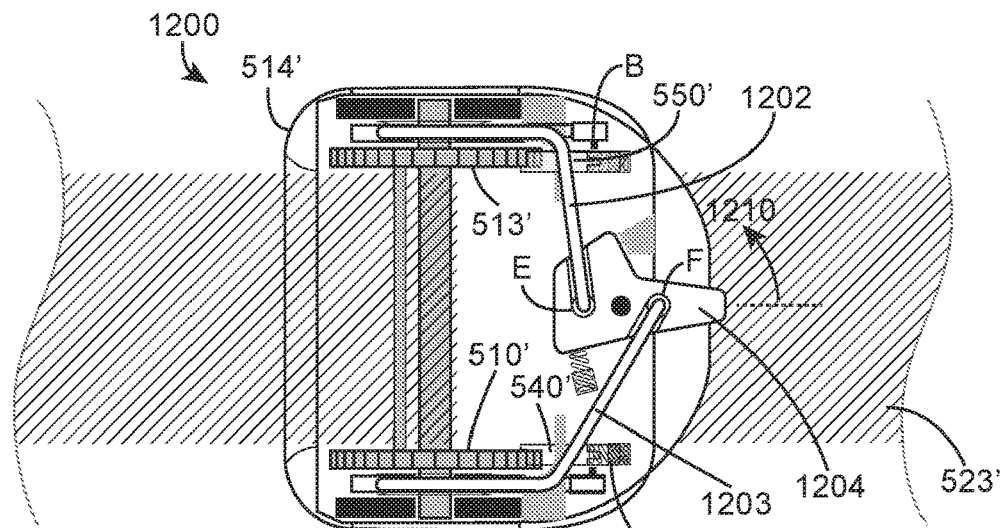
FIG. 79 is a plan view of the device of FIG. 77.

FIG. 79 shows a partially transparent top view of the device 1200 in a neutral state where the pawls 540' and 550' are fully engaged with the gears 510' and 513', respectively. The lever 1204 defines internal pathways for routing cable 1202 to pivot E and for routing cable 1203 to pivot F. The internal pathways increase leverage on the cables 1203 and 1202 when the lever 1204 rotates in the direction of the arrow in FIG. 79. If the lever 1204 is rotated in the direction of the arrow 1210, both tension lines 1202 and 1203 will pull in the same direction (e.g., to the right in FIG. 79) simultaneously, thereby pulling on and simultaneously disengaging the pawls 540' and 550'.

Figure 80:
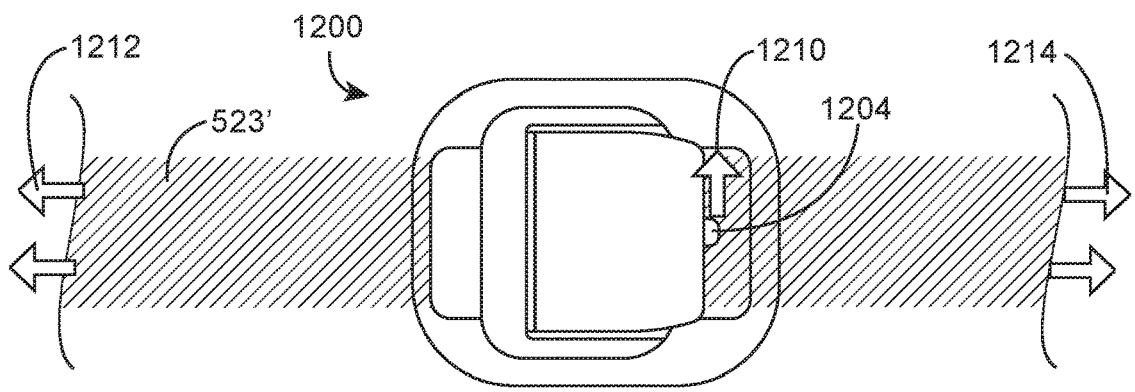
FIG. 80 shows a single-handed sliding movement to rotate a release lever in a direction of solid-line arrows.

FIG. 80 shows a method of releasing the device 1200 by way of rotating the lever 1204 using one finger. The arrow 1210 in FIG. 80 shows application of the required release force to the lever 1204. Arrows 1212 show the direction of extension of the tension line 523' in a single adjustment embodiment, whereas arrows 1212 and 1214 show the direction of extension of the tension line 523' in a dual adjustment embodiment.

Figure 81A:
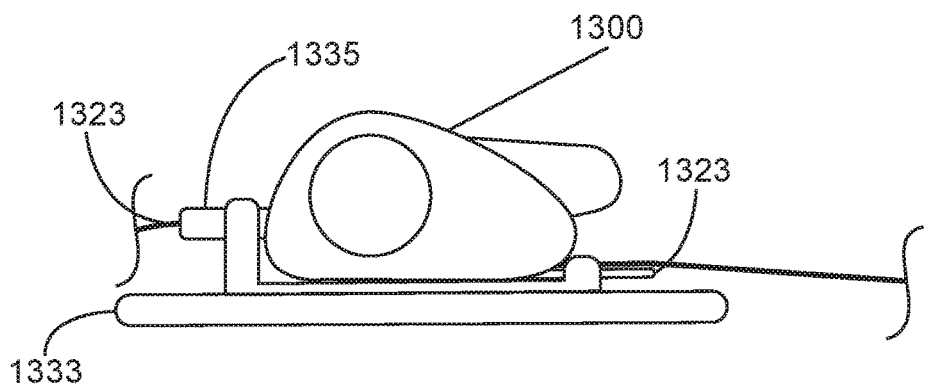
FIG. 81A is a side elevation view of an embodiment of a tension device mounted on a pressure distribution pad.
Figure 81B:
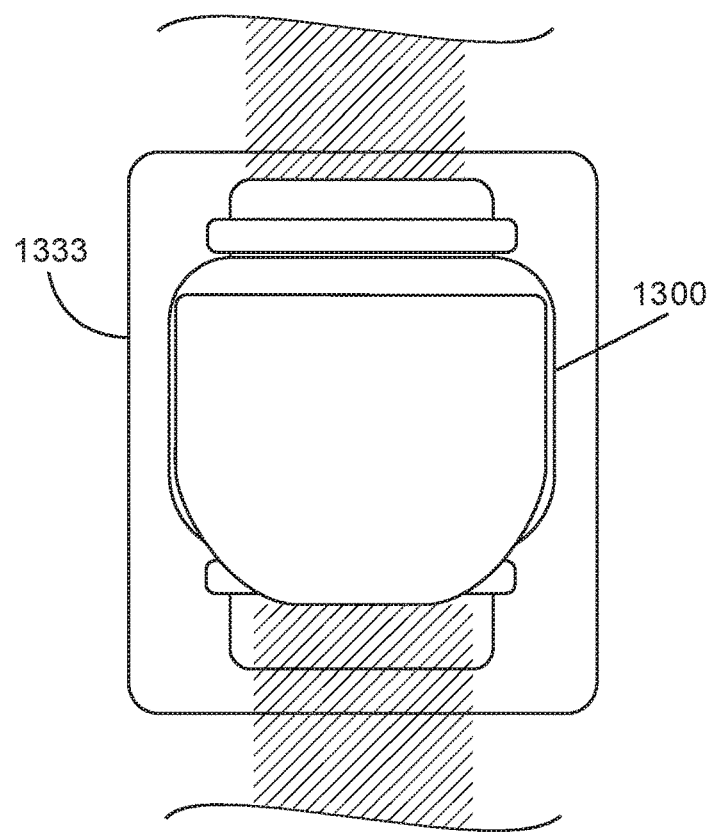
FIG. 81B is a plan view of the device and pressure distribution pad of FIG. 81A.
Figure 81C:
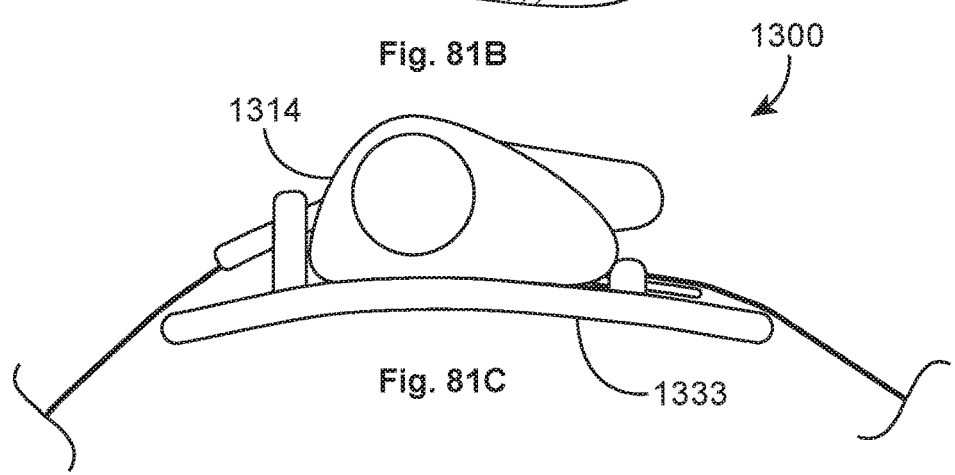
FIG. 81C shows an alternate configuration of the tension device and pressure distribution pad of FIG. 81A where the pressure distribution pad and housing can be bent or curved to accommodate connection or mounting to a curved surface.

FIG. 81A shows a fit system 1301 that includes an adjustment device 1300, a tension line 1323, and a pressure distribution pad 1333 that can be positioned below the adjustment device 1300, interfacing between the adjustment device 1300 and a surface, which may be a curved surface such as a surface of a human or animal body or an article conforming to a human or animal body surface. As shown in FIG. 81C, the pressure distribution pad 1333 may be curved a curved to correspond more closely with the curvature of a surface to which the pad is mounted.

Pressure distribution of the fit system may relate to the load delivered, surface area, geometry or shape of the fit system, and/or rigidity of fit system components. The amount of load onto the body applied by a fit system divided by the surface area of the applied load will yield a given pressure distribution. For most applications that require a high-tension fit system (tension over 100 lbs.), it is recommended that associated loads be distributed onto straps over 1.5" in width or which have a surface area of at least 8 square inches. For example, a fit system that is low in profile and includes a contour that matches the body it is applied to, has tapered rigidity of its members wherein the system becomes less rigid near the edges, and has rounded edges. One important aspect of the fit system shape is how well the contour of the pressure distribution pad 1333 matches the natural curvatures of the body or how well it can conform to that shape such that pressure can be evenly distributed over the body. Another important aspect of the shape is how sharp or blunt (the radius) the edges are of the fit system members. Edges that are too sharp can lead to peak pressures that could result in discomfort, bruising, or skin abrasion.

Figure 82:
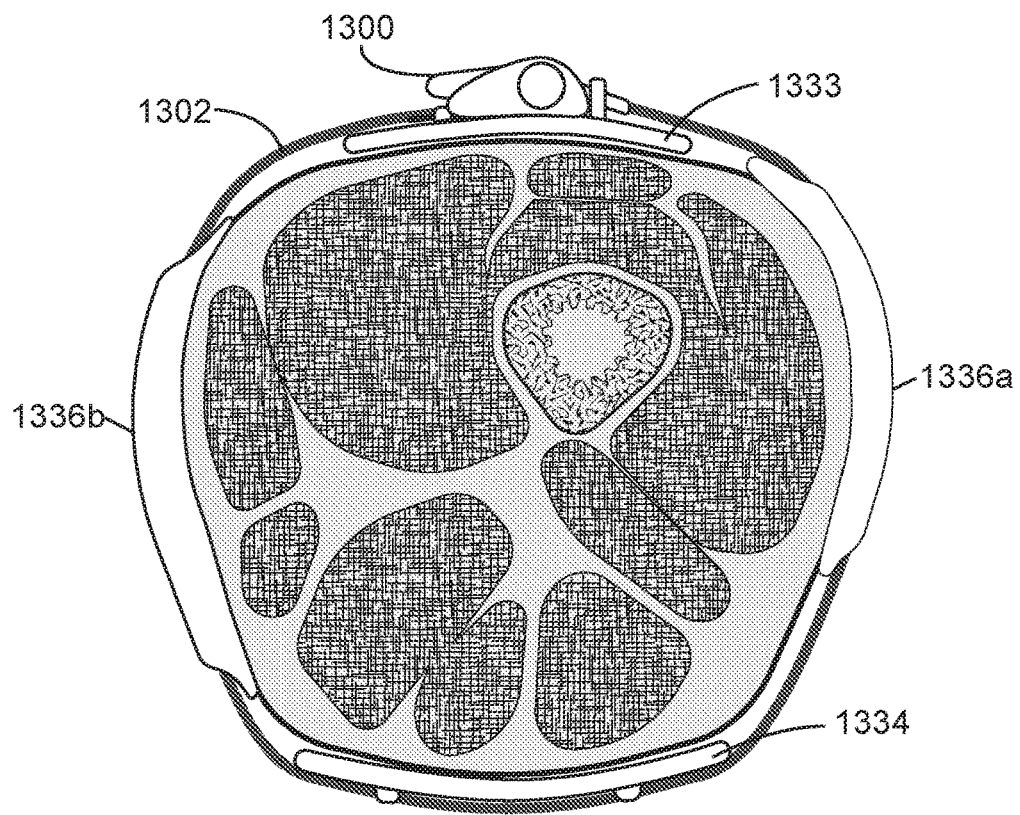
FIG. 82 is a view of a fit system comprised of the tension device of FIGS. 81A-81C and a tension line banded about a leg along line 82-82 in FIG. 83.
Figure 83:
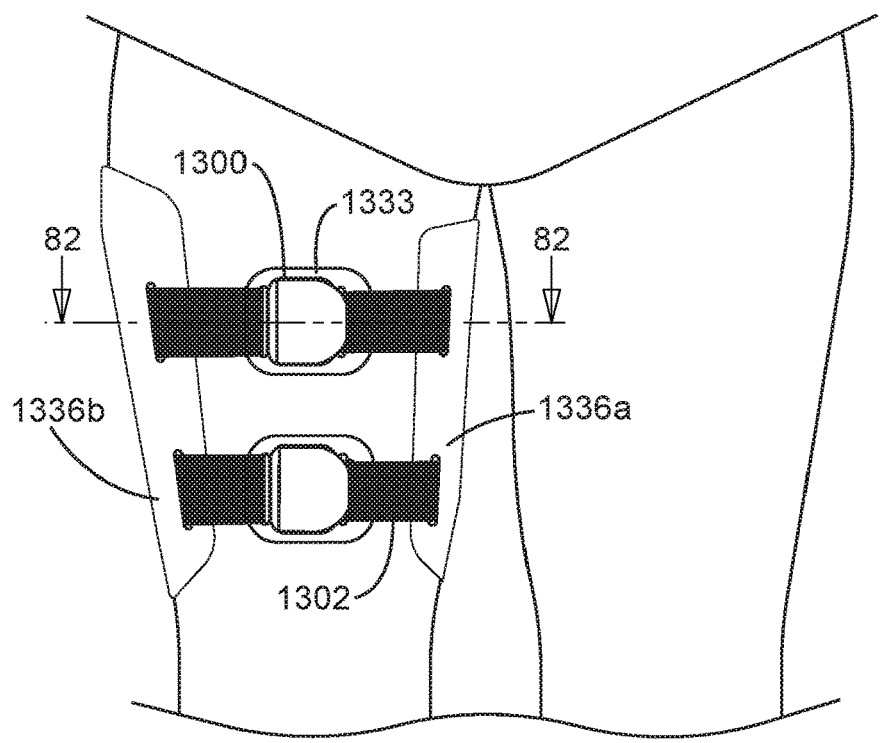
FIG. 83 show an example use of fit systems using the tension devices of FIGS. 81A-81C with tension lines banded about a leg.
Figure 84:
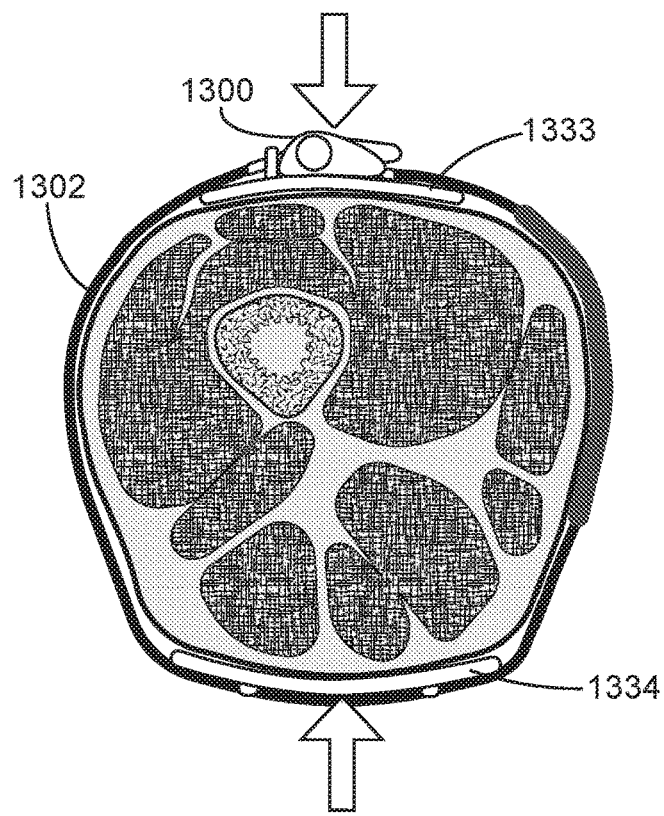
FIG. 84 illustrates with broken line arrows the direction of forces applied using the pressure distribution pads.

By way of example, FIGS. 82 and 83 show the adjustment device 1300 and pressure distribution pad 1333 banded about a user's leg with the adjustment device 1300 and pad 1333 positioned on the front of the leg. Also, as shown in FIG. 82, an additional pressure distribution pad 1334 is located on the back side of the leg between a strap 1302 and the leg to distribute pressure to the leg. In addition, pressure distribution pads 1336a and 1336b are located on the inner and outer sides of the leg, respectively. The pads 1334, 1336a, and 1336b may be relatively low in durometer. Pressure distribution pads 1336a and 1336b have a low durometer inner surface and a semi-rigid shell that define a channel for strap 1302 to pass between the inner and outer surfaces (inner and outer being relative to outer surface of the leg) of the pads 1336a, 1336b. In the embodiment shown in FIGS. 82 and 83, strap tension is not distributed directly onto the body (e.g., the leg). Instead, strap tension and resulting forces from strap tension are distributed indirectly through pressure distribution pads 1334, 1336a, and 1336b. As force equals pressure divided by area, resultant forces of this fit system are reduced by increasing the surface area of pressure distribution. As shown in FIG. 84, the pressure distribution pads 1333 and 1334 cause the tensile forces in the strap 1302 to direct compressive forces in the direction of the arrows in FIG. 84.

Figure 85:
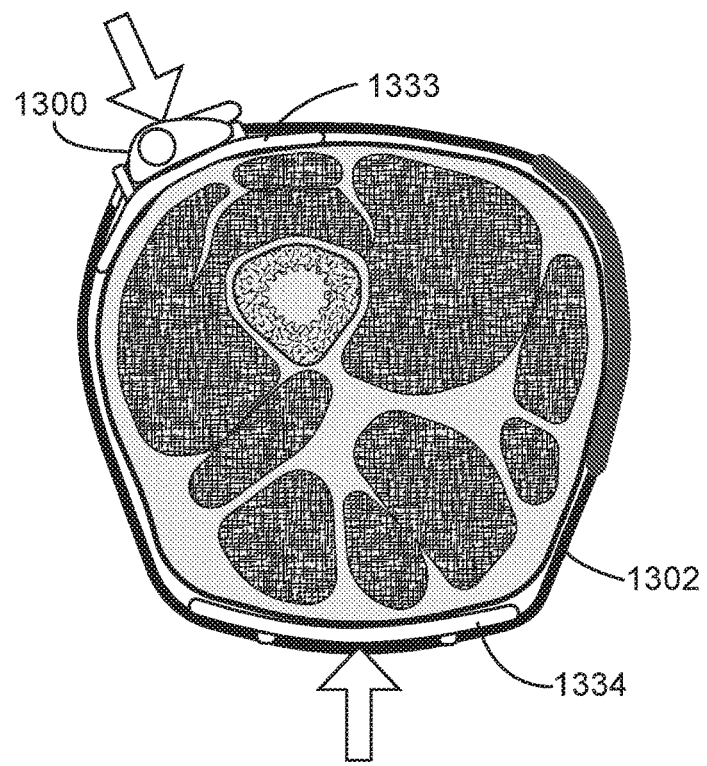
FIG. 85 illustrates with broken line arrows the direction of forces applied using the pressure distribution pads when the tension device is shifted to a rounded corner of the leg.

In FIG. 85 the location of the adjustment device 1300 and pressure distribution pad 1333 is shifted to a more curved portion of the leg. In the embodiment shown in FIG. 85, the pressure distribution pad 1333 is flexible and therefore bends to match the curvature of the leg. The ability for many of the adjustment devices herein to slide along the length of the tension line (e.g., strap) while the tension is loose can be made possible by fixing the tension line on either side of the tension line and passing the tension line continuously through the spool of the adjustment device. Such embodiments can permit selective placement of the adjustment device (as shown in FIGS. 84 and 85) for device adjustment in order to maximize comfort and/or improve performance or convenience.

Figure 86:
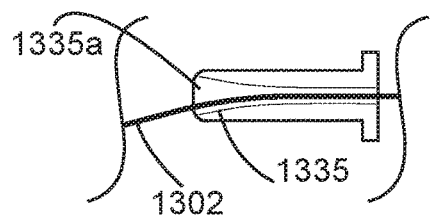
FIGS. 86-88 show details of a tension line collection funnel of the tension device of FIGS. 81A-81C.
Figure 87:
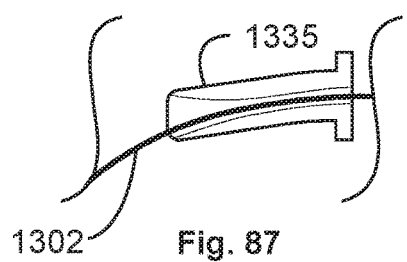
Figure 88:
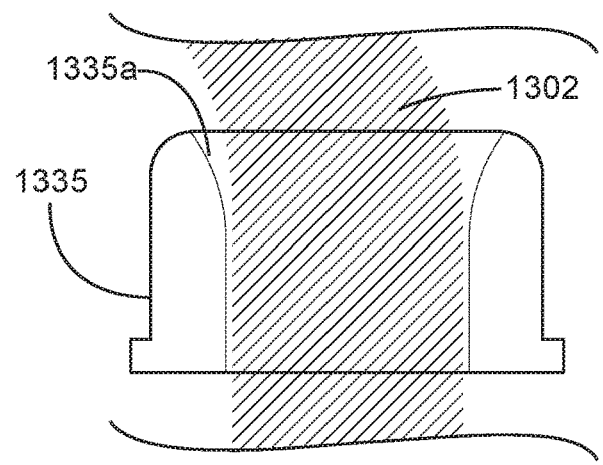

FIGS. 86-88 show details of a collection feeder 1335 shown in FIG. 81A. This particular embodiment is shown with a tensioning line 1302 in the form of a strap, but it could also be applicable to a tensioning line in the form of a cable.

FIG. 86 shows a transparent side view of a tensioning line collection guide or funnel 1335 for the adjustment device 1300. Collection guide 1335 guides the tension line 1302 into and out of the housing of the adjustment device 1300. As shown in FIG. 99, the guide or funnel 1335 has a flared outer opening. Also, as shown in FIG. 87, the collection funnel 1335 is flexible and can bend in response to forces applied by the tension line 1302.

Figure 89:
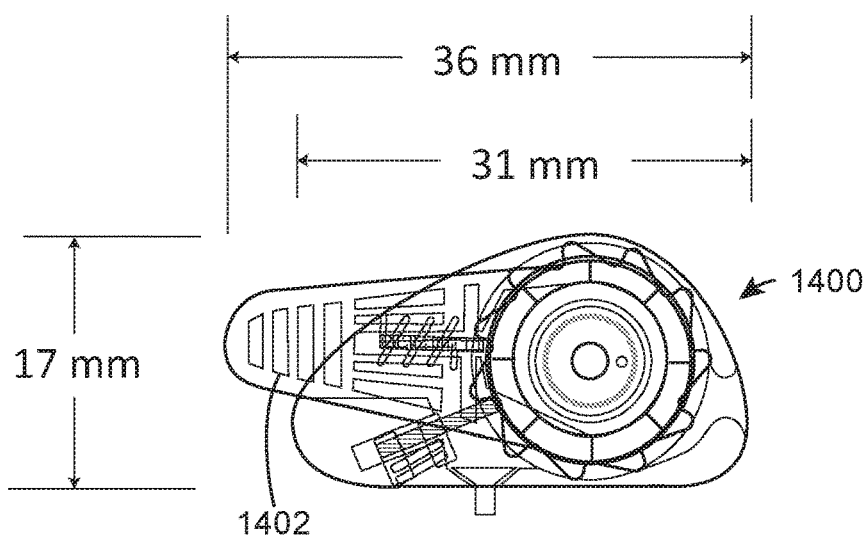
FIG. 89 shows details of another embodiment of an adjustment device where material is removed from the lever to reduce weight.

Inherently, all articles or devices that fit to the body are subjected to the forces of gravity. Suspension forces are forces generated by a fit system to counteract the forces of gravity and suspend the device onto the body. The weight of a fit system itself will contribute to the overall weight of the device and therefore lighter weight fit systems are preferable. The various embodiments of fit systems described herein may be made lighter by removing material and adding cutouts. For example, the embodiment of an adjustment device 1400 shown in FIG. 89 features material cutouts 1402 to remove material for the purpose of reducing the weight of the device 1400.

Figure 90:
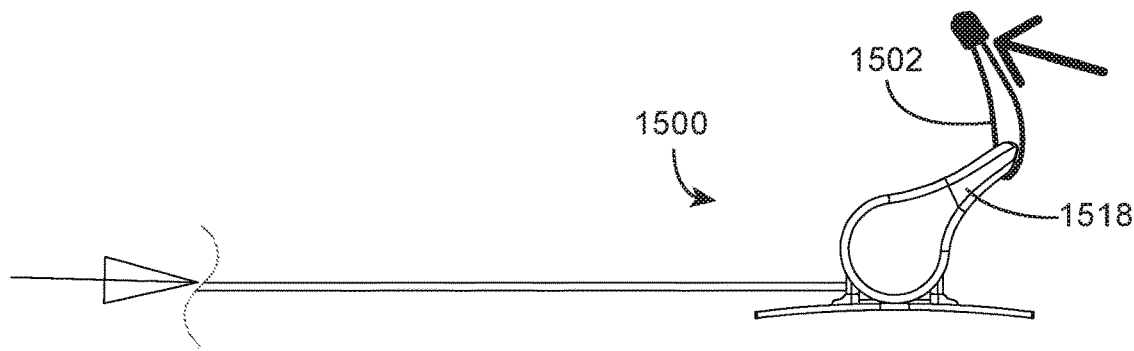
FIG. 90 shows a loop handle attached to a lever of another embodiment of a tension device.

Various modifications can be made to the levers of the fit systems described herein. For example, as shown in FIG. 90, a fabric or cable pull strap 1502 can be attached to a lever 1518 of an adjustment device 1500 and used as a pull by a user to actuate the lever 1518 back and forth in the direction of the arrows.

Figure 91:
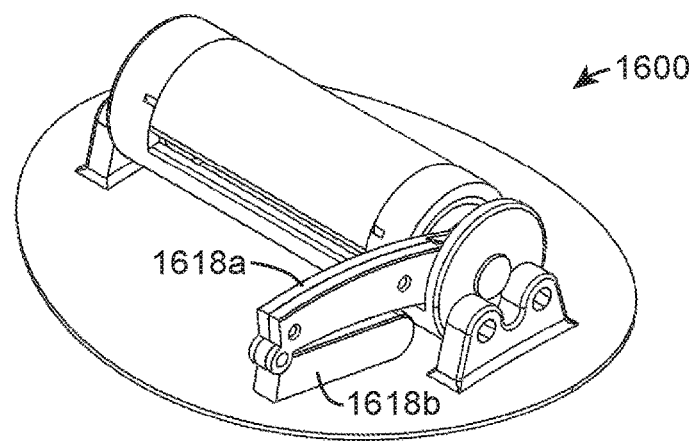
FIG. 91 shows another embodiment of a tension device that includes a folding lever, shown in a folded configuration.
Figure 92:
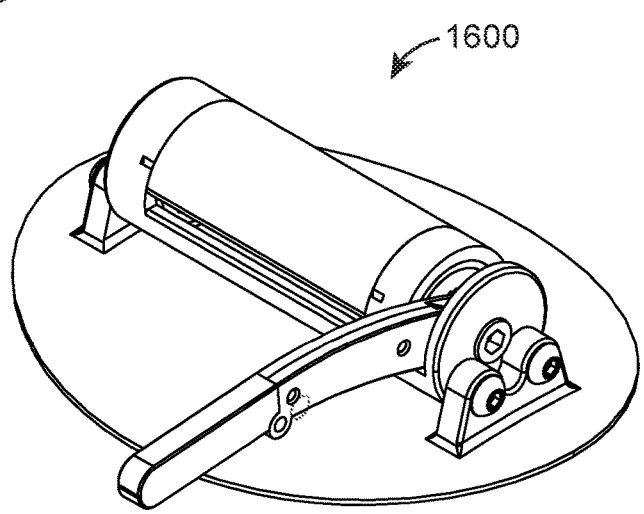
FIG. 92 shows the lever of FIG. 91 in an unfolded configuration.
Figure 104:
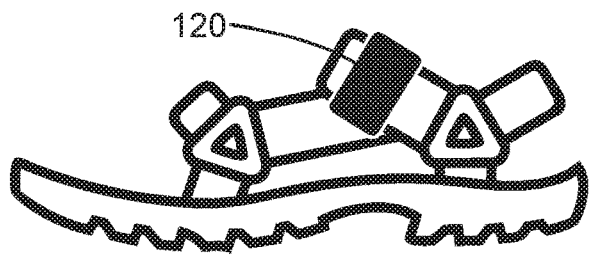

Also, as shown in FIGS. 91 and 92, the levers 1618 may be formed as sectional parts that can be connected to extend the length of the lever 11. In FIG. 91, an adjustment device 1600 has a lever that has two portions 1618a and 1618b connected by a hinge 1618c. In FIG. 104 portion 1618b is shown folded back on portion 1618a to conserve space when the lever 1618 is not being used. As shown in FIG. 92, the portion 1618b can be rotated about hinge 1618c to fully extend the length of the lever 1618 to provide the user with increased leverage for winding the spool.

Figure 93:
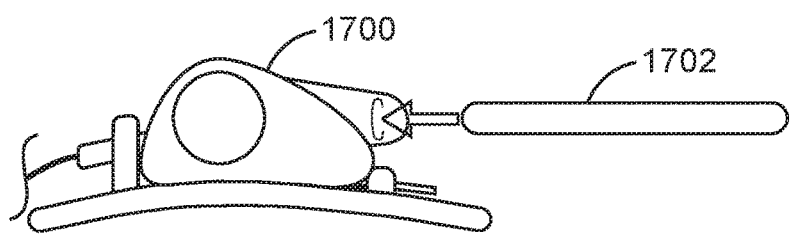
FIG. 93 shows another embodiment of a tension device that is configured to receive an extension bar, which is shown disconnected in FIG. 93.
Figure 94:
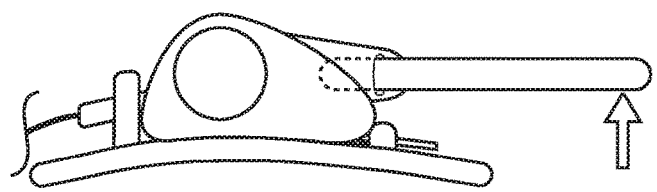
FIG. 94 shows tension device of FIG. 92 connected to the extension bar.

In another embodiment, an adjustment device 1700 (FIGS. 93 and 94) has a lever 1718 with a mount configured to mount an extension bar 1702 to increase leverage of the lever 1718. In the embodiment shown, the lever 1718 defines a receptacle opening into which one end of the bar can be inserted, as shown in FIG. 94. The bar 1702 may be stored separately from the device 1700 when not being used for adjusting adjustment device 1700.

Figure 95:
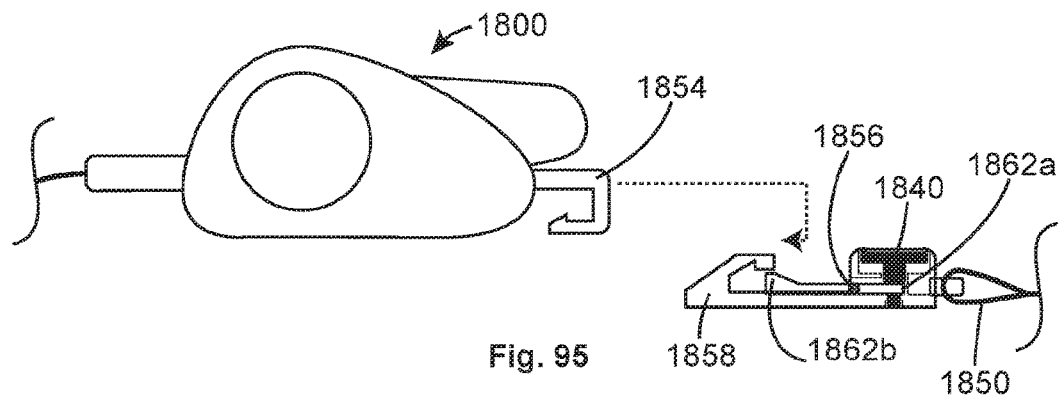
FIG. 95 shows another embodiment of a tension device that is configured to connect to a quick connect latch which is shown disconnected from the tension device.
Figure 96:
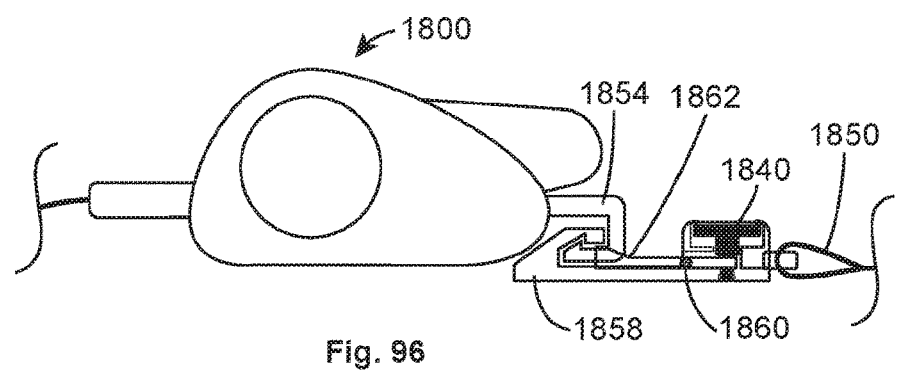
FIG. 96 shows the tension device and latch of FIG. 96 connected together.

FIGS. 95 and 96 show an embodiment of an adjustment device 1800 with an integrated quick catch 1854 that is configured to releasably connect to a mating latch 1858 which includes a quick release mechanism 1856. In this embodiment there is an opposing strap 1850 connected to the latch 1858. In other embodiments, the latch 1858 could be connected directly to a device fitting the body of the user or other member. In FIG. 95, the catch 1854 is detached from the latch 1858 and as such allows for easy donning and doffing and to be applied to products that require a full opening of one or more portions of the device. This figure is shown at a 1:1 scale.

FIG. 96 shows the catch 1854 connected to the latch 1854. The quick release mechanism 1856 includes a quick release push-up tab 1862, which is configured to pushes the base side of quick connect 1854 to release from the latch 1858 when a release button 1840 is depressed. Specifically, the tab 1862 is pivotally connected to the latch 1858 at pivot 1860 so that when the button 1840 is depressed, the button 1840 pushes a first end 1862a of the tab 1862 down to raise a second opposed end 1862b of the tab 1862. The movement of the second end 1862 of the tab 1862 opens the quick connect 1854 to release it form the latch 1858. The catch 1854 and latch 1858 may include magnetics to guide their connection.

Figure 97:
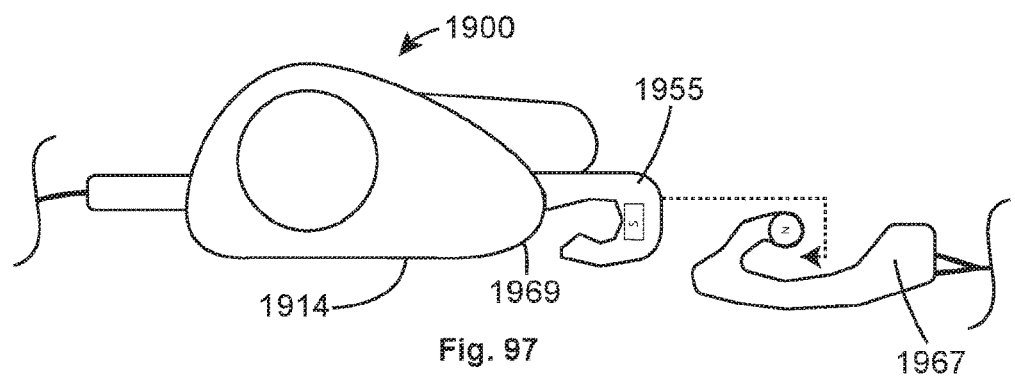
FIG. 97 shows another embodiment of a tension device that includes a magnetic hook configured to connect to a magnetic hook connected to a tension line. The magnetic hook connected to a tension line is also shown, but with the hooks shown disconnected.

FIG. 97 shows a side view of an adjustment device 1900 in accordance with an aspect of the disclosure. The fits device 1900 includes an integrated quick catch 1955 that is configured to connect to a mating catch 1967. Wherein the catch 1955 is formed as a hook with a barreled end 1964, mating surface 1966, and a south pole magnet 1980 for magnetic connection. The opposing catch 1967 has complementary and mating features to those of the catch 1955, including a barreled end 1963, mating surface 1966, and a north pole magnet 1970 for magnetic connection. The catch 1967 also includes a nesting surface 1968 that matches a curvature 1969 of a base 1914 of the adjustment device 1900. In FIG. 97, the catches 1955 and 1967 are disconnected, which may be necessary to don a device or to retract the fit device base to the approximate length necessary, then use the lever arm and mechanism to apply the desired load onto the body.

Figure 98:
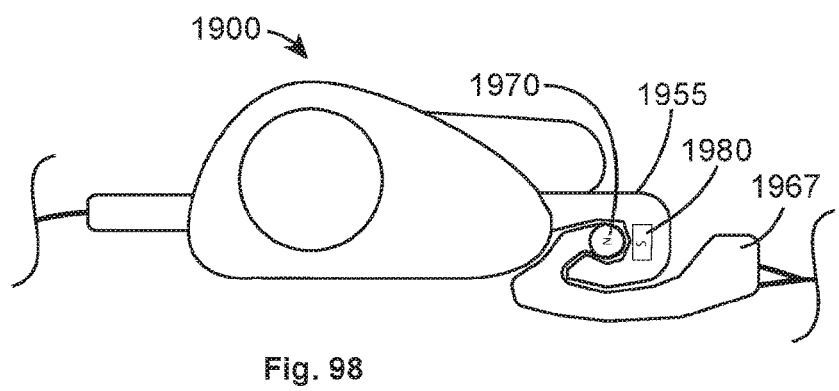
FIG. 98 shows the magnetic hooks of FIG. 97 connected.

FIG. 98 shows the adjustment device 1900 connected to the catch 1967. Specifically, quick catch 1955 and catch 1967 are joined together. The catches 1955 and 1967 come together more easily and are aligned by the magnets 1980 and 1970. In this embodiment, the catches 1955 and 1967 are shifted perpendicular to the catching mechanism (i.e., into or out of the page in FIG. 111) to release the two catches 1955 and 1967 from one another. Since this motion of the catches 1955 and 1967 imposes a sheer force on the magnets 1980 and 1970, the force of the magnets is easily overcome by the user and yet is strong enough to avoid inadvertent disconnection.

In FIGS. 99b-122 show various uses of adjustment devices in fit systems and line tensioning systems. In describing the various systems 120 (fit systems and line tensioning systems) shown in FIGS. 99b-122, reference will be made to an adjustment device thereof, which can be any of the adjustment devices described herein in accordance with this disclosure. It will be appreciated that adjustment device 120 may take the form of any of the embodiments of an adjustment device described herein and is not limited to the schematics shown in FIGS. 99b-122.

Figures 99A, 99B:
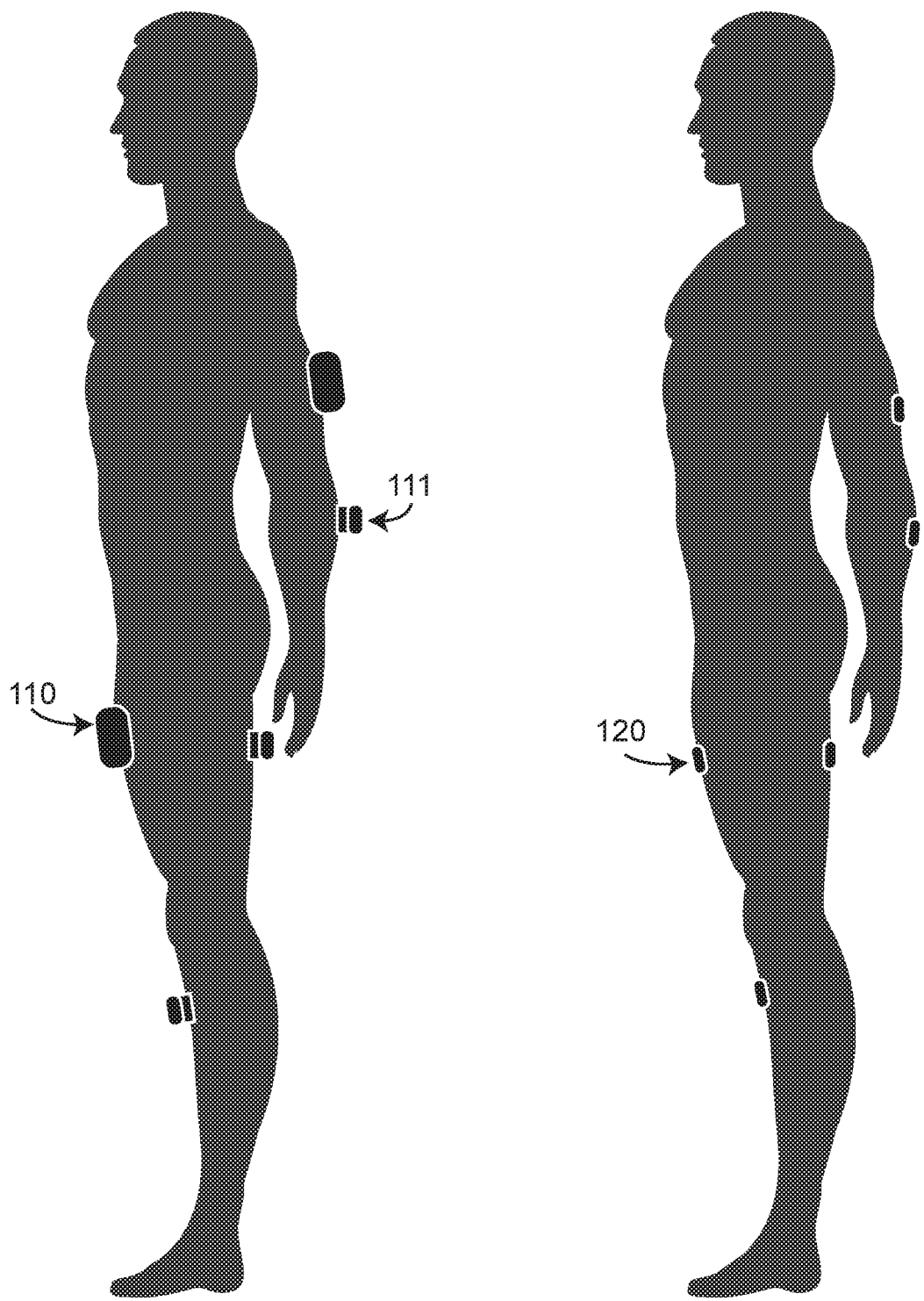
FIG. 99*a* shows schematic prior art tension devices and fit systems connected to a human body.
FIG. 99*b* shows schematic exemplary fit systems using tension devices in accordance with the disclosure connected to a human body.

FIG. 99a shows a side view of a human profile wherein the body has been fit with various devices or garments that include ratchet strap systems 110 and a rotary dial adjustment device 111 of the prior art. By way of comparison to the prior art systems 110 and 111 shown in FIG. 99a, the systems 120 in accordance with an aspect of the disclosure shown in FIG. 99b have a lower profile. The larger profile of the prior art systems 110 and 111 are bulkier and can cause increased impact force on the portion of the body attached to the systems 110 and 111 if a user falls or is impact in that area of the user's body.

Figure 100:
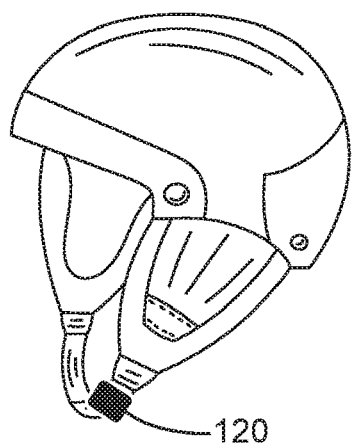
FIGS. 100-122 show schematic representations of fit systems and line tensioning systems in accordance with the disclosure that are configured for various fields of use.

FIGS. 100-108, and 111-122 show fit systems 120 connected to wearable articles. FIG. 100 shows a fit system 120 connected to a helmet and used as helmet strap. The adjustment device of the fit system may be mounted to the shell of the helmet or may be left free to be positioned along the strap at an intermediate position between the sides of the helmet.

Figure 101:
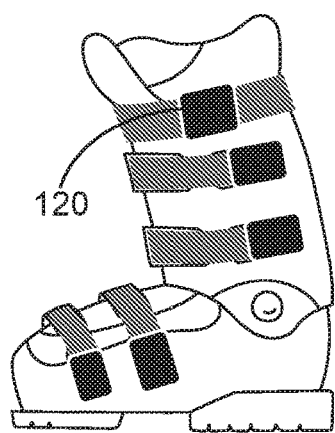
Figure 102:
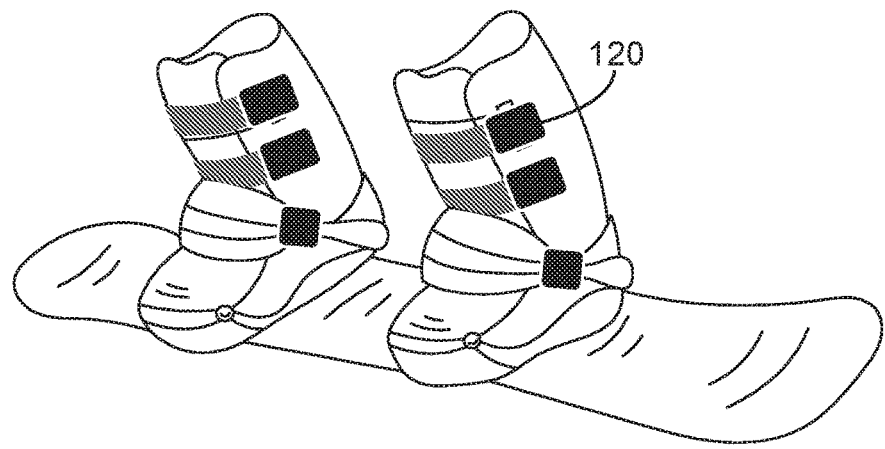

FIG. 101 shows multiple fit systems 120 connected to a ski boot. The straps are banded around a leg portion and a foot portion of the boot and the adjustment devices of the straps may be mounted directly to the leg and foot portions of the boot. FIG. 102 shows fit systems 120 connected to snowboard boots. Straps of the systems are banded about the leg portion of the snowboard boots with the adjustment device mounted directly to the boot. Also, straps of the fit system 120 are shown connected to the snowboard and include adjustment devices mounted to the snowboard straps which can be used to adjust the connection of the snowboard boots to the snowboard.

Figure 103:
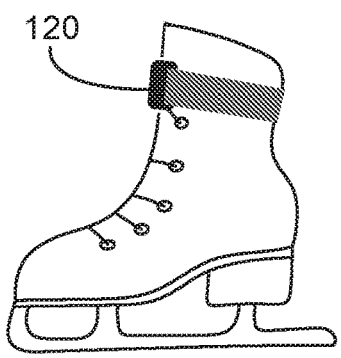
Figure 105:
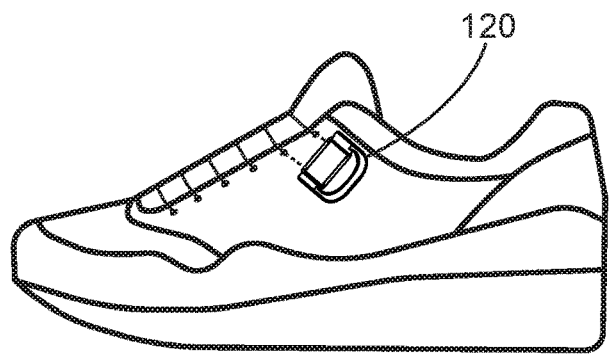
Figure 106:
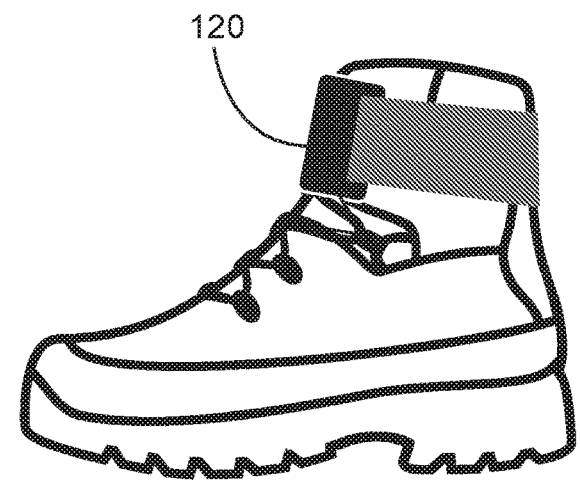

FIG. 103 shows a fit system 120 connected to a skate, specifically an ice skate. The adjustment device of the fit system is mounted directly to the skate while the tension line is banded about the skate. FIG. 104 shows an embodiment of a fit system 120 connected to a sandal. The adjustment device of the fits system is mounted to one of the sandal straps while the tension line takes the place of a sandal closure strap. FIG. 105 shows a fit system 120 connected to a shoe. The adjustment device of the system is mounted to the shoe and the strap extends across the tongue of the shoe. FIG. 106 shows a fit system 120 connected to a boot, where the fit system is arranged identically to the system shown in FIG. 103 used with a skate.

Figure 107:
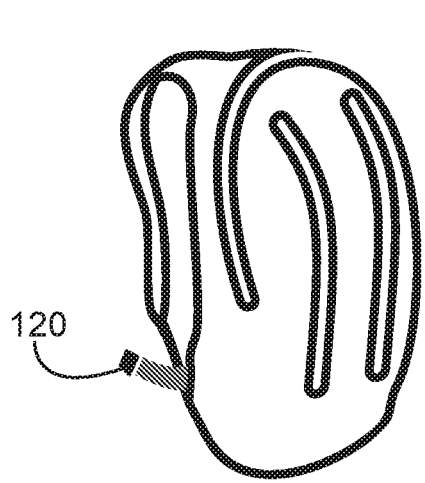
Figure 108:
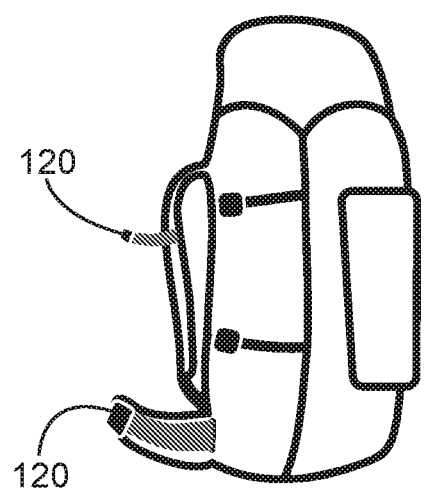

FIG. 107 shows an embodiment of a fit system 120 used for an adjustable strap of a day pack application. The tension line of the system 120 is connected to the day pack and the adjustment device is not directly mounted to the day pack but is spaced therefrom. FIG. 108 shows a fit system 120 used for an adjustable strap of a bag or backpack (e.g., a camping backpack). The tension line of the system 120 is connected to the backpack and the adjustment device is not directly mounted to the backpack but is spaced therefrom.

Figure 111:
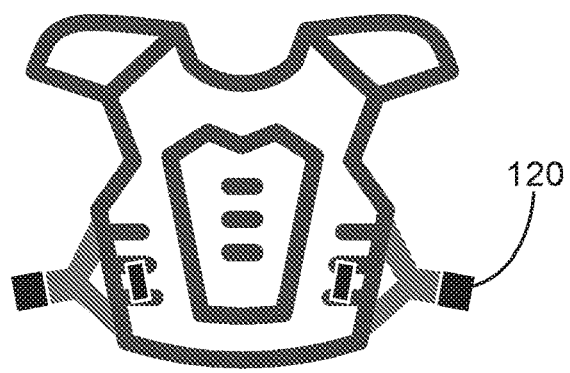
Figure 112:
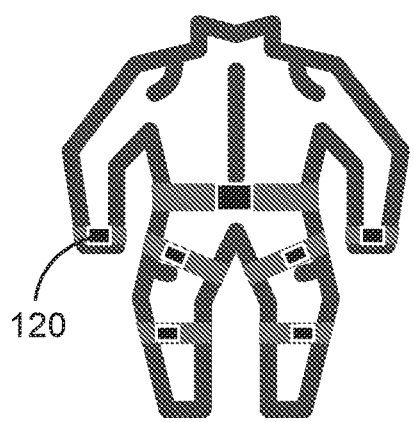
Figure 113:
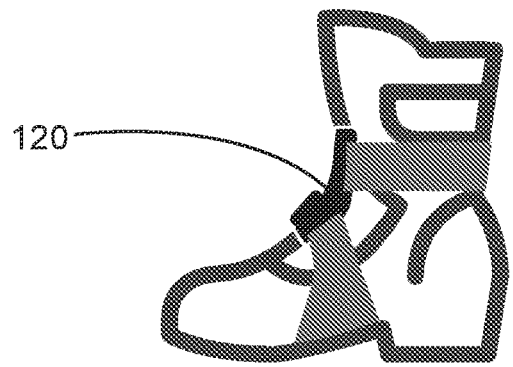
Figure 114:
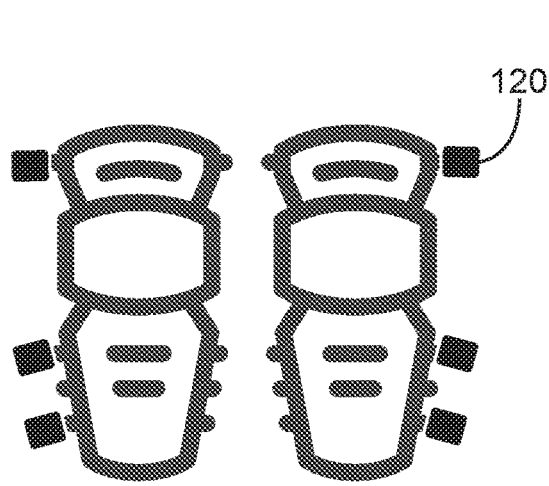
Figure 115:
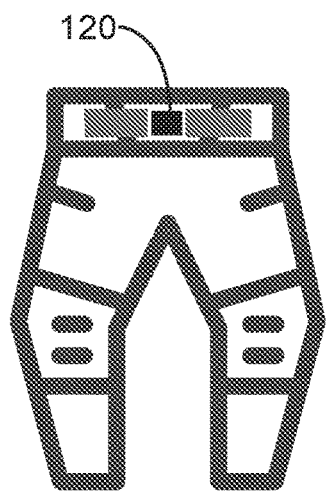

FIGS. 111-115 show fit systems 120 applied to protectable wearable articles utilized in the field of motorsports. Specifically, FIG. 111 shows fit systems 120 applied to a protective vest that can be used to adjust the fit of the vest to a user. FIG. 112 shows fit systems 120 applied to a protective suit. The fit systems can be used to adjust the fit of the protective suit to a user's body at the locations shown in FIG. 112. FIG. 113 shows a fit system 120 applied to a motorcycle boot. As shown in FIG. 113, two straps are banded about the boot: one strap banded about a leg portion of the boot and one strap banded about the foot. Separate adjustment devices may be provided for each strap to independently tension each strap. FIG. 114 shows fit systems 120 applied to protective knee pads where the strap is configured to be banded about the knee of a user and the adjustment device is can be used to adjust the fit of the straps. FIG. 115 shows a fit system 120 applied to protective pants for adjusting the waist of the pants to fit a waist of a user.

Figure 121:
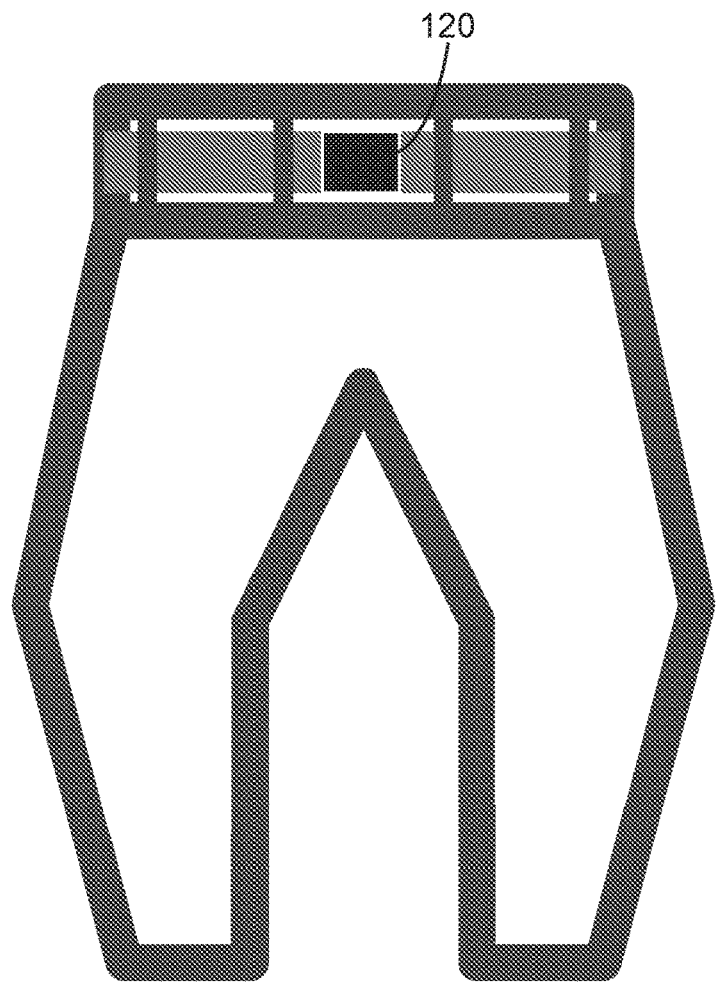
Figure 122:
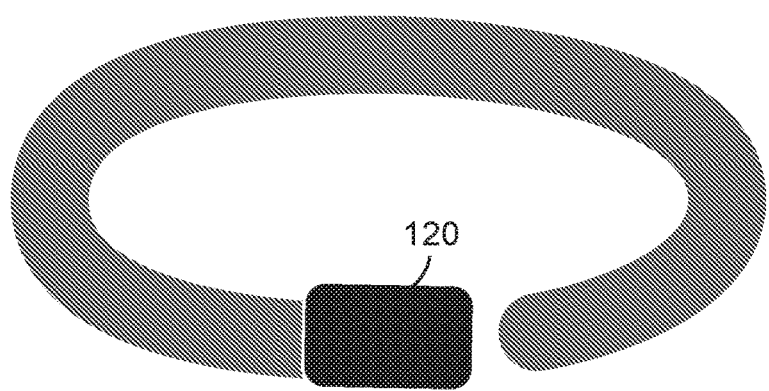

FIGS. 121 and 122 show fit systems 120 utilized in the field of clothing accessories and clothing. As shown in FIG. 121, the fit system 120 is used as a belt for a pair of pants, which may be integrated into the pants. For example, the adjustment device may be mounted to the pants with the strap of the fit system 120 banded about the waist of the pants. FIG. 122 shows the fit system 120 in the form of a belt. Where the fit system 120 is worn about the body, it is preferred to incorporate a tension limiter. However, in certain applications where the fit system 120 is intended to apply tension around the body, such as a tourniquet, it will be appreciated that the tension device of the fit system 120 would omit a tension limiter.

Figure 116:
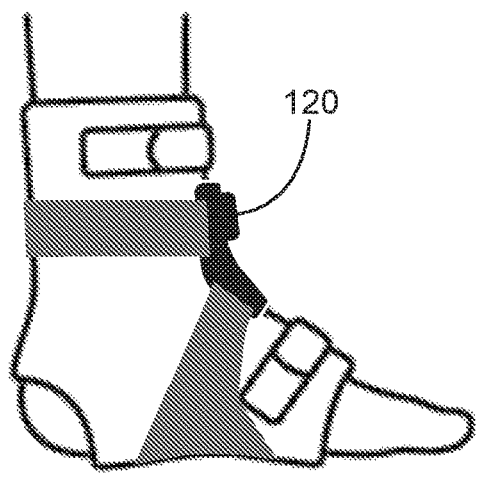
Figure 117:
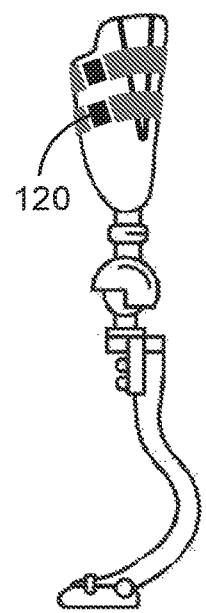
Figure 118:
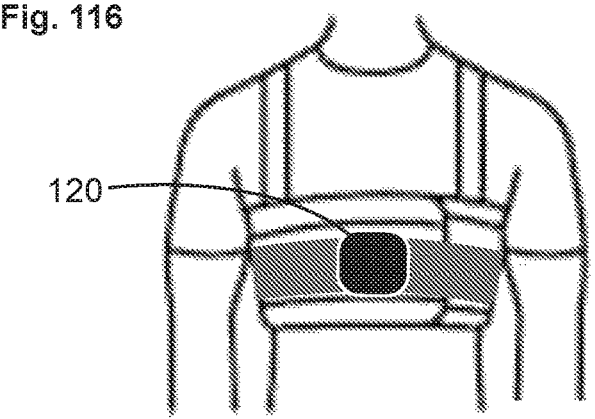
Figure 119:
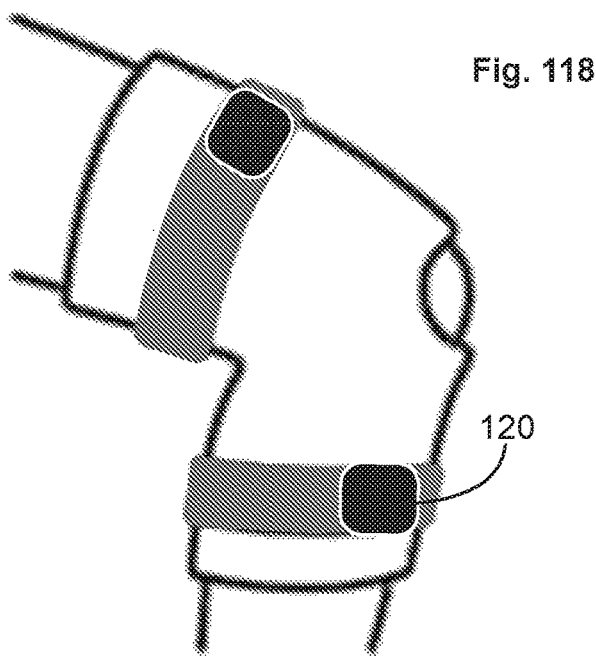
Figure 120:
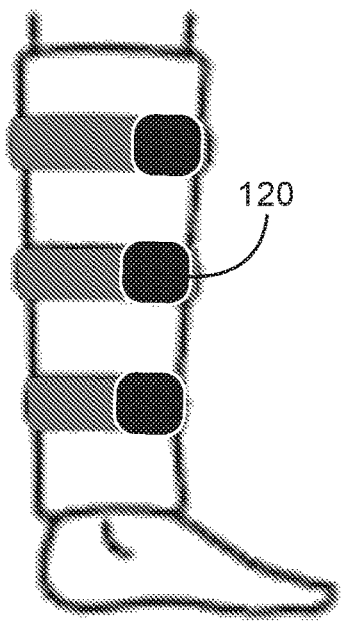

FIGS. 116-120 show various uses of the fits systems 120 in the field of orthopedics. FIG. 116 shows a fit system 120 utilized in the field of orthopedics applied to an ankle brace or ankle orthosis. As shown in FIG. 116 one strap is banded about a leg portion of the brace and one strap is banded about a foot portion of the brace. The adjustment device of the fit system 120 is mounted to the device and controls tension in the two straps. FIG. 117 shows fit systems 120 applied to a prosthetic socket. For the socket, adjustment devices are connected to the socket at various locations and are connected by tension lines. Applying or relieving tension in the tension lines can enlarge or reduce the opening of the prosthetic to adjust the fit of the prosthetic to a user. FIG. 118 shows a fit system 120 applied to a back brace or thoracic lumbar sacral orthosis (TLSO) application. The strap of the system 120 is banded about the back and torso of the user and the adjustment device is positioned over a user's chest for access to the user. FIG. 119 shows fit systems 120 applied to a knee brace or knee orthosis. One fit system is banded about the leg above the knee, while another fit system is banded about the leg below the knee. The adjustment devices of the fit systems 120 can adjust tension in the straps to fit the straps to the user's leg. FIG. 120 shows fit systems 120 applied to a post-operative knee brace or knee immobilizer. The fit systems are shown banded about the user's lower leg.

Figure 109:
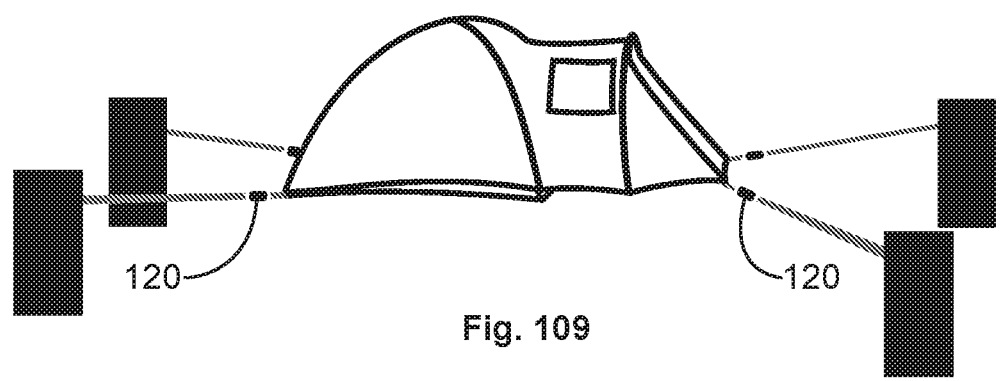
Figure 110:
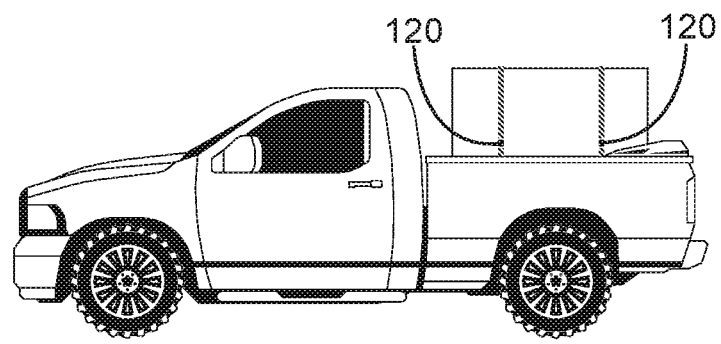

FIGS. 109 and 110 show uses of line tensioning systems 120. FIG. 109 shows fit systems 120 used as straps of a suspended tent. Each strap is connected to a corresponding adjustment device. Each strap is configured to connect at one end to a tent and an opposite end to another structure (such as a tree) to suspend the tent above the ground. The line tensioning systems may also be used for other suspensions applications, such as mountaineering, rock-climbing, and rappelling. Similarly, the line tensioning system may be used to tension sporting nets, such as for tennis, badminton, volleyball, table tennis, etc., and may be provided with the equipment therefor. FIG. 110 shows line tensioning systems 120 used as cargo tie down straps connected to a truck bed. The line tensioning systems described herein can also be used as closures in carry-alls, suitcases, duffel bags, sport bags, and thus may be incorporated into such articles in accord with the intended scope herein.

There have been described and illustrated herein several embodiments of a tension device, fit systems using the tension device, and a method of using the tension devices and fit systems. While particular embodiments of the invention have been described, it is not intended that the invention be limited thereto, as it is intended that the invention be as broad in scope as the art will allow and that the specification be read likewise. Thus, while particular tension line types have been disclosed, it will be appreciated that other tension line types may be used as well. For all of the embodiments, the line tensioning systems may be made from a plastic, metal, or a combination plastic and metal components. In addition, while particular types of plastics have been disclosed for parts of the embodiments, it will be understood that other suitable types of plastics can be used. For example, and not by way of limitation, acrylic and polycarbonate may be used. Moreover, while particular configurations have been disclosed in reference to housings for the tension devices, it will be appreciated that other configurations could be used as well. It will therefore be appreciated by those skilled in the art that yet other modifications could be made to the provided invention without deviating from its spirit and scope as claimed.

What is claimed is:

1. A lever-operated adjustment device for use with at least one tension line, the adjustment device comprising:
   a housing supporting a rotatable spool that is operably coupled to the at least one tension line, wherein the spool is configured to rotate about a first axis in a first rotational direction to wind the at least one tension line around the spool, and wherein the spool is further configured to rotate about the first axis in a second rotational direction opposite the first rotational direction to unwind the at least one tension line from the spool;
   a lever pivotally coupled to the housing and configured to rotate about a second axis perpendicular to the first axis, wherein the lever is selectively coupled to the spool to drive rotation of the spool in the first rotational direction; and
   a release mechanism that is configured to selectively release the spool such that the spool is free to rotate in either the first rotational direction or the second rotational direction in response to manual forces applied to the release mechanism.

2. The adjustment device according to claim 1, wherein the housing includes a base with a lower surface extending in a plane and the release mechanism is configured to release the spool in response to a manual force applied in a first direction perpendicular to the first axis and parallel to the plane of the lower surface of the base.

3. The adjustment device according to claim 1, further comprising:
   a ratcheting adjustment mechanism supported by the housing and the lever,
   wherein the ratcheting adjustment mechanism includes first and second engagement members,
   wherein the first engagement member is operably coupled between the lever and the spool, wherein the first engagement member has a coupled configuration that mechanically couples the lever to the spool such that pivoting motion of the lever drives the spool in the first rotational direction and prevents the spool from rotating in the second rotational direction, and wherein the first engagement member has a decoupled configuration that mechanically decouples the lever from the spool,
   wherein the second engagement member is selectively coupled to the spool, wherein the second engagement member has a coupled configuration that permits the spool to rotate in the first rotational direction while preventing the spool from rotating in the second rotational direction, and wherein the second engagement member has a decoupled configuration that that mechanically decouples the second engagement member from the spool,
   wherein the release mechanism is configured to selectively release the spool by simultaneously configuring the first and second engagement members into their respective decoupled configurations.

4. The adjustment device according to claim 3, further comprising:
   a tension limiter coupled between the lever and the ratcheting adjustment mechanism.

5. The adjustment device according to claim 3, wherein:
the spool includes an axle extending along the first axis and a driven gear rotationally coupled to the axle, and
the lever is coupled to a driving gear configured to engage the driven gear of the spool.

6. The adjustment device according to claim 5, wherein the axle defines,
an elongated slotted opening to retain a flat strap tension line, and/or
at least one hole configured to retain a cable or lace tension line having a round cross section.

7. The adjustment device according to claim 5, wherein:
the driven gear is a hypoid gear, and the driving gear is a helical gear.

8. The adjustment device according to claim 1, wherein the housing includes a base having a lower surface extending in a plane and a cover coupled to the base and surrounding the spool.

9. The adjustment device according to claim 8, wherein the first axis is perpendicular to the plane of the lower surface of the base.

10. The adjustment device according to claim 8, wherein the base has a mounting flange for mounting the adjustment device to a substrate and wherein the mounting flange is configured to be sewn to the substrate, to be connected to the substrate with snap-fit connection, or be connected to the substrate with adhesive.

11. The adjustment device according to claim 1, wherein the adjustment device has a mechanical advantage of over 2:1.

12. A system comprising:
an adjustment device according to claim 1; and
at least one tension line connected to the spool.

13. The system according to claim 12, further comprising:
an article, wherein the adjustment device is operable to increase or decrease tension in the at least one tension line to adjust a dimension of the article.

14. The system according to claim 12, further comprising:
a wearable article, wherein the adjustment device is operable to increase or decrease tension in the at least one tension line to adjust a fit of the wearable article.

15. A method of adjusting tension in a tension line, comprising:
providing a lever-operated adjustment device according to claim 1; and
pivoting the lever about the second axis to drive the spool in the first direction to wind the tension line into increase tension in the tension line.

16. The adjustment device according to claim 1, wherein the release mechanism is configured to release the spool in response to a manual force applied in a direction perpendicular to the first axis.

17. The adjustment device according to claim 1, wherein the release mechanism is configured to release the spool in response to a manual force applied in a direction parallel to the second axis.

18. The adjustment device according to claim 1, wherein:
the lever is mounted on a shaft having first and second ends, and the lever extends in a U-shape from the first end of the shaft to the second end of the shaft.

* * * * *